(12) United States Patent
Dandu et al.

(10) Patent No.: US 8,524,713 B2
(45) Date of Patent: Sep. 3, 2013

(54) SUBSTITUTED SPIROCYCLIC PIPERIDINE DERIVATIVES AS HISTAMINE-3 ($H_3$) RECEPTOR LIGANDS

(75) Inventors: Reddeppa reddy Dandu, Downingtown, PA (US); Robert L. Hudkins, Chester Springs, PA (US); Babu G. Sundar, West Chester, PA (US)

(73) Assignee: Cephalon, Inc, Frazer, PA (US)

( * ) Notice: Subject to any disclaimer, the term of this patent is extended or adjusted under 35 U.S.C. 154(b) by 313 days.

(21) Appl. No.: 12/846,108

(22) Filed: Jul. 29, 2010

(65) Prior Publication Data

US 2010/0298332 A1    Nov. 25, 2010

Related U.S. Application Data

(63) Continuation of application No. PCT/US2009/032195, filed on Jan. 28, 2009.

(60) Provisional application No. 61/062,909, filed on Jan. 30, 2008.

(51) Int. Cl.
*A01N 43/58* (2006.01)
*A61K 31/50* (2006.01)
*C07D 237/00* (2006.01)
*C07D 331/02* (2006.01)

(52) U.S. Cl.
USPC ........... 514/248; 514/252.04; 544/230; 549/1

(58) Field of Classification Search
USPC .............. 514/248, 252.04; 544/230; 549/1
See application file for complete search history.

(56) References Cited

U.S. PATENT DOCUMENTS

2005/0159438 A1 * 7/2005 Dolle et al. ................ 514/278
2006/0217375 A1 * 9/2006 Barker et al. ............. 514/232.5

FOREIGN PATENT DOCUMENTS

| WO | WO2004111056 | * | 12/2004 |
| WO | 2007/055418 A1 | | 5/2007 |
| WO | 2007/063385 A2 | | 6/2007 |
| WO | 2007/088462 A1 | | 8/2007 |

OTHER PUBLICATIONS

Willams et al. (Foye's Principles of Medicinal Chemistry, Fifth Edition, 2002, p. 59-63).*

* cited by examiner

*Primary Examiner* — Sreeni Padmanabhan
*Assistant Examiner* — Uma Ramachandran

(57) ABSTRACT

The present invention provides compounds of Formula (I):

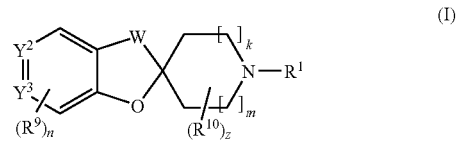

their use as $H_3$ antagonists/inverse agonists, processes for their preparation, and pharmaceuticals compositions thereof.

29 Claims, No Drawings

SUBSTITUTED SPIROCYCLIC PIPERIDINE DERIVATIVES AS HISTAMINE-3 ($H_3$) RECEPTOR LIGANDS

CROSS-REFERENCE TO RELATED APPLICATIONS

This application is a continuation of International Application No. PCT/US2009/032195, filed Jan. 28, 2009, which claims priority to U.S. Provisional Application Ser. No. 61/062,909, filed Jan. 30, 2008. The disclosures of the aforementioned applications are incorporated herein by reference in their entireties for all purposes.

TECHNICAL FIELD

The present invention is related to substituted spirocyclic piperidine derivatives, their use as $H_3$ antagonists/inverse agonists, processes for their preparation, and pharmaceuticals compositions thereof.

BACKGROUND

Publications cited throughout this disclosure are incorporated in their entirety herein by reference.

Histamine is a well established modulator of neuronal activity. At least four subtypes of histamine receptors have been reported in the literature—$H_1$, $H_2$, $H_3$, $H_4$. The histamine $H_3$ receptors play a key role in neurotransmission in the central nervous system. The $H_3$ receptor was discovered in 1983 originally on histamine-containing neurons where it was shown to function presynaptically, regulating the release and synthesis of the biogenic amine histamine (Arrang et al, 1983) now a well established neurotransmitter. $H_3$ receptors are predominately expressed in the brain, localizing to the cerebral cortex, amygdala, hippocampus, striatum, thalamus and hypothalamus. $H_3$ receptors are also localized presynaptically on histaminergic nerve terminals and act as inhibitory autoreceptors (Alguacil and Perez-Garcia, 2003; Passani et al, 2004; Leurs at al, 2005; Celanire et al, 2005; Witkin and Nelson, 2004). When these receptors are activated by histamine, histamine release is inhibited. $H_3$ receptors can also be found in the periphery (skin, lung, cardiovascular system, intestine, GI tract, etc). $H_3$ receptors are also involved in presynaptic regulation of the release of acetylcholine, dopamine, GABA, glutamate and serotonin (see Repka-Ramirez, 2003; Chazot and Hann, 2001; Leurs et al, 1998). The $H_3$ receptor demonstrates a high degree of constitutive or spontaneous activity (e.g., receptor is active in the absence of agonist stimulation) in vitro and in vivo, thus, ligands to the receptor can display, agonist, neutral antagonist or inverse agonist effects.

The location and function of histaminergic neurons in the CNS suggests that compounds interacting with the $H_3$ receptor may have utility in a number of therapeutic applications including narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders and epilepsy (Leurs et al, 2005; Witkin and Nelson, 2004, Hancock and Fox 2004; Esbenshade et al. 2006). An $H_3$ antagonist/inverse agonist could be important for gastrointestinal disorders, respiratory disorders such as asthma, inflammation, and myocardial infarction.

Ohtake et al. (US 2006/0178375 A1) disclosed compounds that reportedly exhibit histamine receptor $H_3$ antagonist or inverse agonist activity and may be useful for the treatment or prevention of obesity, diabetes, hormonal secretion abnormality, or sleep disorders.

Celanire et al. (WO 2006/103057 A1 and WO 2006/103045) have disclosed compounds comprising an oxazoline or thiazoline moiety, processes for preparing them, their pharmaceutical compositions and their uses as $H_3$ ligands.

Bertrand et al. (WO 2006/117609 A2) disclosed novel histamine $H_3$ receptor ligands, processes for their preparation, and their therapeutic applications.

Schwartz et al. (WO 2006/103546 A2) disclosed certain methods of treatment for Parkinson's disease, obstructive sleep apnea, narcolepsy, dementia with Lewy bodies, and/or vascular dementia using non-imidazole alkylamine derivatives that are antagonists of the $H_3$ receptors of histamine.

Apodaca et al. (EP 1 311 482 B1) disclosed certain non-imidazole aryloxypiperidines as $H_3$ receptor ligands, their synthesis, and their use for the treatment of disorders and conditions mediated by the histamine receptor.

Xu et al. disclosed certain 6-substituted phenyl-4,5-dihydro-3(2H)-pyridazinones, their synthesis, and rabbit platelet aggregation inhibitory activity induced by ADP in vitro.

Barker et al. (US 2006/0217375) discloses spiro[benzodioxane] compounds as active antagonists of the orexin-1 receptor and potentially useful in the prophylaxis and treatment of orexin-1 receptor related disorders and orexin-2 receptor related disorders.

Thus, there is a need for novel classes of compounds that interact with the $H_3$ receptor.

SUMMARY

The present invention is directed to compounds of Formula (I):

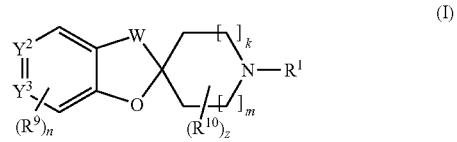

and the stereoisomeric forms, mixtures of stereoisomeric forms, and pharmaceutically acceptable salt forms thereof, wherein:

$R^1$ is H, $C_1$-$C_4$ alkyl, or $C_3$-$C_8$ cycloalkyl;
W is —$CH_2$—, —$CH_2CH_2$—, or —$CH_2$—O—;
k is 0, 1, or 2; m is 0, 1, or 2; and the sum of m and k is 1, 2, or 3;
$Y^2$=$Y^3$ is —C(X)=CH— or —CH=C(X)—;
X is $R^2$, —$OR^2$, —($C_1$-$C_3$ alkyl)-$R^2$, —O—($C_1$-$C_3$ alkyl)-$R^2$, —$NHR^2$, —NHC(=O)$R^2$, or —NHC(=O)NH$R^2$;
wherein said $C_1$-$C_3$ alkyl is optionally substituted with —OH or $C_1$-$C_4$ alkoxy;

$R^2$ is

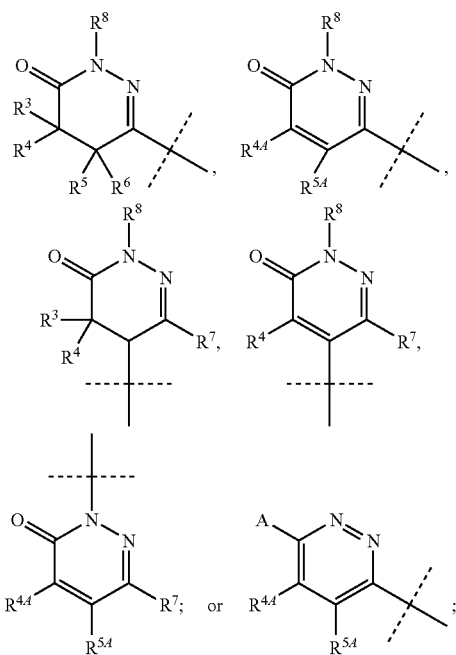

A is F, Cl, or Br;
$R^3$ is H, F, or $C_1$-$C_4$ alkyl;
$R^4$ is H, F, or $C_1$-$C_4$ alkyl;
$R^{4A}$ is H, F, Cl, Br, or $C_1$-$C_4$ alkyl;
$R^5$ is H, F, or $C_1$-$C_4$ alkyl;
$R^{5A}$ is H, F, Cl, Br, $C_1$-$C_4$ alkyl or phenyl;
alternatively, $R^4$ and $R^5$, together with the carbon atoms to which they are attached, may form a fused $C_3$-$C_6$ cycloalkyl ring optionally substituted with 1, 2, or 3 $R^{14}$;
alternatively, $R^{4A}$ and $R^{5A}$, together with the carbon atoms to which they are attached, may form
 a fused phenyl ring optionally substituted with 1, 2, or 3 $R^{14}$;
 a $C_3$-$C_6$ cycloalkyl ring optionally substituted with 1, 2 or 3 $R^{14}$;
 a 5 to 6 membered fused heteroaryl ring system containing one, two, or three heteroatoms selected from N, O, and S, wherein said heteroaryl ring system is optionally substituted with 1, 2, or 3 $R^{14}$; or
 a 5 to 6 membered fused heterocycloalkyl ring system containing one, two, or three heteroatoms selected from N, O, S, SO, and $SO_2$, wherein said heterocycloalkyl ring system is optionally substituted with 1, 2, or 3 $R^{14}$;
$R^6$ is H, F, or $C_1$-$C_4$ alkyl;
$R^7$ is H, F, Cl, Br, or $C_1$-$C_4$ alkyl;
$R^8$ is H, —C(=O)$R^{27}$, —$CO_2R^{27}$, $C_1$-$C_6$ alkyl optionally substituted by 1-3 $R^{20}$;
 $C_3$-$C_8$ cycloalkyl optionally substituted by 1-3 $R^{20A}$;
 $C_6$-$C_{10}$ aryl optionally substituted by 1-3 $R^{20A}$;
 $C_7$-$C_{15}$ arylalkyl optionally substituted by 1-3 $R^{20A}$; or
 a 5 to 10 membered heteroaryl ring system containing one, two, or three heteroatoms selected from N, O, and S, wherein said heteroaryl ring system is optionally substituted with 1-3 $R^{20A}$;
$R^9$, at each occurrence, is independently F, Cl, Br, $C_1$-$C_4$ alkyl, or $C_1$-$C_4$ alkoxy;
$R^{10}$ is F, Cl, Br, $C_1$-$C_3$ alkyl, or $C_1$-$C_3$ alkoxy;

$R^{14}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(=O)$OR^{21}$, —OC(=O)$NR^{23}R^{24}$, —$NR^{27}$C(=S)$R^{21}$, —$SR^{21}$, —S(O)$R^{21}$, or —S(O)$_2R^{21}$; $C_1$-$C_6$ alkyl optionally substituted with $OR^{26}$; $C_2$-$C_6$ alkenyl, or $C_2$-$C_6$ alkynyl;
$R^{20}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(O)$OR^{21}$, —OC(=O)$NR^{23}R^{24}$, —$NR^{27}$C(=S)$R^{21}$, —$SR^{21}$, —S(O)$R^{21}$, or —S(O)$_2R^{21}$; $C_1$-$C_6$ alkyl optionally substituted with $OR^{26}$; $C_2$-$C_6$ alkenyl, $C_2$-$C_6$ alkynyl, $C_3$-$C_7$ cycloalkyl, phenyl, 3- to 7-membered heterocycloalkyl group, or 5- or 6-membered heteroaryl group;
$R^{20A}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(=O)$OR^{21}$, —OC(=O)$NR^{23}R^{24}$, —$NR^{27}$C(=S)$R^{21}$, —$SR^{21}$, —S(O)$R^{21}$, or —S(O)$_2R^{21}$; $C_1$-$C_6$ alkyl optionally substituted with $OR^{26}$; $C_2$-$C_6$ alkenyl, or $C_2$-$C_6$ alkynyl;
$R^{21}$ at each occurrence is independently H, $C_1$-$C_6$ alkyl, $C_6$-$C_{10}$ aryl, or $C_7$-$C_{15}$ arylalkyl;
$R^{22}$ at each occurrence is independently the residue of an amino acid after the hydroxyl group of the carboxyl group is removed;
$R^{23}$ and $R^{24}$ at each occurrence is independently selected from H, $C_1$-$C_6$ alkyl, and $C_6$-$C_{10}$ aryl;
alternatively, $R^{23}$ and $R^{24}$, together with the nitrogen atom to which they are attached, form a 3 to 7 membered heterocycloalkyl ring system containing one, two, or three heteroatoms selected from N, O, and S, wherein said heterocycloalkyl ring system is optionally substituted with =O;
$R^{26}$ is H or $C_1$-$C_6$ alkyl;
$R^{27}$ is H or $C_1$-$C_6$ alkyl;
n is 0, 1, 2, or 3; and
z is 0, 1, 2, 3, 4, 5, or 6.

The present invention is also directed to methods of making compounds of Formula (I), as well as methods of their pharmaceutical use.

DETAILED DESCRIPTION OF ILLUSTRATIVE EMBODIMENTS

In preferred embodiments, the present invention provides compounds of Formula (I):

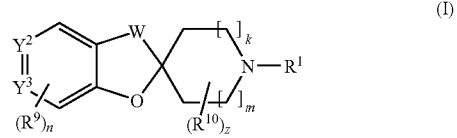

(I)

or a stereoisomeric form, mixtures of stereoisomeric forms, or pharmaceutically acceptable salt forms thereof,
wherein:
$R^1$ is H, $C_1$-$C_4$ alkyl, or $C_3$-$C_5$ cycloalkyl;
W is —$CH_2$—, —$CH_2CH_2$—, or —$CH_2$—O—;
k is 0, 1, or 2; m is 0, 1, or 2; and the sum of m and k is 1, 2, or 3;
$Y^2$=$Y^3$ is —C(X)=CH— or —CH=C(X)—;

X is $R^2$, —$OR^2$, —($C_1$-$C_3$ alkyl)-$R^2$, —O—($C_1$-$C_3$ alkyl)-$R^2$, —$NHR^2$, —NHC(=O)$R^2$, or —NHC(=O)$NHR^2$;
  wherein said $C_1$-$C_3$ alkyl is optionally substituted with —OH or $C_1$-$C_4$ alkoxy;

$R^2$ is

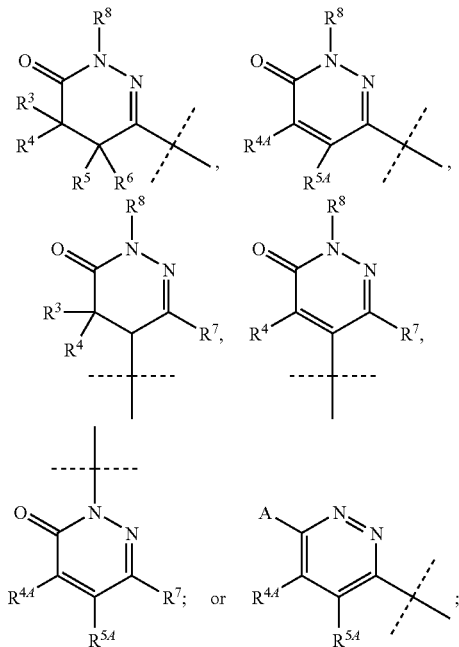

A is F, Cl, or Br;
$R^3$ is H, F, or $C_1$-$C_4$ alkyl;
$R^4$ is H, F, or $C_1$-$C_4$ alkyl;
$R^{4A}$ is H, F, Cl, Br, or $C_1$-$C_4$ alkyl;
$R^5$ is H, F, or $C_1$-$C_4$ alkyl;
$R^{5A}$ is H, F, Cl, Br, $C_1$-$C_4$ alkyl or phenyl;
alternatively, $R^4$ and $R^5$, together with the carbon atoms to which they are attached, may form a fused $C_3$-$C_6$ cycloalkyl ring optionally substituted with, 1, 2, or 3 $R^{14}$;
alternatively, $R^{4A}$ and $R^{5A}$, together with the carbon atoms to which they are attached, may form
  a fused phenyl ring optionally substituted with 1, 2, or 3 $R^{14}$;
  a $C_3$-$C_6$ cycloalkyl ring optionally substituted with 1, 2 or 3 $R^{14}$;
  a 5 to 6 membered fused heteroaryl ring system containing one, two, or three heteroatoms selected from N, O, and S, wherein said heteroaryl ring system is optionally substituted with 1, 2, or 3 $R^{14}$; or
  a 5 to 6 membered fused heterocycloalkyl ring system containing one, two, or three heteroatoms selected from N, O, S, SO, and $SO_2$, wherein said heterocycloalkyl ring system is optionally substituted with 1, 2, or 3 $R^{14}$;
$R^6$ is H, F, or $C_1$-$C_4$ alkyl;
$R^7$ is H, F, Cl, Br, or $C_1$-$C_4$ alkyl;
$R^8$ is H, —C(=O)$R^{27}$, —$CO_2R^{27}$, $C_1$-$C_6$ alkyl optionally substituted by 1-3 $R^{20}$;
  $C_3$-$C_8$ cycloalkyl optionally substituted by 1-3 $R^{20A}$;
  $C_6$-$C_{10}$ aryl optionally substituted by 1-3 $R^{20A}$;
  $C_7$-$C_{15}$ arylalkyl optionally substituted by 1-3 $R^{20A}$; or
  a 5 to 10 membered heteroaryl ring system containing one, two, or three heteroatoms selected from N, O, and S, wherein said heteroaryl ring system is optionally substituted with 1-3 $R^{20A}$;

$R^9$, at each occurrence, is independently F, Cl, Br, $C_1$-$C_4$ alkyl, or $C_1$-$C_4$ alkoxy;
$R^{10}$ is F, Cl, Br, $C_1$-$C_3$ alkyl, or $C_1$-$C_3$ alkoxy;
$R^{14}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(=O)$OR^{21}$, —OC(=O)$NR^{23}R^{24}$, —$NR^{27}$C(=S)$R^{21}$, —$SR^{21}$, —S(O)$R^{21}$, or —S(O)$_2R^{21}$; $C_1$-$C_6$ alkyl optionally substituted with $OR^{26}$; $C_2$-$C_6$ alkenyl, or $C_2$-$C_6$ alkynyl;
$R^{20}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(=O)$OR^{21}$, —OC(=O)$NR^{23}R^{24}$, —$NR^{27}$C(=S)$R^{21}$, —$SR^{21}$, —S(O)$R^{21}$, or —S(O)$_2R^{21}$; $C_1$-$C_6$ alkyl optionally substituted with $OR^{26}$; $C_2$-$C_6$ alkenyl, $C_2$-$C_6$ alkynyl, $C_3$-$C_7$ cycloalkyl, phenyl, 3- to 7-membered heterocycloalkyl group, or 5- or 6-membered heteroaryl group;
$R^{20A}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(=O)$OR^{21}$, —OC(=O)$NR^{23}R^{24}$, —$NR^{27}$C(=S)$R^{21}$, —$SR^{21}$, —S(O)$R^{21}$, or —S(O)$_2R^{21}$; $C_1$-$C_6$ alkyl optionally substituted with $OR^{26}$; $C_2$-$C_6$ alkenyl, or $C_2$-$C_6$ alkynyl;
$R^{21}$ at each occurrence is independently H, $C_1$-$C_6$ alkyl, $C_6$-$C_{10}$ aryl, or $C_7$-$C_{15}$ arylalkyl;
$R^{22}$ at each occurrence is independently the residue of an amino acid after the hydroxyl group of the carboxyl group is removed;
$R^{23}$ and $R^{24}$ at each occurrence is independently selected from H, $C_1$-$C_6$ alkyl, and $C_6$-$C_{10}$ aryl;
alternatively, $R^{23}$ and $R^{24}$, together with the nitrogen atom to which they are attached, form a 3 to 7 membered heterocycloalkyl ring system containing one, two, or three heteroatoms selected from N, O, and S, wherein said heterocycloalkyl ring system is optionally substituted with =O;
$R^{26}$ is H or $C_1$-$C_6$ alkyl;
$R^{27}$ is H or $C_1$-$C_6$ alkyl;
n is 0, 1, 2, or 3; and
z is 0, 1, 2, 3, 4, 5, or 6.

In preferred embodiments, the present invention provides novel compounds of Formula (I):

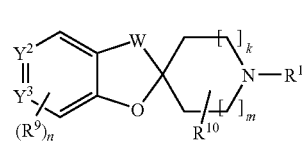

(I)

and stereoisomeric forms, mixtures of stereoisomeric forms or pharmaceutically acceptable salt forms thereof, wherein:
$R^1$ is H, $C_1$-$C_4$ alkyl, or $C_3$-$C_8$ cycloalkyl;
W is —$CH_2$—, —$CH_2CH_2$—, or —$CH_2$—O—;
k is 0, 1, or 2; m is 0, 1, or 2; and the sum of m and k is 1, 2, or 3;
$Y^2$=$Y^3$ is —C(X)=CH— or —CH=C(X)—;
X is $R^2$, —$OR^2$, —($C_1$-$C_3$ alkyl)-$R^2$, —O—($C_1$-$C_3$ alkyl)-$R^2$, —$NHR^2$, —NHC(=O)$R^2$, or —NHC(=O)$NHR^2$;

$R^2$ is

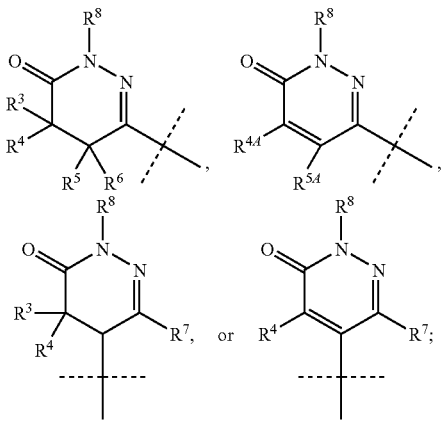

$R^3$ is H, F, or $C_1$-$C_4$ alkyl;
$R^4$ is H, F, or $C_1$-$C_4$ alkyl;
$R^{4A}$ is H, F, Cl, Br, or $C_1$-$C_4$ alkyl;
$R^5$ is H, F, or $C_1$-$C_4$ alkyl;
$R^{5A}$ is H, F, Cl, Br, or $C_1$-$C_4$ alkyl;
alternatively, $R^4$ and $R^5$, together with the carbon atoms to which they are attached, may form a fused $C_3$-$C_6$ cycloalkyl ring optionally substituted with 1-3 $R^{14}$;
alternatively, $R^{4A}$ and $R^{5A}$, together with the carbon atoms to which they are attached, may form
  a fused phenyl ring optionally substituted with 1-3 $R^{14}$;
  $C_3$-$C_6$ cycloalkyl ring optionally substituted with 1-3 $R^{14}$;
  a 5 to 6 membered fused heteroaryl ring system containing one, two, or three heteroatoms selected from N, O, and S, wherein said heteroaryl ring system is optionally substituted with 1-3 $R^{14}$; or
  5 to 6 membered fused heterocycloalkyl ring system containing one, two, or three heteroatoms selected from N, O, S, SO, and $SO_2$, wherein said heterocycloalkyl ring system is optionally substituted with 1-3 $R^{14}$;
$R^6$ is H, F, or $C_1$-$C_4$ alkyl;
$R^7$ is H, F, Cl, Br, or $C_1$-$C_4$ alkyl;
$R^8$ is H, —C(=O)$R^{27}$, —CO$_2R^{27}$, $C_1$-$C_6$ alkyl optionally substituted by 1-3 $R^{20}$;
  $C_3$-$C_8$ cycloalkyl optionally substituted by 1-3 $R^{20A}$;
  $C_6$-$C_{10}$ aryl optionally substituted by 1-3 $R^{20A}$;
  $C_7$-$C_{15}$ arylalkyl optionally substituted by 1-3 $R^{20A}$; and
  a 5 to 10 membered heteroaryl ring system containing one, two, or three heteroatoms selected from N, O, and S, wherein said heteroaryl ring system is optionally substituted with 1-3 $R^{20A}$;
$R^9$, at each occurrence, is independently, F, Cl, Br, $C_1$-$C_4$ alkyl, or $C_1$-$C_4$ alkoxy;
$R^{10}$ is F, Cl, $C_1$-$C_3$ alkyl, or $C_1$-$C_3$ alkoxy;
$R^{14}$ at each occurrence is independently, H, F, Cl, Br, I, —OR$^{21}$, —OR$^{22}$, —NR$^{23}$R$^{24}$, —NHOH, —NO$_2$, —CN, —CF$_3$, (=O), —C(=O)R$^{21}$, —CO$_2$R$^{21}$, —OC(=O)R$^{21}$, —C(=O)NR$^{23}$R$^{24}$, —NR$^{27}$C(=O)R$^{21}$, —NR$^{27}$C(=O)OR$^{21}$, —OC(=O)NR$^{23}$R$^{24}$, —NR$^{27}$C(=S)R$^{21}$, —SR$^{21}$, —S(O)R$^{21}$, or —S(O)$_2$R$^{21}$; $C_1$-$C_6$ alkyl optionally substituted with OR$^{26}$; $C_2$-$C_6$ alkenyl, or $C_2$-$C_6$ alkynyl;
$R^{20}$ at each occurrence is independently, H, F, Cl, Br, I, —OR$^{21}$, OR$^{22}$, —NR$^{23}$R$^{24}$, —NHOH, —NO$_2$, —CN, —CF$_3$, (=O), —C(=O)R$^{21}$, —CO$_2$R$^{21}$, —OC(=O)R$^{21}$, —C(=O)NR$^{23}$R$^{24}$, —NR$^{27}$C(=O)R$^{21}$, —NR$^{27}$C(=O)OR$^{21}$, —OC(=O)NR$^{23}$R$^{24}$, —NR$^{27}$C(=S)R$^{21}$, —SR$^{21}$, —S(O)R$^{21}$, or —S(O)$_2$R$^{21}$; $C_1$-$C_6$ alkyl optionally substituted with OR$^{26}$; $C_2$-$C_6$ alkenyl, $C_2$-$C_6$ alkynyl, $C_3$-$C_7$ cycloalkyl, phenyl, 3- to 7-membered heterocycloalkyl group, or 5- or 6-membered heteroaryl group;
$R^{20A}$ at each occurrence is independently, H, F, Cl, Br, I, —OR$^{21}$, —OR$^{22}$, —NR$^{23}$R$^{24}$, —NHOH, —NO$_2$, —CN, —CF$_3$, (=O), —C(=O)R$^{21}$, —CO$_2$R$^{21}$, —OC(=O)R$^{21}$, —C(=O)NR$^{23}$R$^{24}$, —NR$^{27}$C(=O)R$^{21}$, —NR$^{27}$C(=O)OR$^{21}$, —OC(=O)NR$^{23}$R$^{24}$, —NR$^{27}$C(=S)R$^{21}$, —SR$^{21}$, —S(O)R$^{21}$, or —S(O)$_2$R$^{21}$; $C_1$-$C_6$ alkyl optionally substituted with OR$^{26}$; $C_2$-$C_6$ alkenyl, or $C_2$-$C_6$ alkynyl;
$R^{21}$ at each occurrence is independently H, $C_1$-$C_6$ alkyl, $C_6$-$C_{10}$ aryl, or $C_7$-$C_{15}$ arylalkyl;
$R^{22}$ at each occurrence is independently the residue of an amino acid after the hydroxyl group of the carboxyl group is removed;
$R^{23}$ and $R^{24}$ at each occurrence is independently selected from H, $C_1$-$C_6$ alkyl, and $C_6$-$C_{10}$ aryl;
alternatively, $R^{23}$ and $R^{24}$, together with the nitrogen atom to which they are attached, form a 3 to 7 membered heterocycloalkyl ring system containing one, two, or three heteroatoms selected from N, O, and S, wherein said heterocycloalkyl ring system is optionally substituted with =O;
$R^{26}$ is H or $C_1$-$C_6$ alkyl;
$R^{27}$ is H or $C_1$-$C_6$ alkyl; and
n is 0, 1, 2, or 3.

In preferred embodiments, the present invention provides compounds wherein $R^1$ is $C_3$-$C_8$ cycloalkyl.

In preferred embodiments, the present invention provides compounds wherein $R^1$ is cyclobutyl or cyclopentyl.

In preferred embodiments, the present invention provides compounds wherein W is —CH$_2$— or —CH$_2$—CH$_2$—.

In preferred embodiments, the present invention provides compounds wherein $R^2$ is

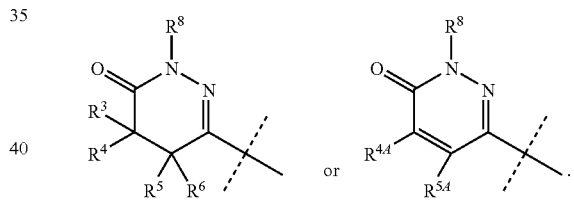

In preferred embodiments, the present invention provides compounds wherein $R^4$ and $R^5$, together with the carbon atoms to which they are attached, form a fused cyclopropyl or cyclobutyl ring.

In preferred embodiments, the present invention provides compounds wherein $R^{4A}$ and $R^{5A}$, together with the carbon atoms to which they are attached, form a fused phenyl, thienyl, pyrrolyl, oxazolyl, pyridinyl, cyclopropyl, cyclobutyl, cyclopentyl, or cyclohexyl ring.

Preferred embodiments of the present invention include those wherein k is 1. Other embodiments include those wherein m is 1. Still other embodiments include those wherein the sum of m and k is 2.

Also preferred within the present invention are those compounds wherein $Y^2$=$Y^3$ is —C(X)=CH—. Also preferred are those compounds wherein X is $R^2$. In other preferred compounds of the invention, X is —OR$^2$.

In some embodiments of the present invention, $R^8$ is H. In other embodiments, $R^8$ is $C_1$-$C_6$ alkyl optionally substituted by 1-3 $R^{20}$. In other embodiments, $R^8$ is $C_1$-$C_6$ alkyl.

In certain preferred embodiments, $R^9$ is $C_1$-$C_4$ alkyl.

In some embodiments of the invention, n is 0. In other embodiments, it is preferred that n is 1. In other embodiments, z is preferably 0.

In a preferred embodiment, the present invention provides compounds of Formula (II):

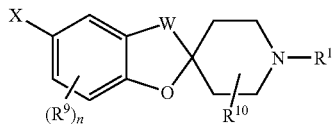

and stereoisomeric forms, mixtures of stereoisomeric forms or pharmaceutically acceptable salt forms thereof, wherein:
$R^1$ is $C_3$-$C_5$ cycloalkyl;
W is —$CH_2$— or —$CH_2$—$CH_2$—;
X is $R^2$, —$OR^2$, or —$NHR^2$;
$R^2$ is

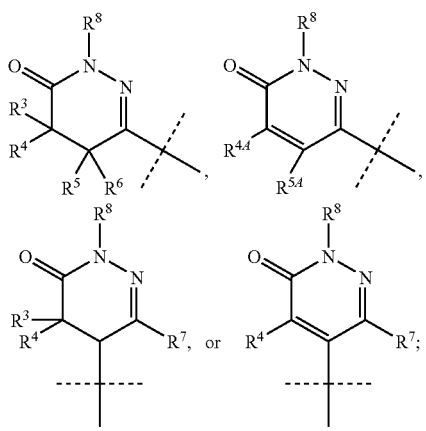

$R^3$ is H or $C_1$-$C_4$ alkyl;
$R^4$ is H or $C_1$-$C_4$ alkyl;
$R^{4A}$ is H or $C_1$-$C_4$ alkyl;
$R^5$ is H or $C_1$-$C_4$ alkyl;
$R^{5A}$ is H or $C_1$-$C_4$ alkyl;
alternatively, $R^4$ and $R^5$, together with the carbon atoms to which they are attached, may form a fused $C_3$-$C_6$ cycloalkyl ring optionally substituted with 1-3 $R^{14}$;
alternatively, $R^{4A}$ and $R^{5A}$, together with the carbon atoms to which they are attached, may form
  a fused phenyl ring optionally substituted with 1-3 $R^{14}$;
  $C_3$-$C_6$ cycloalkyl ring optionally substituted with 1-3 $R^{14}$;
  a 5 to 6 membered fused heteroaryl ring system containing one, two, or three heteroatoms selected from N, O, and S, wherein said heteroaryl ring system is optionally substituted with 1-3 $R^{14}$; or
  5 to 6 membered fused heterocycloalkyl ring system containing one, two, or three heteroatoms selected from N, O, S, SO, and $SO_2$, wherein said heterocycloalkyl ring system is optionally substituted with 1-3 $R^{14}$;
$R^6$ is H or $C_1$-$C_4$ alkyl;
$R^7$ is H or $C_1$-$C_4$ alkyl;
$R^8$ is H, —C(=O)$R^{27}$, —$CO_2R^{27}$, $C_1$-$C_6$ alkyl optionally substituted by 1-3 $R^{20}$;
  $C_3$-$C_8$ cycloalkyl optionally substituted by 1-3 $R^{20A}$;
  $C_6$-$C_{10}$ aryl optionally substituted by 1-3 $R^{20A}$;
  $C_7$-$C_{15}$ arylalkyl optionally substituted by 1-3 $R^{20A}$; and
  a 5 to 10 membered heteroaryl ring system containing one, two, or three heteroatoms selected from N, O, and S, wherein said heteroaryl ring system is optionally substituted with 1-3 $R^{20A}$;

$R^9$, at each occurrence, is independently, F, Cl, Br, $C_1$-$C_4$ alkyl, or $C_1$-$C_4$ alkoxy;
$R^{10}$ is F, Cl, $C_1$-$C_3$ alkyl, or $C_1$-$C_3$ alkoxy;
$R^{14}$ at each occurrence is independently, H, F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —C(=O)$NR^{23}R^{24}$, —$NR^{24}$C(=O)$R^{21}$, —$NR^{27}$C(=O)$OR^{21}$, —OC(=O)$NR^{23}R^{24}$, —$NR^{27}$C(=S)$R^{21}$, $SR^{21}$, —S(O)$R^{21}$, or —$S(O)_2R^{21}$; $C_1$-$C_6$ alkyl optionally substituted with $OR^{26}$; $C_2$-$C_6$ alkenyl, or $C_2$-$C_6$ alkynyl;
$R^{20}$ at each occurrence is independently, H, F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(=O)$OR^{21}$, —OC(=O)$NR^{23}R^{24}$, —$NR^{27}$C(=S)$R^{21}$, —$SR^{21}$, —S(O)$R^{21}$, or —$S(O)_2R^{21}$; $C_1$-$C_6$ alkyl optionally substituted with $OR^{26}$; $C_2$-$C_6$ alkenyl, $C_2$-$C_6$ alkynyl, $C_3$-$C_7$ cycloalkyl, phenyl, 3- to 7-membered heterocycloalkyl group, or 5- or 6-membered heteroaryl group;
$R^{20A}$ at each occurrence is independently, H, F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}$C(=O)$R^{21}$, —$NR^{27}$C(=O)$OR^{21}$, —OC(=O)$NR^{23}R^{24}$, —$NR^{27}$C(=S)$R^{21}$, —$SR^{21}$, —S(O)$R^{21}$, or —$S(O)_2R^{21}$; $C_1$-$C_6$ alkyl optionally substituted with $OR^{26}$; $C_2$-$C_6$ alkenyl, or $C_2$-$C_6$ alkynyl;
$R^{21}$ at each occurrence is independently H, $C_1$-$C_6$ alkyl, $C_6$-$C_{10}$ aryl, or $C_7$-$C_{15}$ arylalkyl;
$R^{22}$ at each occurrence is independently the residue of an amino acid after the hydroxyl group of the carboxyl group is removed;
$R^{23}$ and $R^{24}$ at each occurrence is independently selected from H, $C_1$-$C_6$ alkyl, and $C_6$-$C_{10}$ aryl;
alternatively, $R^{23}$ and $R^{24}$, together with the nitrogen atom to which they are attached, form a 3 to 7 membered heterocycloalkyl ring system containing one, two, or three heteroatoms selected from N, O, and S, wherein said heterocycloalkyl ring system is optionally substituted with =O;
$R^{26}$ is H or $C_1$-$C_6$ alkyl;
$R^{27}$ is H or $C_1$-$C_6$ alkyl; and
n is 0, 1, 2, or 3.

In preferred embodiments, the present invention provides compounds wherein $R^1$ is cyclobutyl or cyclopentyl.

In preferred embodiments, the present invention provides compounds wherein $R^2$ is

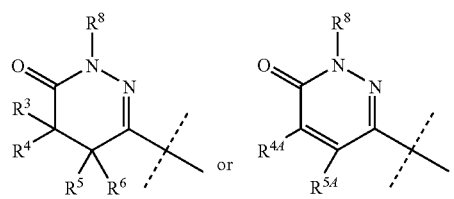

In preferred embodiments, the present invention provides compounds wherein $R^4$ and $R^5$, together with the carbon atoms to which they are attached, form a fused cyclopropyl or cyclobutyl ring.

In preferred embodiments, the present invention provides compounds wherein $R^{4A}$ and $R^{5A}$, together with the carbon atoms to which they are attached, form a fused phenyl, thienyl, pyrrolyl, oxazolyl, pyridinyl, cyclopropyl, cyclobutyl, cyclopentyl, or cyclohexyl ring.

In preferred embodiments, the present invention provides compounds wherein $R^8$ is H.

In preferred embodiments, the present invention provides compounds of Formula (III):

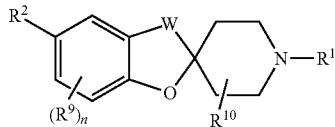

and stereoisomeric forms, mixtures of stereoisomeric forms or pharmaceutically acceptable salt forms thereof, wherein:
$R^1$ is $C_3$-$C_6$ cycloalkyl;
W is —$CH_2$— or —$CH_2$—$CH_2$—;
$R^2$ is

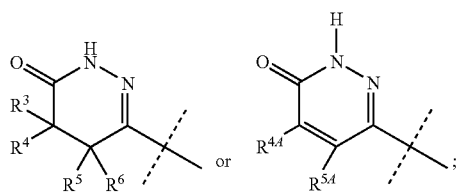

$R^3$ is H, methyl, or ethyl;
$R^4$ is H, methyl, or ethyl;
$R^{4A}$ is H, methyl, or ethyl;
$R^5$ is H, methyl, or ethyl;
$R^{5A}$ is H, methyl, or ethyl;
alternatively, $R^4$ and $R^5$, together with the carbon atoms to which they are attached, may form a fused $C_3$-$C_6$ cycloalkyl ring;
alternatively, $R^{4A}$ and $R^{5A}$, together with the carbon atoms to which they are attached, may form
a fused phenyl ring;
$C_3$-$C_6$ cycloalkyl ring;
a 5 to 6 membered fused heteroaryl ring system containing one, two, or three heteroatoms selected from N, O, and S; or
5 to 6 membered fused heterocycloalkyl ring system containing one, two, or three heteroatoms selected from N, O, S, SO, and $SO_2$;
$R^6$ is H, methyl, or ethyl;
$R^7$ is H, methyl, or ethyl;
$R^9$, at each occurrence, is independently, F, Cl, methyl, ethyl, methoxy, or ethoxy;
$R^{10}$ is F, Cl, methyl, ethyl, methoxy, or ethoxy; and
n is 0, 1, or 2.
In a preferred embodiment, the present invention provides compounds of Formula (III):

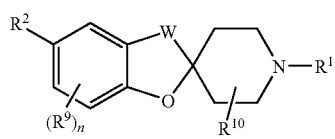

and stereoisomeric forms, mixtures of stereoisomeric forms or pharmaceutically acceptable salt forms thereof, wherein:
$R^1$ is cyclobutyl or cyclopentyl;
W is —$CH_2$— or —$CH_2$—$CH_2$—;
$R^2$ is

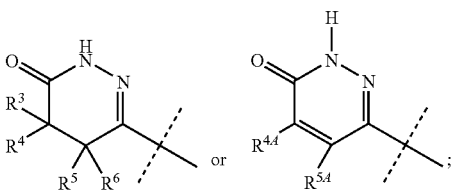

$R^3$ is H, methyl, or ethyl;
$R^4$ is H, methyl, or ethyl;
$R^{4A}$ is H, methyl, or ethyl;
$R^5$ is H, methyl, or ethyl;
$R^{5A}$ is H, methyl, or ethyl;
alternatively, $R^4$ and $R^5$, together with the carbon atoms to which they are attached, may form a fused cyclopropyl, cyclobutyl, or cyclopentyl ring;
alternatively, $R^{4A}$ and $R^{5A}$, together with the carbon atoms to which they are attached, may form a fused phenyl, thienyl, pyrrolyl, oxazolyl, pyridinyl, cyclopropyl, cyclobutyl, cyclopentyl, or cyclohexyl ring;
$R^6$ is H, methyl, or ethyl;
$R^7$ is H, methyl, or ethyl;
$R^9$, at each occurrence, is independently, F, Cl, methyl, ethyl, methoxy, or ethoxy;
$R^{10}$ is F, Cl, methyl, ethyl, methoxy, or ethoxy; and
n is 0, 1, or 2.
In a preferred embodiment, the present invention provides compounds wherein $R^2$ is

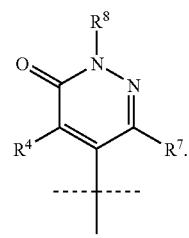

In another embodiment, the present invention provides pharmaceutical compositions comprising a compound according to the present invention and one or more pharmaceutically acceptable excipients.

In a further embodiment the present invention provides for a method for treating a disorder selected from the group consisting of narcolepsy or sleep/wake disorders, feeding behavior disorders, eating disorders, obesity, cognition disorders, arousal disorders, memory disorders, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction comprising administering to a subject in need of such treatment a therapeutically effective amount of a compound of the present invention. In a preferred embodiment the present invention provides for a method of treating narcolepsy or sleep/wake disorders. In a preferred embodiment the present invention provides for a method of treating attention deficit hyperactivity disorder. In a preferred embodiment the present invention provides for a method of treating cognition disorders.

In another embodiment the present invention provides for use of the compounds of the present invention for use in therapy.

In a further embodiment the present invention provides for use of the compounds of the present invention in the manufacture of a medicament for treating a disorder selected from the group consisting of narcolepsy or sleep/wake disorders, feeding behavior disorder, eating disorders, obesity, cognition disorders, arousal disorders, memory disorders, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction comprising administering to a subject in need of such treatment a therapeutically effective amount of a compound of the present invention.

Definitions

In the formulas described and claimed herein, it is intended that when any symbol appears more than once in a particular formula or substituent, its meaning in each instance is independent of the other.

The following terms and expressions have the indicated meanings.

As used herein, the term "about" refers to a range of values from ±10% of a specified value. For example, the phrase "about 50" includes ±10% of 50, or from 45 to 55. The phrase "from about 10 to 100" includes ±10% of 10 and ±10% of 100, or from 9 to 110.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, "substituted" refers to any one or more hydrogen atoms on the indicated atom is replaced with a selected group referred to herein as a "substituent," provided that the substituted atom's valency is not exceeded, and that the substitution results in a stable compound.

Examples of preferred substitutents are —OH, alkyl, cycloalkyl, alkoxy, halogen, haloalkyl, aryl, heteroaryl, and heterocyclyl.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups has the same meaning as alkyl defined above. A designation such as "$C_1$-$C_6$ alkyl" refers to straight-chain, or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms, such as methyl, ethyl, propyl, isopropyl, butyl, isobutyl, sec-butyl, and tert-butyl. A designation such as "$C_1$-$C_3$ alkyl" refers to an alkyl radical containing from 1 to 3 carbon atoms, such as methyl, ethyl, propyl, and isopropyl. Alkyl groups can be substituted or unsubstituted. Preferred substitutents include —OH and alkoxy.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc. Alkenyl groups can be substituted or unsubstituted As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include ethynyl, propynyl, isopropynyl, 3,5-hexadiynyl, etc. Alkynyl groups can be substituted or unsubstituted.

As used herein, the term "$C_1$-$C_4$ haloalkyl" refers to an "alkyl" group as defined herein substituted by one or more halogen atoms to form a stable compound. Examples of haloalkyl, include but are not limited to, —$CF_3$, —$CHF_2$, —$CH_2F$ and $CF_2CF_3$.

As used herein, the term "$C_1$-$C_4$ alkoxy" refers to an "alkyl" group as defined herein bonded to and oxygen atom. Alkoxy groups can be substituted or unsubstituted.

As used herein, the term "halo" refers to an F, Cl, Br, and I. Preferred halo substituents are F and Cl.

As used herein, the term "arylalkyl" or "aralkyl" refers to an alkyl group that is substituted with an aryl group. A designation "$C_2$-$C_{is}$ arylalkyl" refers to an arylalkyl radical containing from 7 to 15 carbon atoms. Examples of arylalkyl groups include, but are not limited to, benzyl, phenethyl, diphenylmethyl, diphenylethyl, naphthylmethyl, etc. preferably benzyl. Arylalkyl groups can be substituted or unsubstituted.

As used herein, the term "cycloalkyl" refers to a saturated or partially saturated mono- or bicyclic alkyl ring system containing 3 to 10 carbon atoms. Certain embodiments contain 3 to 6 carbon atoms, and other embodiments contain 5 or 6 carbon atoms. A designation such as "$C_5$-$C_7$ cycloalkyl" refers to a cycloalkyl radical containing from 5 to 7 ring carbon atoms. Examples of cycloalkyl groups include such groups as cyclopropyl, cyclobutyl, cyclopentyl, cyclohexyl, cycloheptyl, cyclooctyl, pinenyl, and adamantanyl. Cycloalkyl groups can be substituted or unsubstituted As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups. Aryl groups can be substituted or unsubstituted As used herein, the terms "heterocycle", "heterocyclic" or "heterocyclyl" refer to a substituted or unsubstituted carbocyclic group in which one or more ring carbon atoms are replaced by at least one hetero atom such as —O—, —N—, or —S—. Certain embodiments include 3 to 6 membered rings, and other embodiments include 5 or 6 membered rings. The nitrogen and sulfur heteroatoms may be optionally oxidized, and the nitrogen may be optionally substituted in non-aromatic rings. Heterocycles are intended to include heteroaryl and heterocycloalkyl groups. Heterocyclic groups can be substituted or unsubstituted.

As used herein, the term "heteroaryl" refers to an aromatic group or ring system containing 5 to 10 ring carbon atoms in which one or more ring carbon atoms are replaced by at least one hetero atom such as O, N, or S. Certain embodiments include 5 or 6 membered rings. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, imidazopyridinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzooxadiazolyl, benzisoxazolyl, cinnolinyl, phthalazinyl, naphthyridinyl, and quinoxalinyl. Heteroaryl groups can be substituted or unsubstituted.

As used herein, the term "heterocycloalkyl" refers to a cycloalkyl group in which one or more ring carbon atoms are replaced by at least one hetero atom such as O, N, S, SO, and $SO_2$. Certain embodiments include 3 to 6 membered rings, and other embodiments include 5 or 6 membered rings. Examples of heterocycloalkyl groups include azetidinyl, pyrrolidinyl, pyrrolinyl, imidazolidinyl, imidazolinyl, oxazolidinyl, pirazolidinyl, pirazolinyl, pyrazalinyl, piperidyl, piperazinyl, hexahydropyrimidinyl, morpholinyl, thiomorpholinyl, dihydrobenzofuranyl, tetrahydrofuranyl, tetrahydropyranyl, dihydro-oxazolyl, dithiolyl, oxathiolyl, dioxazolyl, oxathiazolyl, pyranyl, oxazinyl, oxathiazinyl, and oxadiazinyl. Included within the definition of "heterocycloalkyl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene. Heterocycloalkyl groups can be substituted or unsubstituted.

As used herein, the term "pyridazin-3-one moiety" refers to a 6 to 10 membered heterocycloalkyl ring system containing a pyridazin-3-one group and optionally a second fused ring. The second fused ring, if present, is optionally a substituted or unsubstituted phenyl ring, a substituted or unsubstituted $C_3$-$C_6$ cycloalkyl ring, a substituted or unsubstituted 5 to 6 membered fused heteroaryl ring system containing one, two, or three heteroatoms selected from N, O, and S, or a a substituted or unsubstituted 5 to 6 membered fused heterocycloalkyl ring system containing one, two, or three heteroatoms selected from N, O, and S. Examples of a second fused ring include, but are not limited to, phenyl, thienyl, pyrrolyl, oxazolyl, pyridinyl, cyclopropyl, cyclobutyl, cyclopentyl, and cyclohexyl.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc. Arylalkyl groups can be substituted or unsubstituted.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-$NH_2$. The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, $2^{nd}$ ed.; Worth Publishers: New York, 1975; 71-77, the disclosure of which is incorporated herein by reference. Non-naturally occurring amino acids also include α-amino acids wherein the side chains are replaced with synthetic derivatives. In certain embodiments, substituent groups for the compounds of the present invention include the residue of an amino acid after removal of the hydroxyl moiety of the carboxyl group thereof; i.e., groups of formula —C(=O)CH (side chain)-$NH_2$. Representative side chains of naturally occurring and non-naturally occurring α-amino acids include are shown below in Table A.

TABLE A

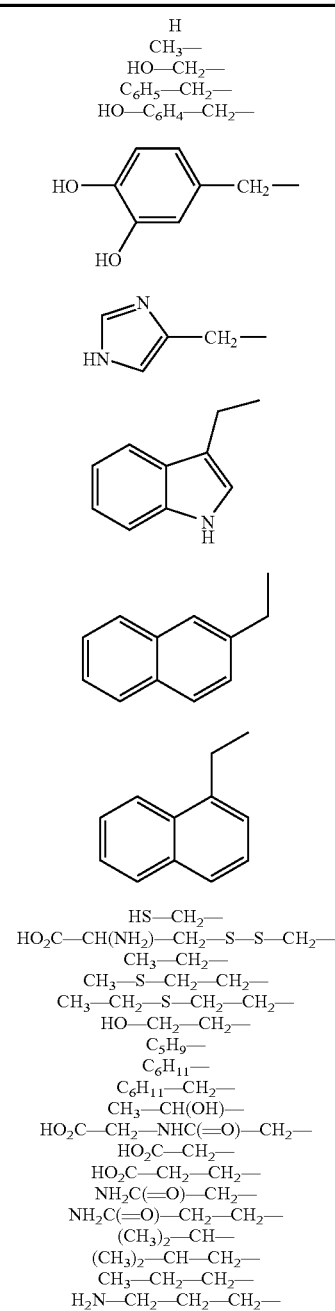

TABLE A-continued

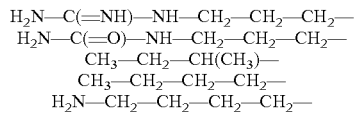

As used herein, the term "subject" refers to a warm blooded animal such as a mammal, preferably a human, or a human child, which is afflicted with, or has the potential to be afflicted with, one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. Pharmaceutically acceptable compounds, materials, compositions, and/or dosage forms should be on the Generally Recognized as Safe (GRAS) list.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

Scheme 1

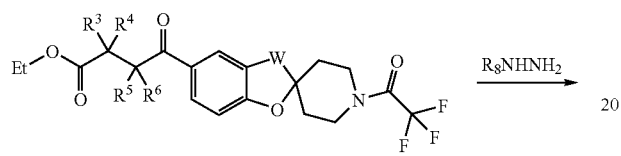

A

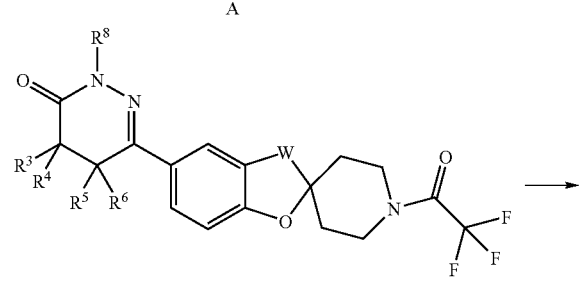

B

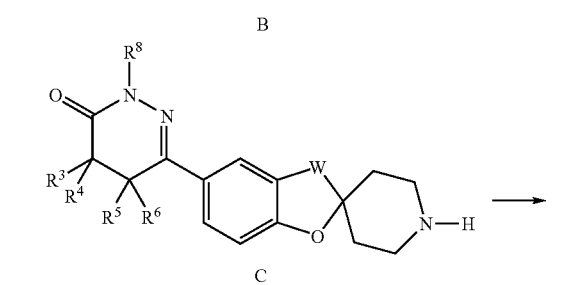

C

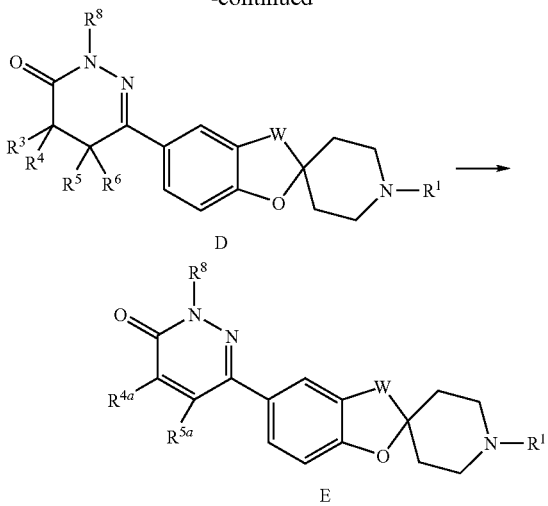

D

E

Condensation of an 4-oxobutyric acid or ester intermediate of general structure A, or a derivative there of, with hydrazine or an $R^8$ N-substituted hydrazine derivative in a solvent such as ethanol or 2-propanol provided a route to 4,5-dihydropyridazinone of general structure B. Keto-acid intermediates with substitution at the 4- and 5-position are known and may be readily prepared. Pyridazinones with $R^{3/4a}$ and $R^{5/5a}$ fused with heteroaryl or cycloalkyl groups are synthesized from the corresponding anhydrides or acid-esters. In cases where $R^1$ is a protecting group, deprotection gives $R^1$=H compounds of general structure C. Standard transformations of NH III by alkylation or reductive amination reactions produce examples of general structure D. The 4,5-dihydropyridazinones structure D may be oxidized to an aromatic pyridazinone of general structure E using $MnO_2$, $CuCl_2$, DDQ, selenium oxide, DMSO/base or sodium 3-nitrobenzenesulfonate in the presence of sodium hydroxide. NH($R^8$=H) pyridazinones may be alkylated with alkyl or substituted alkyl groups using an $R^8$-halide, a base, for example $K_2CO_3$, $Cs_2CO_3$ or NaH, in an inert solvent such as DMF, THF or $CH_3CN$. Examples wherein $R^8$ is H may be converted to analogs wherein $R^8$ is aryl or heteroaryl by standard palladium or copper coupling reactions using the appropriate aryl or heteroaryl halide.

Scheme 2

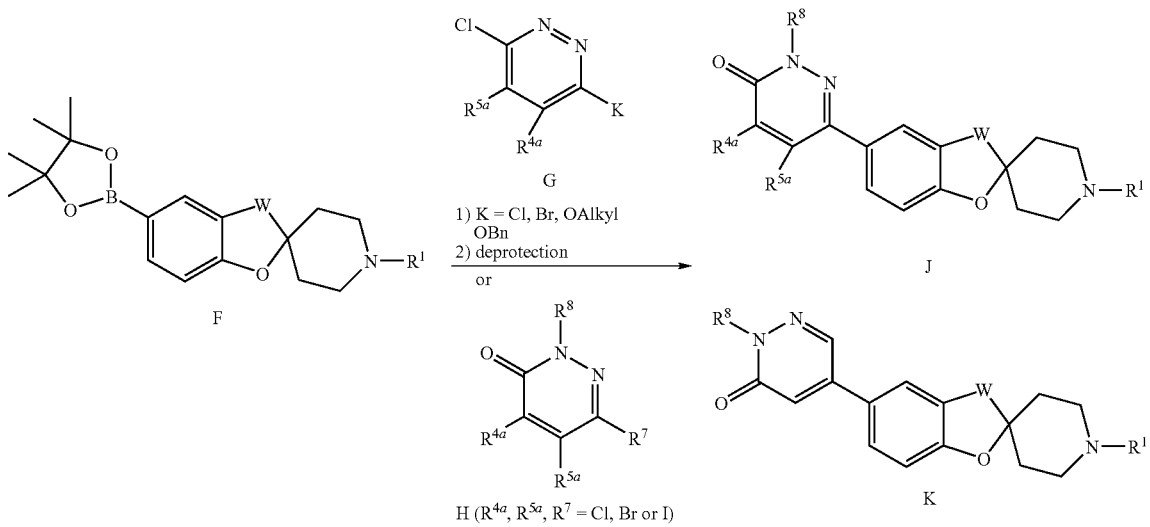

Aryl pyridazinone examples of the invention may also be synthesized using standard Suzuki cross-coupling chemistry. A spiro boron ether derivatives of general structure F, is subjected to a palladium catalyzed cross-coupling reaction (Suzuki reaction) with a pyridazine derivative of general structure G or a pyridazinone of structure H wherein the $R^{4a}$, $R^{5a}$ or $R^7$ group may be a halogen, preferably Br or I to produce examples of general structure J and K.

Spiro-pyrrolidine, -azepine and -3-piperidine examples of the invention may be synthesized using methods outlined in for the spiro-4-piperidine examples starting with N-Boc-3-pyrrolidinone, N-Boc-hexahydro-1H-azepin-4-one or N-Boc-3-piperidone, respectively, in place of N-Boc-4-piperidone.

EXAMPLES

Other features of the invention will become apparent in the course of the following descriptions of exemplary embodiments as shown below. These examples are given for illustration of the invention and are not intended to be limiting thereof.

Example 1

6-(1-Cyclobutyl-spiro[benzofuran-2(3H),4'-piperidine]-5-yl)-4,5-dihydro-2H-pyridazin-3-one

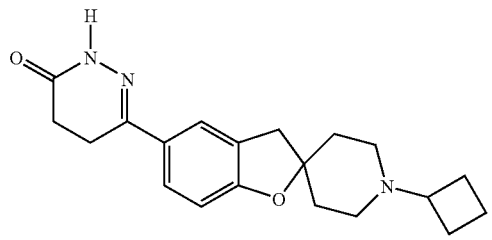 [SMILES: O=C1CCC(c2ccc3c(c2)CC2(CCN(C4CCC4)CC2)O3)=NN1]

Step 1: Synthesis of 1'-Trifluoroacetyl-spiro[benzofuran-2(3H)-4'-piperidine]

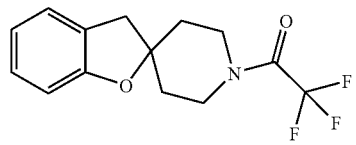 [SMILES: O=C(N1CCC2(CC1)Cc1ccccc1O2)C(F)(F)F]

A solution of spiro[benzofuran-2(3H)-4'-piperidine] (8 g, 40 mmol) in methylene chloride (70 mL) was treated with pyridine (8 mL, 100 mmol) and trifluoroacetic anhydride (7 mL, 50 mmol) at 10° C. The mixture was stirred at 10° C. for 2 h, then quenched with 1N HCl and extracted twice with methylene chloride. The combined organic layer was dried ($Na_2SO_4$), filtered, and concentrated to produce 1'-trifluoroacetyl-spiro[benzofuran-2(3H)-4'-piperidine] (10.86 g, 91%), MS m/z=286 (M+H).

Step 2: Synthesis of 1'-Trifluoroacetyl-5-(4-oxo-butyric acid ethyl ester)-spiro[benzofuran-2(3H), 4'-piperidine]

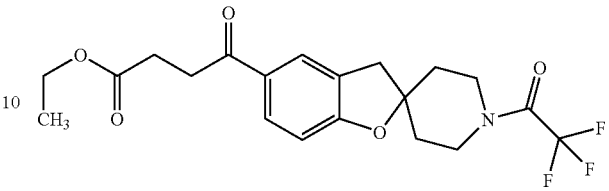

A mixture of the product from step 1 (0.51 g, 1.8 mmol) and ethyl succinyl chloride (0.25 mL, 1.8 mmol) in methylene chloride (2 mL) was cooled to 0° C. Tin tetrachloride (1M solution in methylene chloride) (2.32 mL, 2.32 mmol) was added at 10° C., stirred for 30 min then quenched with aqueous 2N HCl at 0° C. The aqueous layer was extracted twice with methylene chloride and the combined organic layer was washed with brine, dried ($Na_2SO_4$), filtered, and concentrated. The product was purified by ISCO silica gel chromatography (40 g column) using 20% EtOAc in hexane to furnish 1'-trifluoroacetyl-5-(4-oxo-butyric acid ethyl ester)-spiro[benzofuran-2(3H), 4'-piperidine] (0.61 g, 83%), MS m/z=414 (M+H).

Step 3: Synthesis of 6-(Spiro[benzofuran-2(3H), 4'-piperidine]-5-yl)-4,5-dihydro-2H-pyridazin-3-one

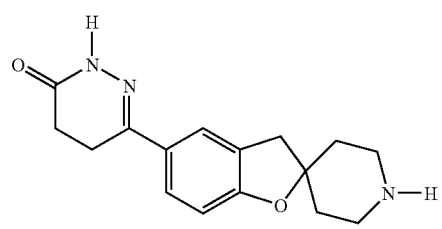 [SMILES: O=C1CCC(c2ccc3c(c2)CC2(CCNCC2)O3)=NN1]

A mixture of the product from step 2 (0.61 g, 1.5 mmol) and hydrazine monohydrate (0.57 mL, 11 mmol) in isopropanol (7 mL) was heated at 110° C. for 15 h. Isopropanol was evaporated at reduced pressure and partitioned between saturated aqueous sodium bicarbonate solution and methylene chloride. The aqueous layer was extracted twice with methylene chloride and the combined organics was washed with brine, dried ($Na_2SO_4$), filtered, and concentrated to provide 6-(spiro[benzofuran-2(3H), 4'-piperidine]-5-yl)-4,5-dihydro-2H-pyridazin-3-one (0.4 g, 95%), MS m/z=286 (M+H). The crude material was used for the next reaction without further purification.

Step 4: Synthesis of 6-(1-Cyclobutyl-spiro[benzofuran-2(3H), 4'-piperidine]-5-yl)-4,5-dihydro-2H-pyridazin-3-one

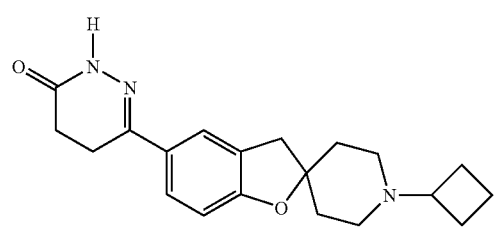 [SMILES: O=C1CCC(c2ccc3c(c2)CC2(CCN(C4CCC4)CC2)O3)=NN1]

A solution of the product from step 3 (0.4 g, 1.4 mmol) in a mixture of DMF (2 mL) and MeOH (10 mL) was stirred under argon. Cyclobutanone (0.42 mL, 6.4 mmol), sodium cyanoborohydride (0.35 g, 5.6 mmol) and acetic acid (0.2 mL, 3.17 mmol) were added sequentially and stirred at 60° C. for 15 h. The reaction mixture was concentrated at reduced pressure and partitioned between aqueous 1M sodium carbonate solution and methylene chloride. The aqueous layer was extracted twice with methylene chloride and the combined organics was washed with brine, dried (Na$_2$SO$_4$), filtered, and concentrated to provide a crude product. The crude product was purified by ISCO (40 g column) chromatography using 5 to 10% methanol in methylene chloride to 10% methanol containing 4 mL ammonium hydroxide in methylene chloride. The recovered pure product was dissolved in methylene chloride and washed with saturated aqueous sodium bicarbonate solution, brine, dried (Na$_2$SO$_4$), filtered, and concentrated. The product was crystallized from a mixture of methylene chloride, ethanol, ether, and hexane to give example 1 (6-(1-cyclobutyl-spiro[benzofuran-2(3H), 4'-piperidine]-5-yl)-4,5-dihydro-2H-pyridazin-3-one) (94 mg, 20%, 96% purity), mp 207-209° C. (methylene chloride, ethanol, ether, and hexane), MS m/z=340 (M+H); $^1$H NMR (400 MHz, CDCl$_3$): δ 1.57-2.15 (m, 12H), 2.37-2.56 (m, 2H), 2.60 (t, J=16.16 Hz, 2H), 2.76-2.87 (m, 1H), 2.96 (t, J=16.32 Hz, 2H), 3.01 (S, 2H), 6.78 (d, J=8.33 Hz, 1H), 7.46 (d, J=8.36 Hz, 1H), 7.59 (S, 1H), 8.44 (S, 1H).

Example 2

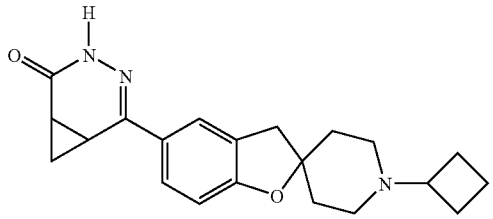 [SMILES: O=C1NN=C(c2ccc3c(c2)CC2(CCN(C4CCC4)CC2)O3)C2CC12]

This compound was prepared using the method described for Example 1 using cyclopropane dicarboxylic acid anhydride to give l'-cyclobutyl-5-(3,4-diaza-bicyclo[4.1.0]hepten-2-one-5-yl)-spiro[benzofuran-2(3H),4'-piperidine]: mp 189-191° C., MS m/z=352 (M+H); $^1$H NMR (400 MHz, CDCl$_3$): δ 0.97 (dt, J1=10.14 Hz, J2=5.31 Hz, 1H), 1.54-2.13 (m, 12H), 2.17-2.24 (m, 1H), 2.40-2.58 (m, 4H), 2.77-2.89 (m, 1H), 3.03 (s, 2H), 6.81 (d, J=8.42 Hz, 1H), 7.57 (d, J=8.50 Hz, 1H), 7.63 (s, 1H), 8.23 (s, 1H).

Example 3

6-(1-Cyclobutyl-spiro[benzofuran-2(3H),4'-piperidine]-5-yl)-5-methyl-4,5-dihydro-2H-pyridazin-3-one

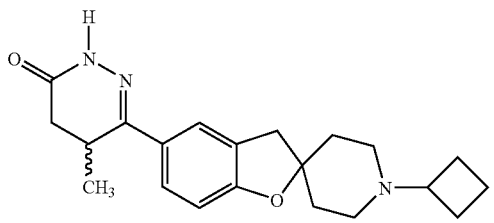 [SMILES: CC1CC(=O)NN=C1c1ccc2c(c1)CC1(CCN(C3CCC3)CC1)O2]

Step 1: Synthesis of 1'-Trifluoroacetyl-5-(propanoyl)-spiro[benzofuran-2(3H), 4'-piperidine]

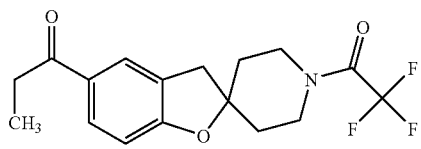 [SMILES: CCC(=O)c1ccc2c(c1)CC1(CCN(C(=O)C(F)(F)F)CC1)O2]

A mixture of 1'-trifluoroacetyl-spiro[benzofuran-2(3H)-4'-piperidine] (3.1 g, 11 mmol) and propanoyl chloride (1 mL, 10 mmol) in methylene chloride (25 mL) was cooled at 10° C. Tin tetrachloride (1M solution in methylene chloride) (14.14 mL, 14.11 mmol) was added at 10° C. and stirred at 10° C. for 30 min then quenched with aqueous 2N HCl at 0° C. The aqueous layer was extracted twice with methylene chloride and the combined organics was washed with brine, dried (Na$_2$SO$_4$), filtered, and concentrated to provide a crude product. The crude product was purified by ISCO (120 g) chromatography using 22% EtOAc in hexane to produce 1'-trifluoroacetyl-5-(propanoyl)-spiro[benzofuran-2(3H)-4'-piperidine] (2.2 g, 59%), MS m/z=342 (M+H).

Step 2: Synthesis of 1'-Trifluoroacetyl-5-(3-methyl-4-oxo-butyric acid ethyl ester)-spiro[benzofuran-2(3H), 4'-piperidine]

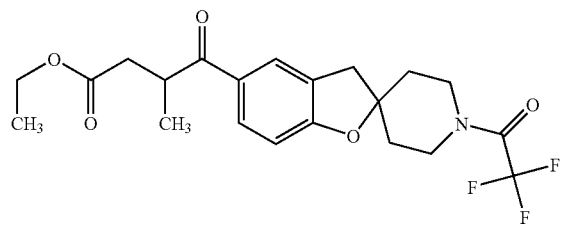 [SMILES: CCOC(=O)CC(C)C(=O)c1ccc2c(c1)CC1(CCN(C(=O)C(F)(F)F)CC1)O2]

A solution of 1'-trifluoroacetyl-5-(propanoyl)-spiro[benzofuran-2(3H), 4'-piperidine] (2.2 g, 6.45 mmol) in tetrahydrofuran (22 mL) was cooled at 0° C. Lithium diisopropylamide, (2M solution in THF) (3.56 mL, 7.09 mmol) was added dropwise and warmed to rt for 30 min. The reaction was cooled to 0° C. and ethyl bromoacetate (0.79 mL, 7.1 mmol) was added dropwise and warmed to rt for 30 min then quenched with aqueous 1M HCl acid at 0° C. The aqueous layer was extracted twice with methylene chloride and the combined organics was washed with brine, dried (Na$_2$SO$_4$), filtered, and concentrated to give a crude 1'-trifluoroacetyl-5-(3-methyl-4-oxo-butyric acid ethyl ester)-spiro[benzofuran-2(3H), 4'-piperidine] (3.34 g), MS m/z=428 (M-55).

Step 3: Synthesis of 6-(Spiro[benzofuran-2(3H), 4'-piperidine]-5-yl)-5-methyl-4,5-dihydro-2H-pyridazin-3-one

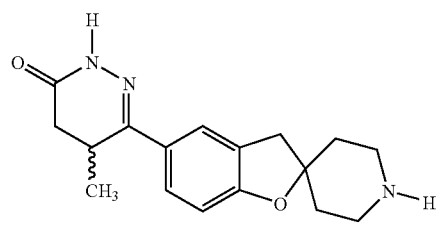 [SMILES: CC1CC(=O)NN=C1c1ccc2c(c1)CC1(CCNCC1)O2]

A mixture of 1'-trifluoroacetyl-5-(3-methyl-4-oxo-butyric acid ethyl ester)-spiro[benzofuran-2(3H), 4'-piperidine] (3.34 g, 7.8 mmol) and hydrazine monohydrate (3 mL, 60 mmol) in isopropanol (25 mL) was heated at 110° C. for 15 h. Isopropanol was evaporated at reduced pressure and partitioned between saturated aqueous sodium bicarbonate solution and methylene chloride. The aqueous layer was extracted twice with methylene chloride and the combined organics was washed with brine, dried (Na$_2$SO$_4$), filtered, and concentrated to produce a crude 6-(spiro[benzofuran-2(3H),4'-piperidine]-5-yl)-5-methyl-4,5-dihydro-2H-pyridazin-3-one (1.4 g, 60%), MS m/z=300 (M+H). The crude material was used for the next reaction without further purification.

Step 4: Synthesis of 6-(1-Cyclobutyl-spiro[benzofuran-2(3H), 4'-piperidine]-5-yl)-5-methyl-4,5-dihydro-2H-pyridazin-3-one

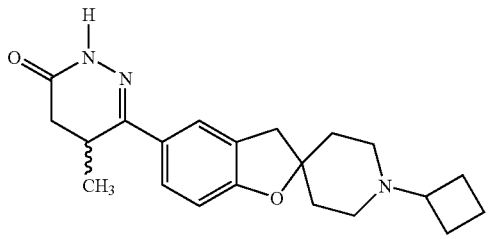 [SMILES: CC1CC(=O)NN=C1c1ccc2c(c1)CC1(CCN(C3CCC3)CC1)O2]

A solution of the product from step 3 (6-(spiro[benzofuran-2(3H), 4'-piperidine]-5-yl)-5-methyl-4,5-dihydro-2H-pyridazin-3-one) (1.4 g, 4.7 mmol) in a mixture of DMF (2 mL) and MeOH (10 mL) was stirred under argon. Cyclobutanone (1.4 mL, 19 mmol), sodium cyanoborohydride (1.2 g, 19 mmol) and acetic acid (0.65 mL, 11.36 mmol) were added sequentially and stirred at 60° C. for 13 h. The reaction mixture was concentrated at reduced pressure and partitioned between aqueous 1M sodium carbonate solution and methylene chloride. The aqueous layer was extracted twice with methylene chloride and the combined organics was washed with brine, dried (Na$_2$SO$_4$), filtered, and concentrated to provide a crude product. The crude product was purified by ISCO (120 g column) chromatography using 5 to 10% methanol in methylene chloride to obtain a pure product. The pure product was crystallized from a mixture of methylene chloride, ethanol, ether, and hexane to produce 6-(1-cyclobutyl-spiro[benzofuran-2(3H),4'-piperidine]-5-yl)-5-methyl-4,5-dihydro-2H-pyridazin-3-one (512 mg, 31%, 98% purity), mp 213-215° C. (methylene chloride, ethanol, ether, and hexane), MS m/z=354 (M+H); $^1$H NMR (400 MHz, CDCl$_3$): δ 1.25 (d, J=7.35 Hz, 3H), 1.63-2.14 (m, 10H), 2.36-2.57 (m, 4H), 2.70 (dd, J1=16.90 Hz, J2=6.78 Hz, 1H), 2.76-2.86 (m, 1H), 3.01 (s, 2H), 3.27-3.37 (m, 1H), 6.785 (d, J=8.43 Hz, 1H), 7.50 (d, J=8.47 Hz, 1H), 7.63 (s, 1H), 8.61 (s, 1H).

Example 4

6-(Cyclobutyl-spiro[benzofuran-2(3H),4'-piperidine]-5-yl)-5-methyl-2H-pyridazin-3-one

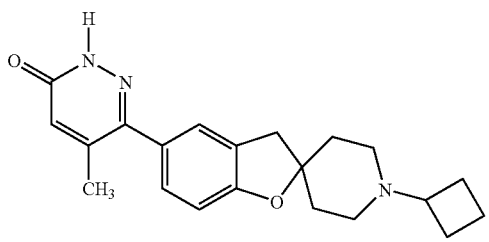 [SMILES: Cc1cc(=O)[nH]nc1-c1ccc2c(c1)CC1(CCN(C3CCC3)CC1)O2]

A mixture of 6-(1-cyclobutyl-spiro[benzofuran-2(3H),4'-piperidine]-5-yl)-5-methyl-4,5-dihydro-2H-pyridazin-3-one (202 mg, 0.57 mmol) and cesium carbonate (372 mg, 1.14 mmol) in dimethyl sulfoxide (8.5 mL) was heated at 130° C. 4 h. The mixture was cooled to RT and partitioned between water and methylene chloride. Sodium chloride was added to the mixture and the aqueous layer was extracted twice with methylene chloride. The combined organics was washed with brine, dried (Na$_2$SO$_4$), filtered, and concentrated to provide a crude product. The crude product was purified by ISCO (80 g) chromatography using 5% to 10% methanol in methylene chloride to 10% methanol containing 1% ammonium hydroxide in methylene chloride. The recovered product was dissolved in methylene chloride and washed with saturated aqueous sodium bicarbonate solution, brine, dried (Na$_2$SO$_4$), filtered, and concentrated to produce a pure product. The pure product was crystallized from a mixture of methylene chloride, methanol, ether and hexane to give example 4 (6-(cyclobutyl-spiro[benzofuran-2(3H),4'-piperidine]-5-yl)-5-methyl-2H-pyridazin-3-one) (42 mg, 21%, 96% purity), mp 243-245° C., MS m/z=352 (M+H); $^1$H NMR (400 MHz, CDCl$_3$): δ 1.55-2.97 (m, 18H), 3.05 (s, 2H), 6.80-6.86 (m, 2H), 7.14-7.19 (m, 1H), 7.21 (s, 1H), 10.55 (s, 1H).

Example 5

1'-Cyclobutyl-[6-[4,5-dihydro-2H-pyridazin-3-one-6-yl)-spiro[3,4-dihydro-benzopyran-2,4'-piperidine]

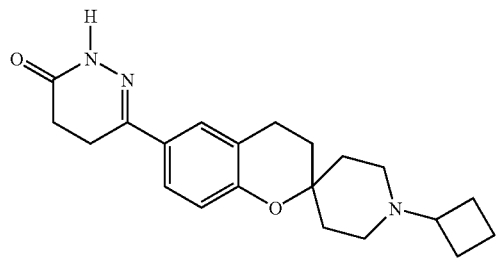

Step 1: Synthesis of 1'-Trifluoroacetyl-spiro[3,4-dihydrobenzopyran-2,4'-piperidine]

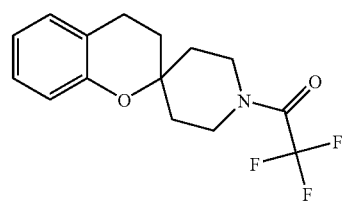 [SMILES: O=C(N1CCC2(CCc3ccccc3O2)CC1)C(F)(F)F]

A solution of 3,4-dihydrospiro[benzopyran-2,4'-piperidine].HCl (7 g, 30 mmol) in methylene chloride (60 mL) was treated with pyridine (10 mL, 100 mmol) and trifluoroacetic anhydride (4.5 mL, 32 mmol) at 10° C. The mixture was stirred at 10° C. for 3 h then quenched with 1N HCl and extracted twice with methylene chloride. The combined organics was dried (Na$_2$SO$_4$), filtered, and concentrated to produce a crude product. The crude product was purified by ISCO (330 g column) chromatography using 12 to 18% ethyl acetate in hexane to obtain a pure 1'-trifluoroacetyl-3,4-dihydrospiro[benzopyran-2,4'-piperidine] (7.48 g, 72%), MS m/z=300 (M+H).

Step 2: Synthesis of 1'-Trifluoroacetyl-6-(4-oxo-butyric acid)-spiro[3,4-dihydrobenzopyran-2,4'-piperidine]

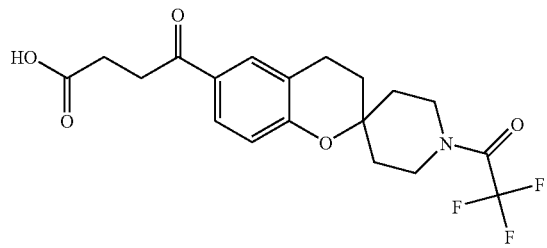 [SMILES: O=C(O)CCC(=O)c1ccc2c(c1)CCC1(CCN(C(=O)C(F)(F)F)CC1)O2]

A mixture of 1'-trifluoroacetyl-spiro[3,4-dihydrobenzopyran-2,4'-piperidine] (0.66 g, 2.20 mmol) and succinic anhydride (0.24 g, 2.43 mmol) in 1,2-dichloroethane (8 mL) was cooled to 0° C. Aluminium chloride (0.90 g, 7 mmol) was added at 0° C. and the mixture was heated at 80° C. for 16 h then quenched with aqueous 1N HCl at 0° C. The aqueous layer was extracted twice with methylene chloride and the combined organics was washed with brine, dried (Na₂SO₄), filtered, and concentrated to provide a crude 1'-trifluoroacetyl-6-(4-oxo-butyric acid)-spiro[3,4-dihydrobenzopyran-2,4'-piperidine] (0.97 g), MS m/z=400 (M+H) and 399 (M−H).

Step 3: Synthesis of 6-(4,5-Dihydro-2H-pyridazin-3-one-6-yl)-spiro[3,4-dihydrobenzopyran-2,4'-piperidine]

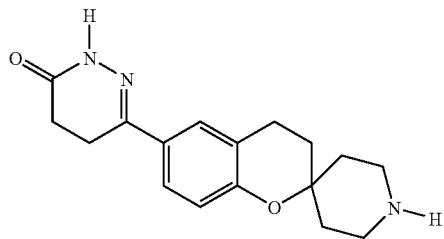 [SMILES: O=C1CCC(c2ccc3c(c2)CCC2(CCNCC2)O3)=NN1]

A mixture of 1'-trifluoroacetyl-6-(4-oxo-butyric acid)-spiro[3,4-dihydrobenzopyran-2,4'-piperidine] (0.97 g, 2.4 mmol) and hydrazine monohydrate (2.5 mL, 80 mmol) in isopropanol (12 mL) was heated at 110° C. for 19 h. Isopropanol was evaporated at reduced pressure and azeotrophed three times with benzene to produce a crude 6-(4,5-dihydro-2H-pyridazin-3-one-6-yl)-spiro[3,4-dihydrobenzopyran-2,4'-piperidine] (0.92 g), MS m/z=300 (M+H). The crude product was used for the next reaction without further purification.

Step 4: 1'-Cyclobutyl-6-(4,5-dihydro-2H-pyridazin-3-one-6-yl)-spiro[3,4-dihydrobenzopyran-2,4'-piperidine]

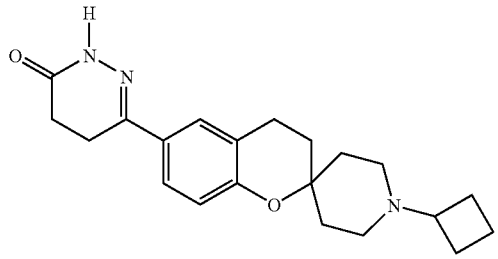 [SMILES: O=C1CCC(c2ccc3c(c2)CCC2(CCN(C4CCC4)CC2)O3)=NN1]

A solution of the product from step 3 (0.92 g, 3.10 mmol) in a mixture of DMF (2 mL) and MeOH (6 mL) was stirred under argon. Cyclobutanone (0.9 mL, 10 mmol), sodium cyanoborohydride (0.8 g, 10 mmol) and acetic acid (0.42 mL, 7.4 mmol) were added sequentially and stirred at 60° C. for 20 h. The reaction mixture was concentrated at reduced pressure and partitioned between aqueous 1M sodium carbonate solution and methylene chloride. The aqueous layer was extracted twice with methylene chloride and the combined organics was washed with brine, dried (Na₂SO₄), filtered, and concentrated to provide a crude product. The crude product was purified by ISCO (40 g column) chromatography using 4.5 to 10% methanol in methylene chloride to 10% methanol containing 4 mL of ammonium hydroxide in methylene chloride obtain a pure product. The recovered product was dissolved in methylene chloride and washed with saturated sodium bicarbonate solution, brine, dried (Na₂SO₄), filtered, and concentrated. The pure product was crystallized from a mixture of methylene chloride, ethanol, ether, and hexane to produce 1'-cyclobutyl-6-(4,5-dihydro-2H-pyridazin-3-one-6-yl)-spiro[3,4-dihydrobenzopyran-2,4'-piperidine] (39 mg, 95% purity), mp 242-243.5° C. (methylene chloride, ethanol, ether, and hexane), MS m/z=354 (M+H); $^1$H NMR (400 MHz, CDCl₃): δ 1.52-2.02 (m, 12H), 2.03-2.14 (m, 2H), 2.19-2.36 (m, 2H), 2.59 (t, J=8.49 Hz, 2H), 2.64-2.75 (m, 1H), 2.79-2.91 (m, 2H), 2.96 (t, J=7.82 Hz, 2H), 6.85-6.90 (m, 1H), 7.45-7.50 (m, 2H), 8.43 (s, 1H).

The following examples were prepared using the methods disclosed herein.

Example 6

6-(3,4-diaza-bicyclo[4.1.0]hept-4-en-2-one-5-yl)-spiro[3,4-dihydrobenzopyran-2,4'-piperidine]

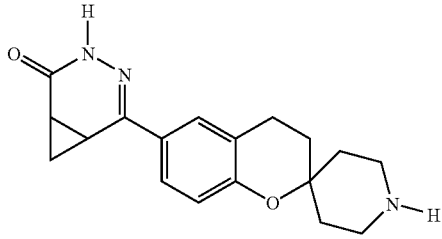 [SMILES: O=C1NN=C(c2ccc3c(c2)CCC2(CCNCC2)O3)C2CC12]

Example 6: mp 284-287° C.; MS m/z=312 (M+H); $^1$H NMR (400 MHz, DMSO): δ 0.71 (dt, J1=9.28 Hz, J2=4.71 Hz, 1H), 1.63-1.90 (m, 6H), 1.90-2.09 (m, 1H), 2.56-2.64 (m, 1H), 2.75-2.84 (m, 2H), 2.92-3.02 (m, 4H), 6.82-6.90 (m, 2H), 7.52-7.59 (m, 2H), 10.69 (s, 1H).

Example 7

1'-Cyclobutyl-6-(3,4-diaza-bicyclo[4.1.0]hept-4-en-2-one-5-yl)-spiro[3,4-dihydrobenzopyran-2,4'-piperidine]

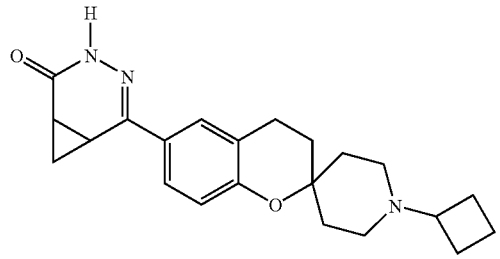

Example 7: mp 228-230° C.; MS m/z=366 (M+H); $^1$H NMR (400 MHz, CDCl₃): δ 0.96 (dt, J1=9.75 Hz, J2=4.76 Hz, 1H), 1.57-2.15 (m, 14H), 2.17-2.35 (m, 3H), 2.50-2.58 (m, 1H), 2.79-2.91 (m, 2H), 6.87-6.92 (m, 2H), 7.51-7.58 (m, 2H), 8.29 (s, 1H).

Example 8

1'-Cyclopentyl-6-(3,4-diaza-bicyclo[4.1.0]hept-4-en-2-one-5-yl)-spiro[3,4-dihydrobenzopyran-2,4'-piperidine]

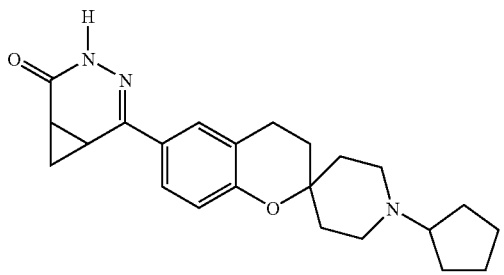 [SMILES: O=C1NN=C(c2ccc3c(c2)CCC2(CCN(C4CCCC4)CC2)O3)C2CC12]

Example 8: mp 229-231° C.; MS m/z=380 (M+H); $^1$H NMR (400 MHz, CDCl$_3$): δ 0.96 (dt, J1=9.74 Hz, J2=4.83 Hz, 1H), 1.41-1.99 (m, 16H), 2.18-2.25 (m, 1H), 2.41-2.70 (m, 4H), 2.77-2.91 (m, 3H), 6.88-6.93 (m, 1H), 7.51-7.58 (m, 2H), 8.32 (s, 1H).

Example 9

1'-Isopropyl-[6-(3,4-diaza-bicyclo[4.1.0]hept-4-en-2-one-5-yl)-spiro[3,4-dihydrobenzopyran-2,4'-piperidine]

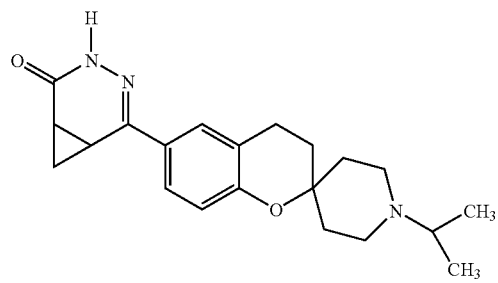 [SMILES: CC(C)N1CCC2(CCc3cc(C4=NNC(=O)C5CC45)ccc3O2)CC1]

Example 9: mp 160.6-164° C. (methylene chloride, ethanol, ether, and hexane); MS m/z=354 (M+H); $^1$H NMR (400 MHz, CDCl$_3$): δ 0.96 (dt, J1=10.14 Hz, J2=5.21 Hz, 1H), 1.10-1.22 (m, 6H), 1.74-1.95 (m, 7H), 2.17-2.26 (m, 1H), 2.50-2.92 (m, 8H), 6.88-6.93 (m, 1H), 7.51-7.59 (m, 2H), 8.31 (s, 1H).

Example 10

1'-Cyclobutyl-6-(3,4-diaza-bicyclo[4.2.0]oct-4-en-2-one-5-yl)-spiro[3,4-dihydrobenzopyran-2,4'-piperidine]

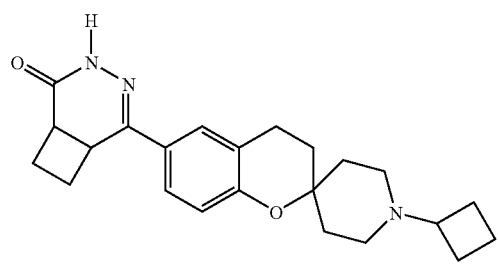 [SMILES: O=C1NN=C(c2ccc3c(c2)CCC2(CCN(C4CCC4)CC2)O3)C2CCC12]

Example 10: mp 202-204° C. (methylene chloride, ethanol, ether, and hexane); MS m/z=380 (M+H); $^1$H NMR (400 MHz, CDCl$_3$): δ 1.54-2.93 (m, 23H), 3.32-3.42 (m, 1H), 3.83-3.93 (m, 1H), 6.81-6.87 (m, 1H), 7.32-7.40 (m, 2H), 8.34 (s, 2H).

Example 11

1'-Cyclobutyl-6-(4,4-dimethyl-4,5-dihydro-2H-pyridazin-3-one-6-yl)-spiro[3,4-dihydrobenzopyran-2,4'-piperidine]

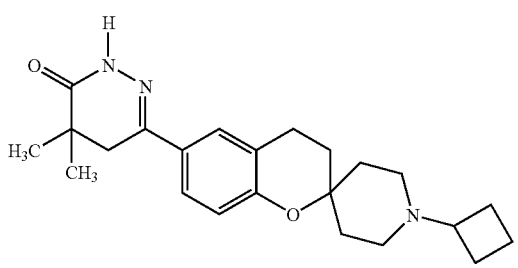 [SMILES: CC1(C)CC(c2ccc3c(c2)CCC2(CCN(C4CCC4)CC2)O3)=NNC1=O]

Example 11: mp 246-248° C. (methylene chloride, ethanol, ether, and hexane); MS m/z=382 (M+H); $^1$H NMR (400 MHz, CDCl$_3$): δ 1.25 (s, 6H), 1.62-1.93 (m, 8H), 1.95-2.16 (m, 4H), 2.24-2.39 (m, 1H), 2.65-2.95 (m, 7H), 6.83-6.90 (m, 2H), 7.43-7.52 (m, 2H), 8.44 (s, 1H).

Example 12

1'-Cyclobutyl-6-(5-methyl-4,5-dihydro-2H-pyridazin-3-one-6-yl)-spiro[3,4-dihydrobenzopyran-2,4'-piperidine]

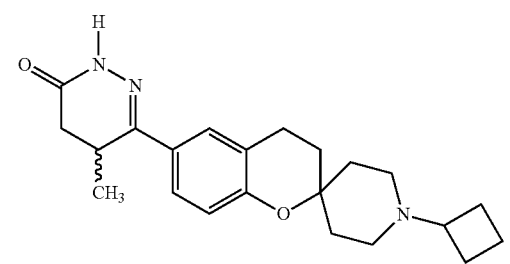 [SMILES: CC1CC(=O)NN=C1c1ccc2c(c1)CCC1(CCN(C3CCC3)CC1)O2]

Step 1: Synthesis of 1'-Trifluoroacetyl-6-(propanoyl)-spiro[3,4-dihydrobenzopyran-2,4'-piperidine]

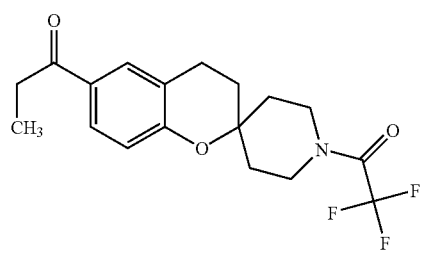 [SMILES: CCC(=O)c1ccc2c(c1)CCC1(CCN(C(=O)C(F)(F)F)CC1)O2]

A mixture of 1'-trifluoroacetyl-spiro[3,4-dihydrobenzopyran-2,4'-piperidine] (1.49 g, 4.98 mmol) and propanoyl chloride (0.4 mL, 5 mmol) in methylene chloride (13 mL) was cooled at 10° C. Tin tetrachloride (1M solution in methylene chloride) (0.76 mL, 6.5 mmol) was added at 10° C. and stirred at 10° C. for 20 min then quenched with aqueous 2N HCl at 0° C. The aqueous layer was extracted twice with methylene chloride and the combined organics was washed with brine, dried (Na₂SO₄), filtered, and concentrated to provide a crude product. The crude product was purified by ISCO (80 g column) chromatography using 17 to 35% EtOAc in hexane to produce 1'-trifluoroacetyl-6-(propanoyl)-spiro[3,4-dihydrobenzopyran-2,4'-piperidine] (1.42 g, 81%),
MS m/z=356 (M+H).

Step 2: Synthesis of 1'-Trifluoroacetyl-6-(3-methyl-4-oxo-butyric acid ethyl ester)-spiro[3,4-dihydrobenzopyran-2,4'-piperidine]

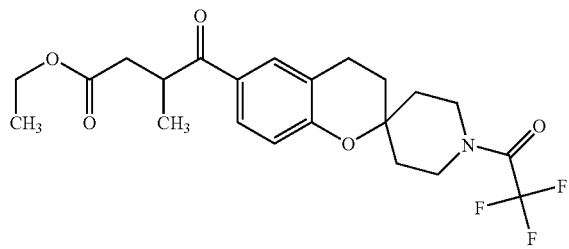 [SMILES: CCOC(=O)CC(C)C(=O)c1ccc2c(c1)CCC1(CCN(C(=O)C(F)(F)F)CC1)O2]

A solution of the product from step 1 (1'-trifluoroacetyl-6-(propanoyl)-spiro[3,4-dihydrobenzopyran-2,4'-piperidine]) (1.4 g, 3.9 mmol) in tetrahydrofuran (13 mL) was cooled at 0° C. Lithium diisopropylamide, (2M solution in THF) (2.16 mL, 4.33 mmol) was added dropwise and warmed to rt for 30 min. The reaction was cooled again to 0° C. and ethyl bromoacetate (0.48 mL, 4.30 mmol) was added dropwise and warmed to RT for 30 min then quenched with aqueous 1M HCl acid at 0° C. The aqueous layer was extracted twice with methylene chloride and the combined organics was washed with brine, dried (Na₂SO₄), filtered, and concentrated to give a crude 1'-trifluoroacetyl-6-(3-methyl-4-oxo-butyric acid ethyl ester)-spiro[3,4-dihydrobenzopyran-2,4'-piperidine] (2.21 g), MS m/z=442 (M+H).

Step 3: Synthesis of 6-(5-methyl-4,5-dihydro-2H-pyridazin-3-one-6-yl)-spiro[3,4-dihydrobenzopyran-2,4'-piperidine]

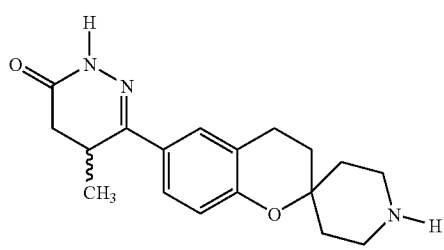 [SMILES: CC1CC(=O)NN=C1c1ccc2c(c1)CCC1(CCNCC1)O2]

A mixture of the product from step 2 (2.21 g, 5.01 mmol) and hydrazine monohydrate (1.5 mL, 30 mmol) in isopropanol (15 mL) was heated at 110° C. for 36 h. Isopropanol was evaporated at reduced pressure and azeotrophed twice with benzene to produce a crude product (2.45 g), MS m/z=314 (M+H). The material was used for the next reaction without further purification.

Step 4: Synthesis of 1-Cyclobutyl-6-(5-methyl-4,5-dihydro-2H-pyridazin-3-one-6-yl)-spiro[3,4-dihydrobenzopyran-2,4'-piperidine]

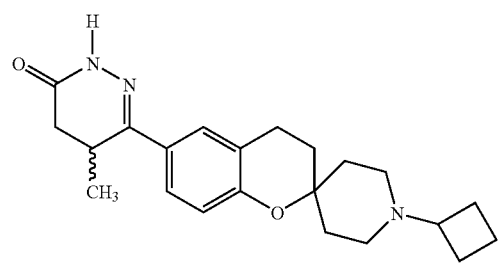 [SMILES: CC1CC(=O)NN=C1c1ccc2c(c1)CCC1(CCN(C3CCC3)CC1)O2]

A solution of the product from step 3 (2.45 g, 7.82 mmol) in a mixture of DMF (5 mL) and MeOH (15 mL) was stirred under argon. Cyclobutanone (1.8 mL, 24 mmol), sodium cyanoborohydride (1.2 g, 19 mmol) and acetic acid (0.90 mL, 20 mmol) were added sequentially and stirred at 60° C. for 24 h. The reaction mixture was concentrated at reduced pressure and partitioned between aqueous 1M sodium carbonate solution and methylene chloride. The aqueous layer was extracted twice with methylene chloride and the combined organics was washed with brine, dried (Na₂SO₄), filtered, and concentrated to provide a crude product. The crude product was purified by ISCO (40 g) chromatography using 2 to 10% methanol in methylene chloride to 10% methanol containing 4 mL of ammonium hydroxide in methylene chloride to obtain a pure product. The recovered pure product was dissolved in methylene chloride and washed with saturated sodium sodium bicarbonate solution, brine, dried (Na₂SO₄), filtered, and concentrated. The pure product was crystallized from a mixture of methylene chloride, ethanol, ether, and hexane to produce 1-cyclobutyl-6-(5-methyl-4,5-dihydro-2H-pyridazin-3-one-6-yl)-spiro[3,4-dihydrobenzopyran-2,4'-piperidine]: (550 mg, 19%, 95% purity), mp 207-209° C. (methylene chloride, ethanol, ether, and hexane), MS m/z=368 (M+H); $^1$H NMR (400 MHz, CDCl₃): δ 1.26 (d, J=7.33 Hz, 3H), 1.61-2.01 (m, 12H), 2.02-2.14 (m, 2H), 2.19-2.32 (m, 2H), 2.42-2.50 (m, 1H), 2.60-2.74 (m, 2H), 2.77-2.90 (m, 2H), 3.28-3.39 (m, 1H), 6.84-6.92 (m, 1H), 7.47-7.54 (m, 2H), 8.50 (s, 1H).

Example 13

1'-Cyclobutyl-6-(5-methyl-2H-pyridazin-3-one-6-yl)-spiro[3,4-dihydrobenzopyran-2,4'-piperidine]

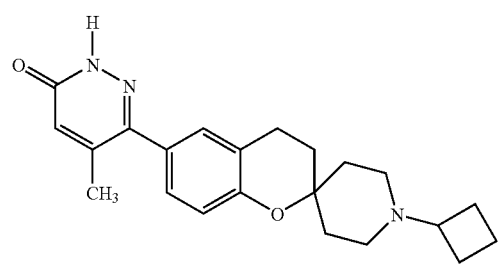 [SMILES: Cc1cc(=O)[nH]nc1-c1ccc2c(c1)CCC1(CCN(C3CCC3)CC1)O2]

A mixture of example 12 (103 mg, 0.28 mmol) and cesium carbonate (536 mg, 1.60 mmol) in dimethyl sulfoxide (6 mL) was heated at 100-110° C. for 27 h. The mixture was cooled to rt and partitioned between water and methylene chloride. Sodium chloride was added to the mixture and the aqueous layer was extracted three times with methylene chloride. The combined organics was washed with brine, dried ($Na_2SO_4$), filtered, and concentrated to provide a crude product. The crude product was purified by ISCO (40 g column) chromatography using 5% to 10% methanol in methylene chloride to 10% methanol containing 4% ammonium hydroxide in methylene chloride. The recovered product was dissolved in methylene chloride and washed with saturated aqueous sodium bicarbonate solution, brine, dried ($Na_2SO_4$), filtered, and concentrated to produce a pure product. The pure product was crystallized from a mixture of methylene chloride, ethanol, ether and hexane to give 1'-cyclobutyl-6-(5-methyl-2H-pyridazin-3-one-6-yl)-spiro[3,4-dihydrobenzopyran-2,4'-piperidine] (32 mg, 21%, 93% purity), mp 270-272° C. (methylene chloride, ethanol, ether and hexane), MS m/z=366 (M+H); 1H NMR (400 MHz, DMSO-$d_6$): δ 1.56-1.85 (m, 11H), 1.92-2.03 (m, 2H), 2.12 (s, 3H), 2.14-2.26 (m, 1H), 2.45-2.55 (m, 2H), 2.72-2.80 (m, 3H), 6.76-6.82 (m, 2H), 7.15-7.19 (m, 2H), 12.92 (s, 1H).

Example 14

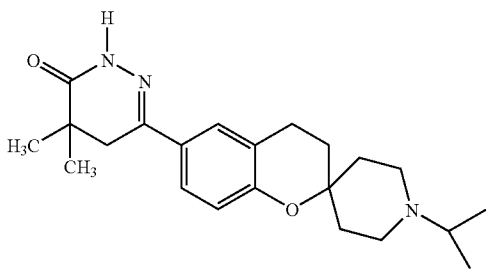 [SMILES: CC(C)N1CCC2(CCc3cc(C4=NNC(=O)C(C)(C)C4)ccc3O2)CC1]

1'-Isopropyl-[6-(4,4-dimethyl-4,5-dihydro-2H-pyridazin-3-one-6-yl)-spiro[3,4-dihydro[benzopyran-2,4'-piperidine]: mp 210-213° C. (methylene chloride, ethanol, ether, and hexane); MS m/z=370 (M+H); $^1$H NMR (400 MHz, CDCl$_3$): δ 1.15 (d, 6H, J=6.5 Hz), 1.25 (s, 6H), 1.8-1.91 (m, 6H), 2.66-2.84 (m, 9H), 6.88 (d, 2H, J=8.1 Hz), 7.47-7.49 (m, 2H), 8.45 (s, 1H).

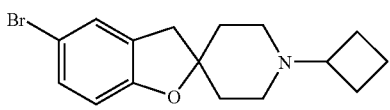 [SMILES: Brc1ccc2c(c1)CC1(CCN(C3CCC3)CC1)O2]

Step 1

To a solution of 5-bromo-spiro[benzofuran-2-(3H)-4'-piperidine] (260.0 mg, 0.97 mmol) in methanol (5.0 mL, 120 mmol) was added 100 μl (1.75 mmol) of AcOH followed by cyclobutanone (679.6 mg, 9.7 mmol) at rt. To this mixture was added sodium cyanoborohydride (200 mg, 3.18 mmol) in small portions over 5 min. After 5 min. HPLC indicated about 10% of starting material. Added another 100 μl of AcOH followed by another 200 mg of NaCNBH$_3$. After stirring for 15 min, LCMS indicated total disappearance of the starting material. The mixture was concentrated and extracted with CH$_2$Cl$_2$/sat. NaHCO$_3$. After evaporation and drying ($Na_2SO_4$), a pale yellow oil was obtained which was purified by ISCO chromatography using CH$_2$Cl$_2$ and 0-10% MeOH containing 1% aq. NH$_4$OH to afford the title compound as a waxy white solid (250 mg, 74%). Mp 79-80° C., MS: m/z 322/324 (M+1, Br isotopic peaks). $^1$HNMR (400 MHz, CDCl$_3$): δ 7.28 (d, J=0.75 Hz, 1H), 7.20 (d, J=8.4 Hz, 1H), 6.64 (d, J=8.4 Hz, 1H), 2.98 (s, 2H), 2.80 (m, 1H), 2.1-2.6 (br.s, 4H) & 1.6-2.1 (m, 10H).

Example 15

1'-Cyclobutyl-5-(6-chloropyridazin-3-yl)spiro[benzofuran-2(3H)-4'-piperidine]

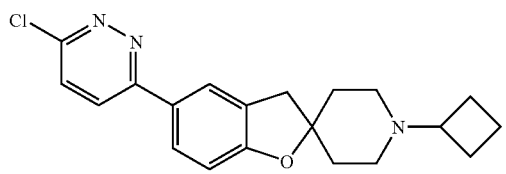 [SMILES: Clc1ccc(-c2ccc3c(c2)CC2(CCN(C4CCC4)CC2)O3)nn1]

Into a dry, round bottom flask was added tris(dibenzylideneacetone)dipalladium(0) (22 mg, 0.024 mmol) and tricyclohexylphosphine (28.0 mg, 0.1 mmol) under N$_2$ atmosphere. Dioxane (6 mL) was added and the dark solution was stirred for 30 min at rt. To this dark brownish solution was added 4,4,5,5,4',4',5',5'-octamethyl-[2,2']bi[[1,3,2]dioxaborolanyl] (0.20 g, 0.79 mmol), potassium acetate (0.10 g, 1.02 mmol) and a solution of 1'-cyclobutyl-5-bromo-spiro[benzofuran-2 (3H)-4'-piperidine] (245.00 mg, 0.76 mmol) in dioxane (5 mL) in that order. The mixture was purged with N$_2$ for 10 min. and heated at 80° C. After refluxing for 14 h, the LCMS indicated the absence of the bromide with the expected m/z 370 mass for the borolane. The crude borolane intermediate was subjected to the Suzuki coupling reaction by adding 3,6-dichloropyridazine (0.55 g, 3.69 mmole), (Ph$_3$P)$_4$Pd (85 mg, 0.073 mmole), THF (15 mL), EtOH (5 mL) and saturated aqueous NaHCO$_3$ (8 mL). After 10 h, HPLC indicated the expected product as the major peak. The reaction was concentrated and purified by ISCO chromatography (DCM/MeOH/NH$_4$OH) to obtain the product a beige solid (80 mg, 28%). mp 193-194° C., MS: m/z 356 (M+1). $^1$HNMR (CDCl$_3$): δ 7.97 (s, 1H), 7.73-7.77 (m, 2H), 7.52 (dd, J=8.8, 1.5 Hz, 1H), 6.9 (d, J=8.4 Hz, 1H), 3.1 (s, 2H), (2.8, m, 1H), 2.4-2.6 (br.s, 4H) & 1.65-2.15 (m, 10H).

Example 16

1'-Cyclobutyl-5-(6-oxo-1,6-dihydropyridazin-3-yl)spiro[benzofuran-2(3H)-4'-piperidine]

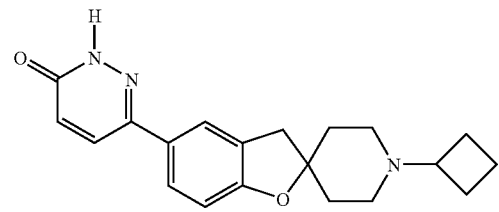 [SMILES: O=c1ccc(-c2ccc3c(c2)CC2(CCN(C4CCC4)CC2)O3)n[nH]1]

To example 15 (1'-cyclobutyl-5-(6-chloropyridazin-3-yl) spiro[benzofuran-2(3H)-4'-piperidine]) (75.00 mg, 0.2108 mmol) in acetic acid (5.0 mL, 88 mmol) was added sodium acetate (100.00 mg, 1.219 mmol) and refluxed for 3 h. The mixture was evaporated, the residue co-evaporated with toluene (2×10 mL) and then chromatographed by ISCO chromatography (DCM/MeOH/NH$_4$OH) to afford the title compound 50 mg (68%). mp 227-228° C., MS: m/z 338 (M+1). $^1$HNMR (CDCl$_3$): δ 12 (s, 1H), 7.7 (d, J=9.85 Hz, 1H), 7.6 (s, 1H), 7.55 (d, J=8.4 Hz, 1H), 7.05 (d, J=9.85 Hz, 1H), 6.80 (d, J=8.4 Hz, 1H), 3.05 (s, 2H), (2.85, m, 1H), 2.4-2.6 (br.s, 4H) & 1.65-2.15 (m, 10H).

Example 17

6-spiro[3,4-dihydrobenzopyran-2,4'-piperidine]-6-yloxy)-4-chloropyridazine

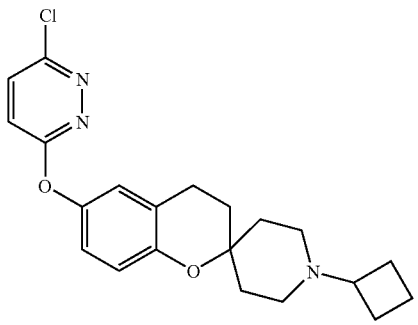 [SMILES: Clc1ccc(Oc2ccc3c(c2)CCC2(CCN(C4CCC4)CC2)O3)nn1]

Step 1

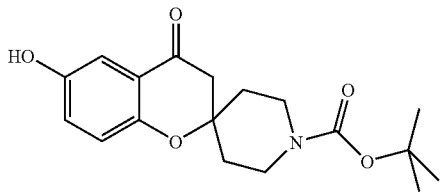 [SMILES: CC(C)(C)OC(=O)N1CCC2(CC1)CC(=O)c1cc(O)ccc1O2]

1'-t-Butyloxycarbonyl-4-oxo-6-hydroxy-spiro [3Hbenzopyran-2,4'-piperidine]

A solution of 2,5-dihydroxyacetophenone (15 g, 98 mmol), 4-oxo-piperidine-1-carboxylic acid tert-butyl ester (20 g, 100 mmol) and pyrrolidine (21 mL, 260 mmol) in methanol (146 mL) was stirred at reflux for 23 h and concentrated under vacuum to produce a red oily crude material. The oily crude material was purified by ISCO (330 g column) chromatography using 27 to 80% ethyl acetate in hexane to afford the product of step 1 (27 g, 82%), mp 72-74° C. (ethyl acetate, ether and hexane), MS m/z=332 (M−H).

Step 2

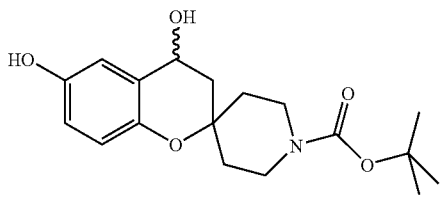 [SMILES: CC(C)(C)OC(=O)N1CCC2(CC1)CC(O)c1cc(O)ccc1O2]

1'-t-Butyloxycarbonyl-4,6-dihydroxy-spiro[3Hbenzopyran-2,4'-piperidine]

A solution of the product from step 1 (4.51 g, 13.5 mmol) in methanol (50 mL) was cooled to 15° C. and sodium borohydride was added slowly and the mixture was further stirred for 30 min and then concentrated. The crude residue was partitioned between methylene chloride and water and the aqueous layer was extracted twice with methylene chloride. The combined organics was washed with brine, dried (Na$_2$SO$_4$), filtered and concentrated to produce the product of step 2 (4.1 g, 90%), mp 171-173° C. (ethyl acetate, ether and hexane), MS m/z=334 (M−H).

Step 3

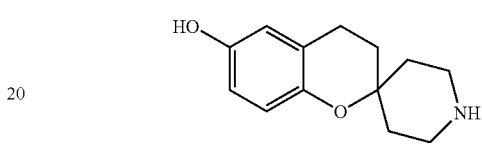

6-hydroxy-spiro[3Hbenzopyran-2,4'-piperidine]

A solution of the product from step 2 (23.5 g, 70.1 mmol) and triethylsilane (49 mL, 310 mmol) in methylene chloride (150 mL) was cooled to 10° C. Trifluoroacetic acid (78 mL, 1000 mmol) was added dropwise and further stirred at room temperature for 15 h. The mixture was concentrated under vacuum and then azeotroped thrice with toluene to produce amber color oily material, which upon standing under vacuum gave a solid product. The crude product was triturated with a mixture of hexane:ether (1:1 ratio, 175 mL) to produce a pure product, which was dried at 80° C. to give a tan solid as the TFA salt (21 g, 90%), mp 208-210° C. (ether and hexane), MS m/z=220 (M+H).

Step 4

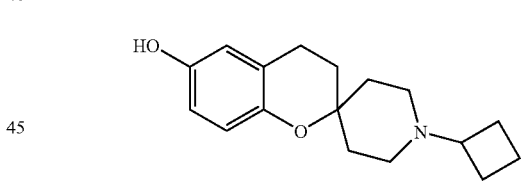

1'-cyclobutyl-4-hydroxy-spiro[3,4-dihydro-benzopyran-2,4'-piperidine]

A solution of the product from step 3 (0.76 g, 3.5 mmol) in a mixture of DMF (2 mL) and MeOH (10 mL) was stirred under argon. Cyclobutanone (1.00 mL, 10 mmol), acetic acid (0.4 mL, 7 mmol) sodium cyanoborohydride (0.9 g, 10 mmol) were added sequentially and stirred at 60° C. for 15 h. The reaction mixture was concentrated at reduced pressure and partitioned between aqueous 1M sodium carbonate solution and methylene chloride. The aqueous layer was extracted twice with methylene chloride and the combined organics was washed with brine, dried (Na$_2$SO$_4$), filtered, and concentrated to provide a crude product. The recovered pure product was dissolved in methylene chloride and washed with saturated aqueous sodium bicarbonate solution, brine, dried (Na$_2$SO$_4$), filtered, and concentrated. The product was crystallized from a mixture of methylene chloride, ethanol, ether, and hexane to produce the product of step 4 (0.5 g, 53%), mp 211-213° C. (methylene chloride, ethanol, ether and hexane), MS m/z=274 (M+H).

Step 5

Example 17

A solution of the product from step 4 (200 mg, 0.73 mmol) in dimethyl sulfoxide (10 mL) was added sodium hydride (35 mg, 1.4 mmol) at room temperature. After stirring for 30 min at room temperature 3,6-dichloro pyridazine (218 mg, 1.46 mmol) was added and the reaction mixture was heated to 60° C. for 1 h and poured into brine solution at room temperature. The aqueous layer was extracted four times with methylene chloride and the combined organics was washed with brine, dried (Na$_2$SO$_4$), filtered and concentrated to produce a crude material. The crude material was purified by ISCO (40 g) chromatography using a mixture of methanol in methylene chloride to afford Example 17 (250 mg, 87%), mp 128-130° C. (methylene chloride, methanol, ether and hexane), MS m/z=386 (M+H).

Example 18

6-spiro[3,4-dihydrobenzopyran-2,4'-piperidine]-6-yloxy)-2H-pyridazin-3-one

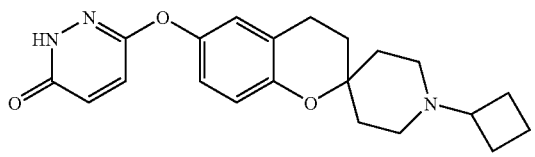 [SMILES: O=c1ccc(Oc2ccc3c(c2)CCC2(CCN(C4CCC4)CC2)O3)n[nH]1]

A mixture of example 17 (209 mg, 0.54 mmol) and sodium acetate (32 mg, 0.39 mmol) in acetic acid (5 mL) was heated to 110-115° C. for 7 h. The reaction mixture was concentrated and azeotroped twice with toluene then partitioned between methylene chloride and the aqueous saturated sodium bicarbonate solution. The aqueous layer was extracted twice with methylene chloride and the combined organics was washed with brine, dried (Na$_2$SO$_4$), filtered, and concentrated to afford relatively pure product. The pure product was crystallized from a mixture of methylene chloride, methanol, ether, and hexane to produce 6-(3,4-dihydro spiro[2H-1-benzopyran-2,4'-piperidine]-6-yloxy)-2H-pyridazin-3-one as an off-white solid (170 mg, 76%), mp 233-235° C. (methylene chloride, methanol, ether and hexane), MS m/z=368 (M+H); $^1$H NMR (400 MHz, CDCl$_3$): δ 1.54-2.01 (m, 10H), 2.03-2.13 (m, 2H), 2.18-2.32 (m, 2H), 2.60-2.71 (m, 2H), 2.74-2.89 (m, 3H), 6.82-6.91 (m, 3H), 7.00 (d, J=9.92 Hz, 1H) 7.185 (d, J=9.91 Hz, 1H), 9.84 (br s, 1H).

Example 19

1'-Cyclobutyl-[6-(2H-pyridazin-3-one-5-yl)-spiro[3,4-dihydro-benzopyran-2,4'-piperidine]

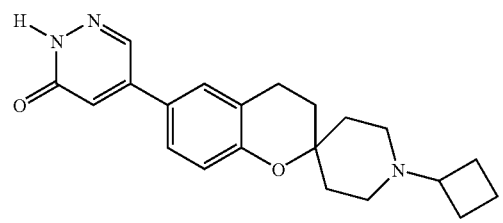 [SMILES: O=c1cc(-c2ccc3c(c2)CCC2(CCN(C4CCC4)CC2)O3)cn[nH]1]

To a 100 mL flask was added 2-hydroxymethyl-5-iodo-2H-pyridazin-3-one (0.19 g, 0.76 mmol), 1'-cyclobutyl-6-(4,4,5,5-tetramethyl-1,3,2-dioxaborolane)-spiro[3,4-dihydro-benzopyran-2,4'-piperidine] (0.34 g, 0.89 mmol), tetrakis(triphenylphosphine)palladium(0) (0.088 g 0.076 mmol), K$_2$CO$_3$ (0.53 g, 3.8 mmol), in 1,2-dimethoxyethane (8 mL) and water (8 mL). The reaction mixture was flashed with N$_2$ for 25 min and was then heated to reflux for 16 h. The reaction was cooled to rt and small amount of NaCNBH$_3$ was added and stirred for 5 min. The reaction was diluted with CH$_2$Cl$_2$/MeOH (100 mL, 3:1) then washed with saturated NaHCO$_3$, brine and dried (Na$_2$SO$_4$). The product was purified by prep TLC (6% MeOH/CH$_2$Cl$_2$) and the product collected and triturated with CH$_3$CN to give 115 mg; mp 216-219° C.; 1HNMR (DMSO): 12.95 (s, 1H), 8.25 (s, 1H), 7.6 (s, 1H), 7.45 (d, 1H), 6.95 (s, 1H), 6.8 (d, 1H), 2.8 (m, 3H), 2.2-2.3 (br, 2H), 1.95-2.0 (br, 2H), 1.6-1.9 (m, 11H). MS m/z 352 (M+1)

The following examples were synthesized using the methods for example 19 with 6-chloro-2-methyl-2H-pyridazin-3-one (Ex. 20) and 3-chloro-6-methoxypyridazine (Ex. 21).

| Example | Structure | Mp (° C.) | MS m/z |
|---|---|---|---|
| 20 | 1'-Cyclobutyl-[6-(2-methyl-pyridazin-3-one-6-yl)-spiro[3,4-dihydro-benzopyran-2,4'-piperidine] | 147-149 | 366 (M + H) |

| Example | Structure | Mp (° C.) | MS m/z |
|---|---|---|---|
| 21 | 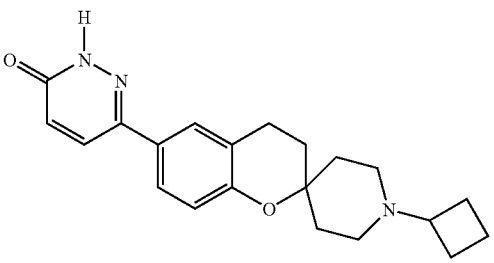<br>1'-Cyclobutyl-[6-(2H-pyridazin-3-one-6-yl)-spiro[3,4-dihydro-benzopyran-2,4'-piperidine] | 273-275 | 352 (M + H) |

Racemic Example 10 was separated into two isomers using chiral chromatography; ChiralCel OJ-H and 0.1% diethylamine in 35% methanol/$CO_2$. The individual isomers are designated as Example 22 (Peak A, elutes first from chiral column) and Example 23 (Peak B, elutes second from chiral column).

| Example | Structure | mp (° C.) | MS m/z |
|---|---|---|---|
| 22 | 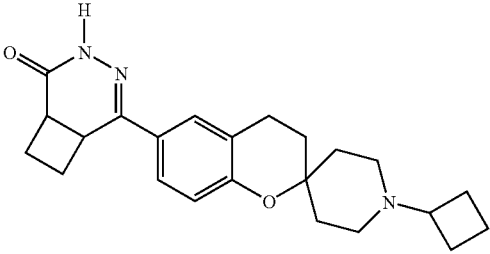 [SMILES: O=C1NN=C(c2ccc3c(c2)CCC2(CCN(C4CCC4)CC2)O3)C2CCC12] | >300 HCl | 380 (M + H) |
| 23 | 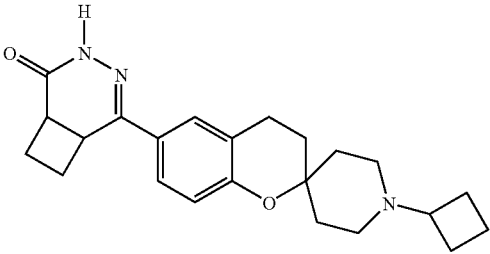 [SMILES: O=C1NN=C(c2ccc3c(c2)CCC2(CCN(C4CCC4)CC2)O3)C2CCC12] | >300 HCl | 380 (M + H) |

Example 24

1'-Cyclobutyl-6-(3-(2-pyridazin-3-one)propyloxy]-spiro[3,4-dihydrobenzopyran-2,4'-piperidine]

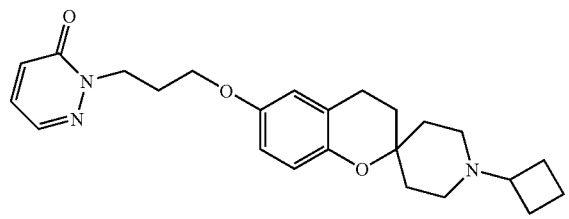 [SMILES: O=c1cccnn1CCCOc1ccc2c(c1)CCC1(CCN(C3CCC3)CC1)O2]

1'-Cyclobutyl-4-hydroxy-spiro[3,4-dihydro-benzopyran-2,4'-piperidine] (0.3 g, 1.1 mmol) in DMF (7 mL) was added NaH (88 mg, 3.7 mmol). After 0.5 h, 2-(3-chloropropyl)-2-H-pyridazin-3-one (0.2 g, 1.15 mmol) was added and the reaction heated to 60° C. for 1 h, concentrated and partitioned between DCM and aqueous $NaHCO_3$, NaCl solution and dried ($Na_2SO_4$). The product was purified by silica gel chromatography (5-12% MeOH/DCM) to give 360 mg (80%). mp 207-209° C. (HCl salt), MS m/z=410 (M+H).

Example 25

1'-Cyclobutyl-6-(3-(2-pyridazin-3-one)-2-hydroxypropyloxy]-spiro[3,4-dihydrobenzopyran-2,4'-piperidine]

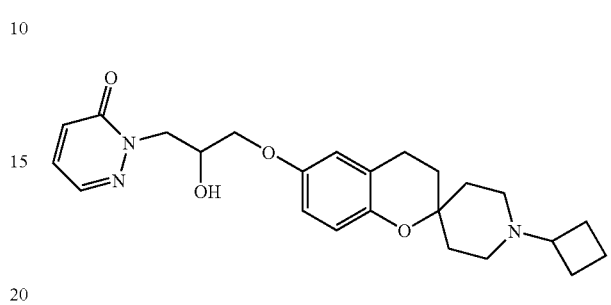

This compound was synthesized using the method for example 24 and 2-oxiranylmethyl-2H-pyridazin-3one. mp 201-203° C. (HCl salt), MS m/z=426 (M+H).

The following examples were synthesized from 6-bromo-1'-cyclobutyl-spiro[1,3-benzodioxine-2,4'-piperidine] using methods for example 19-21.

| Example | Structure | Mp (° C.) | MS m/z |
|---|---|---|---|
| 26 | 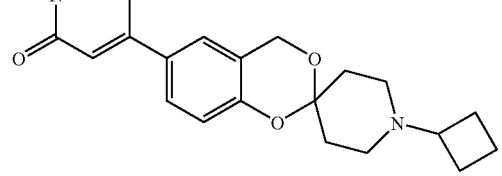<br>1'-Cyclobutyl-6-(2H-pyridazin-2-one-5-yl)-spiro[1,3benzodioxine-2,4'-piperidine] | 258-262 (HCl) | 354 (M + 1) |
| 27 | 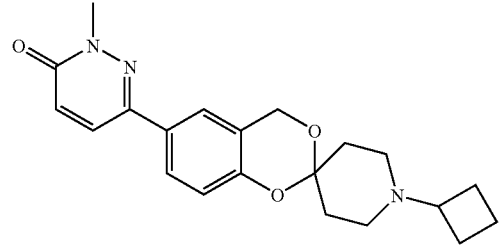<br>1'-Cyclobutyl-6-(2-methyl-pyridazin-2-one-6-yl)-spiro[1,3benzodioxine-2,4'-piperidine] | 185-187 | 368 (M + H) |

-continued

| Example | Structure | Mp (° C.) | MS m/z |
|---|---|---|---|
| 28 | 1'-Cyclobutyl-6-(2H-pyridazin-2-one-6-yl)-spiro[1,3benzodioxine-2,4'-piperidine] | 273-275 | 354 (M + H) |
| 29 | 1'-Cyclobutyl-7-methyl-6-(2H-pyridazin-2-one-6-yl)-spiro[1,3benzodioxine-2,4'-piperidine] | 230-232 | 368 (M + H) |
| 30 | 1'-Cyclobutyl-7-methyl-6-(2-methyl-pyridazin-2-one-6-yl)-spiro[1,3benzodioxine-2,4'-piperidine] | 269-270 (HCl) | 382 (M + H) |
| 31 | 1'-Cyclobutyl-5-methyl-6-(2H-pyridazin-2-one-6-yl)-spiro[1,3benzodioxine-2,4'-piperidine] | 255-257 (HCl) | 368 (M + H) |

| Example | Structure | Mp (° C.) | MS m/z |
|---|---|---|---|
| 32 | 1'-Cyclobutyl-6-(2H-phthalazin-1-one-4-yl)-spiro[1,3benzodioxine-2,4'-piperidine] | 258-259 | 404 (M + H) |
| 33 | 1'-Cyclobutyl-6-(2H-5-phenyl-pyridazin-2-one-6-yl)-spiro[1,3benzodioxine-2,4'-piperidine] | 260-262 | 430 (M + H) |

Synthesis of 6-bromo-1'-cyclobutyl-spiro[1,3-benzodioxine-2,4'-piperidine]

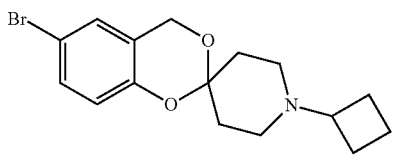 [SMILES: Brc1ccc2c(c1)COC1(CCN(C3CCC3)CC1)O2]

To a solution of 6-bromo-1'H-spiro[1,3benzodioxine-2,4'-piperidine] (238 g, 0.84 mol) and cyclobutanone (117 g, 1.676 mol) in THF (2 L) on an ice bath was added NaBH(OAc)₃ (266 g, 1.255 mol) portion wise over 25 min under nitrogen. The resulting mixture was allowed to warm to rt and stirred overnight. The reaction mixture was poured into a mixture of ice (1.7 L), saturated NaHCO₃ (1.7 L) and ethyl acetate (1.7 L) with vigorous stirring. After separation, the aqueous phase was adjusted to pH 11 by addition of 2M NaOH and extracted with ethyl acetate (2 L×2). The extracts were combined, washed with saturated NaHCO₃ (1.5 L), brine (1.5 L), dried over Na₂SO₄ and concentrated. The obtained solid was purified by column chromatography (hexanes/ethyl acetate 3/1 to 1/1) to give 208 g (73%). MS m/z=339 (M+1).

Example 34

1'-Cyclobutyl-6-[5H-4,4-dimethylpyridazin-3-one)-spiro[1,3-benzodioxine-2,4'-piperidine]

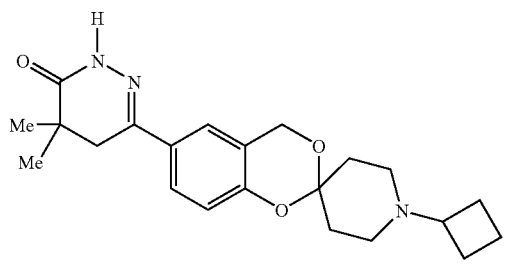

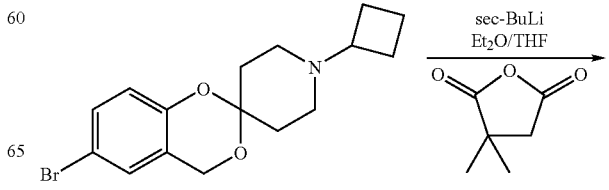

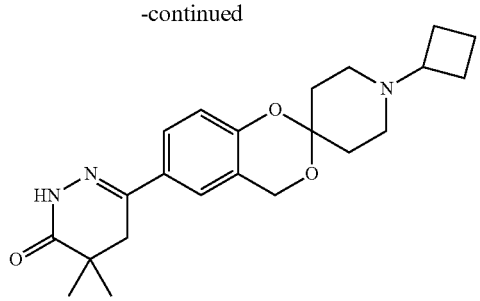

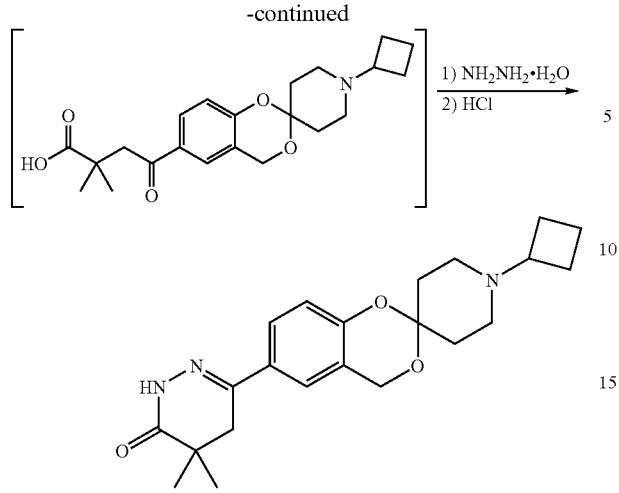

Example 34

Method A: Into a 3-neck round bottom flask 6-bromo-1'-cyclobutyl-spiro[1,3benzodioxine-2,4'-piperidine] (5.0 g, 15 mmol) in 80 mL THF/ether (4:1) was cooled at −76° C. under an atmosphere of nitrogen sec-Butyl lithium (1.4 M in cyclohexane, 13 mL, 18 mmol) was added dropwise and the mixture stirred at that temperature for 4 h. Then, 3,3-dimethyl-dihydrofuran-2,5-dione (2.8 g, 22 mmol) in THF (10 mL) was added dropwise, the cooling bath was removed and the reaction was allowed to warm to 0° C. for 1 h. LCMS showed the acid product (MS m/z=386 (M−1). Water (5 mL) was added, and the mixture concentrated and the resulting oil dissolved in iPrOH (40 mL). Hydrazine hydrate (2 mL, 50 mmol) was added and the reaction heated at 110° C. for 24 h, cooled to rt and concentrated to remove iPrOH. The water layer was decanted from the white semi-solid material, which was dissolved in DMC and dried (MgSO$_4$). The product was purified on ISCO (silica gel, 95/5 increasing to 9/1 DCM/MeOH) to give 1.9 g (33%). mp 266-269° C. (HCl salt; MeOH-ether), $^1$H NMR (DMSO) δ 11.4 (s, 1H), 10.8 (s, 1H), 7.6-7.65 (m, 1H), 7.54 (s, 1H), 6.9-6.95 (m, 1H), 4.92-4.94 (d, 2H, J=10 Hz), 3.68-3.76 (p, 1H, J=7.6 Hz), 3.2-3.3 (b, 3H), 2.88 (m, 2H), 2.78 (m, 2H), 2.37-2.4 (m, 1H), 2.16-2.25 (m, 6H), 1.67-1.77 (m, 2H), 1.06 (s, 6H). LCMS m/z=384 (M+1).

Method B:

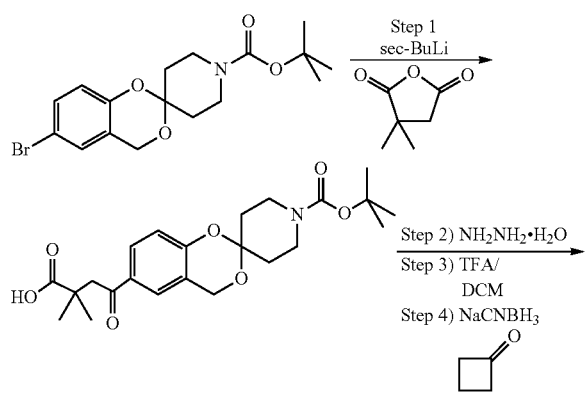

Example 34

Step 1. To 1'-carboxylic acid tert-butyl ester-6-bromo-spiro[1,3-benzodioxine-2,4'-piperidine] (14.58 g, 37.94 mmol) in ether (300 mL) under argon at −78° C. was added sec-butyllithium (1.4 M; 32.5 mL, 45.5 mmol) dropwise and the reaction was stirred at −78° C. for 30 min. 3,3-Dimethyldihydrofuran-2,5-dione in ether (10 mL) was added and the reaction was stirred for 30 min at −78° C. and quenched with water (~40 mL). The reaction was warmed to rt and concentrated to remove the organic solvents. The aqueous layer was acidified with 5N HCl to pH=3-4, extracted with dichloromethane (150 mL), and the organic layer was washed with water and brine, dried over sodium sulfate, and concentrated. The product was purified using silica gel column chromatography (2-3% methanol/dichloromethane). The fractions were concentrated, triturated with dichloromethane (~5 mL)/ether (~10 mL)/hexanes (~15-20 mL), and filtered off white solid to obtain 5.52 g (34%); MS m/z: 434 (M+H).

Step 2. To the product from step 1 (5.52 g, 12.7 mmol) (1'-carboylic acid tert-butyl ester-6-(2,2-dimethyl-4-oxo-butyric acid)-spiro[1,3-benzodioxine-2,4'-piperidine]) in isopropyl alcohol (70 mL) was added hydrazine monohydrate (0.956 mL, 19.1 mmol) and the reaction was heated at 80° C. overnight and concentrated. The residue was partitioned between water/dichloromethane, washed with brine, dried over sodium sulfate, and concentrated to obtain 5.4 g (>95%) of a crude product; MS m/z: 430 (M+H).

Step 3. Example 35. To the product from step 2 (1'-carboxylic acid tert-butyl ester-6-(4,4-dimethyl-4,5-dihydro-2H-pyridazin-2-one)-spiro[1,3-benzodioxine-2,4'-piperidine] (5.46 g, 12.7 mmol) in dichloromethane (100 mL) was added trifluoroacetic acid (10 mL, 129.8 mmol) and the reaction was stirred for 4 h at rt and concentrated. The product was azeotroped with benzene and dried under vacuum to give 5.6 g of crude product as an oil; MS m/z: 330 (M+H).

Step 4. Example 34. To the product from step 3 (1'-H-6-(4,4-dimethyl-pyridazinone)-spiro[1,3-benzodioxine-2,4'-piperidine]trifluoroacetic acid salt) (5.6 g, 12.6 mmol) and cyclobutanone (2.83 mL, 37.9 mmol) in DMF (10 mL)/methanol (50 mL)/acetic acid (3 mL) under argon cooled at 0° C. was added sodium cyanoborohydride (3.97 g, 63.2 mmol) slowly in portions. The reaction was heated at 60° C. overnight and concentrated. The reaction was partitioned between dichloromethane/1N sodium carbonate, washed with water and brine, dried over sodium sulfate, and concentrated. The product was purified using a single step silica gel column (5% methanol/dichloromethane) and concentrated. The free base was dissolved in chloroform (~50 mL) and 1N HCl/ether (~17 mL) was added. The product was collected after addition of ether to give 3.64 g (67%) of white solid; mp 269-270° C. MS m/z: 384 (M+H).

The following examples were synthesized using modifications to the procedure for example 34 or methods described herein.

| Example | Structure | Mp (° C.) | MS m/z |
|---|---|---|---|
| 36 | 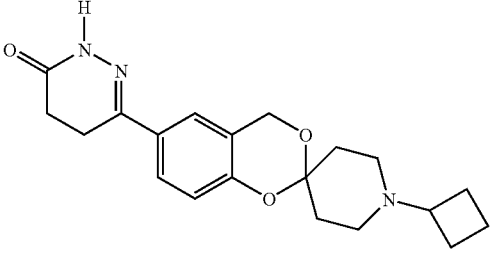<br>1'-Cyclobutyl-6-(4,5-dihydropyridazin-3-one)-spiro[1,3-benzodioxine-2,4'-piperidine] | 192-194 | 356 (M + H) |
| 37 | 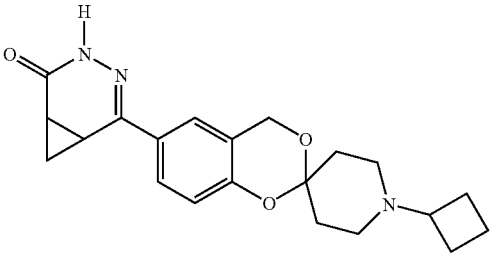<br>1'-Cyclobutyl-6-(4,5-dihydro-4,5-cyclopropylpyridazin-3-one)-spiro[1,3-benzodioxine-2,4'-piperidine] | >300 (HCl) | 368 (M + H) |
| 38 | 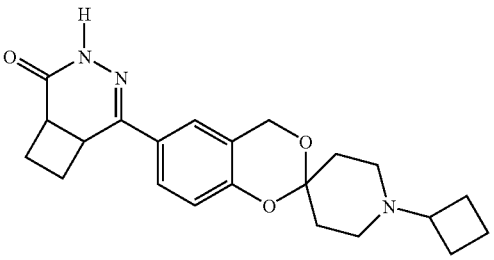<br>1'-Cyclobutyl-6-(4,5-dihydro-4,5-cyclobutylpyridazin-3-one)-spiro[1,3-benzodioxine-2,4'-piperidine] | 271-274 (HCl) | 382 (M + H) |
| 39 | 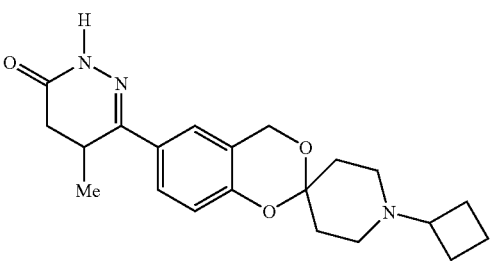<br>1'-Cyclobutyl-6-(4,5-dihydro-5-methylpyridazin-3-one)-spiro[1,3-benzodioxine-2,4'-piperidine] | 209-214 (HCl) | 370 (M + H) |

-continued

| Example | Structure | Mp (° C.) | MS m/z |
|---|---|---|---|
| 40 | 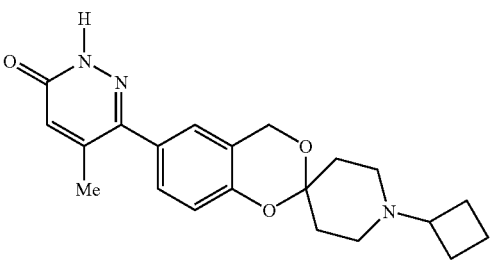<br>1'-Cyclobutyl-6-(5-methylpyridazin-3-one)-spiro[1,3-benzodioxine-2,4'-piperidine] | 265-267 (HCl) | 368 (M + H) |
| 41 | 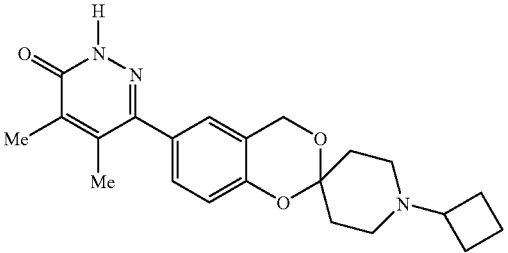<br>1'-Cyclobutyl-6-(4,5-dimethylpyridazin-3-one)-spiro[1,3-benzodioxine-2,4'-piperidine] | >300 (HCl) | 382 (M + H) |

Utility

The compounds of the present invention are useful, inter alia, as therapeutic agents. Particularly, the compounds are useful for interacting with the $H_3$ receptor. In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting $H_3$ activity comprising providing a compound of the present invention in an amount sufficient to result in effective inhibition. Particularly, the compounds of the present invention can be administered to treat such diseases and disorders such as narcolepsy or other sleep/wake disorders, such as obstructive sleep apnea/hypopnea syndrome, and shift work sleep disorder; feeding behavior disorder, eating disorders, obesity, cognition disorders, arousal disorders, memory disorders, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction. In certain embodiments, the compounds can be administered to treat narcolepsy or other sleep/wake disorders, such as obstructive sleep apnea/hypopnea syndrome, and shift work sleep disorder; obesity, cognition disorders, attention deficit hyperactivity disorder (ADHD), and dementia. In other embodiments, the compounds can be administered to treat narcolepsy or other sleep/wake disorders, such as obstructive sleep apnea/hypopnea syndrome, and shift work sleep disorder; or they can used to treat obesity, or they can used to treat cognition disorders, or they can used to treat attention deficit hyperactivity disorder (ADHD), or they can used to treat dementia.

Compounds of the invention either have demonstrated or are expected to demonstrate inhibition of $H_3$ and thereby for utility for treatment of the indications described herein. Such utilities can be determined using, for example, the following assays as set forth below. They are not intended, nor are they to be construed, as limiting the scope of the disclosure.

Rat $H_3$ Assays:

Cell line development and membrane preparation. The rat $H_3$ receptor cDNA was PCR amplified from reverse-transcribed RNA pooled from rat thalamus, hypothalamus, striatum and prefrontal cortex with a sequence corresponding to by #338-1672 of Genbank file #NM_053506, encoding the entire 445-amino-acid rat histamine $H_3$ receptor. This was engineered into the pIRES-neo3 mammalian expression vector, which was stably transfected into the CHO-A3 cell line (Euroscreen, Belgium), followed by clonal selection by limiting dilution. Cells were harvested and cell pellets were frozen (−80° C.). Cell pellets were resuspended in 5 mM Tris-HCl, pH 7.5 with 5 nM EDTA and a cocktail of protease inhibitors (Complete Protease Inhibitior Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM $MgCl_2$ and protease inhibitors, recentrifuged as above and the final pellet resuspended in membrane buffer plus 250 mM sucrose and frozen at −80° C.

Radioligand Binding. Membranes were resuspended in 50 mM Tris HCl (pH 7.4), 5 mM $MgCl_2$, 0.1% BSA. The membrane suspensions (10 μg protein per well) were incubated in a 96 well microtiter plate with [$^3$H]-N-alpha-methylhistamine (approximately 1 nM final concentration), test compounds at various concentrations (0.01 nM-30 μM) and scintillation proximity beads (Perkin Elmer, FlashBlueGPCR Scintillating Beads) in a final volume of 80 µl for 4 hours at room temperature, protected from light. Non-specific binding was determined in the presence of 10 µM clobenpropit. Radioligand bound to receptor, and therefore in proximity to the scintillation beads, was measured using a MicroBeta scintillation counter.

GTPγS Binding. Membranes were resuspended in 20 mM HEPES pH 7.4 containing 1 mM EDTA, 0.17 mg/ml dithiothreitol, 100 mM NaCl, 30 µg/ml saponin and 5 mM $MgCl_2$. For measurement of inverse agonist activity, increasing concentrations of test compounds were incubated in a 96 well microtiter plate with 10 µg/well membrane protein, 5 µM GDP, scintillation proximity beads (Perkin Elmer, FlashBlue-GPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 µM GTP. A decrease in bound [$^{35}$S]-GTPγS is indicative of $H_3$ receptor inverse agonist activity in this assay. Antagonist activity of test compounds was determined in a similar experiment under the following conditions. Membranes were resuspended in 20 mM HEPES pH 7.4 containing 1 mM EDTA, 0.17 mg/ml dithiothreitol, 200 mM NaCl, 30 µg/ml saponin and 20 mM $MgCl_2$. The membranes were incubated at 10 µg/well membrane protein in a microtiter plate with increasing concentrations of test compounds, 20 µM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of $H_3$ receptor antagonist activity in this assay.

Human $H_3$ Assays:

Methods: CHO cells stably expressing the human $H_3$ receptor (GenBank: NM_007232) were harvested and cell pellets were frozen (−80° C.). Cell pellets were resuspended in 5 mM Tris-HCl, pH 7.5 with 5 nM EDTA and a cocktail of protease inhibitors (Complete Protease Inhibitior Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM $MgCl_2$ and protease inhibitors, recentrifuged as above and the final pellet resuspended in membrane buffer plus 250 mM sucrose and frozen at −80° C.

Radioligand Binding. Membranes were resuspended in 50 mM Tris HCl (pH 7.4), 5 mM $MgCl_2$, 0.1% BSA. The membrane suspensions (10 µg protein per well) were incubated in a 96 well microtiter plate with [$^3$H]-N-alpha-methylhistamine (approximately 1 nM final concentration), test compounds at various concentrations (0.01 nM-30 µM) and scintillation proximity beads (Perkin Elmer, FlashBlueGPCR Scintillating Beads) in a final volume of 80 µl for 4 hours at room temperature, protected from light. Non-specific binding was determined in the presence of 10 µM clobenpropit. Radioligand bound to receptor, and therefore in proximity to the scintillation beads, was measured using a MicroBeta scintillation counter.

GTPγS Binding. Membranes were resuspended in 20 mM HEPES pH 7.4 containing 1 mM EDTA, 0.17 mg/ml dithiothreitol, 100 mM NaCl, 30 µg/ml saponin and 5 mM $MgCl_2$. For measurement of inverse agonist activity, increasing concentrations of test compounds were incubated in a 96 well microtiter plate with 10 µg/well membrane protein, 5 µM GDP, scintillation proximity beads (Perkin Elmer, FlashBlue-GPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 µM GTP. A decrease in bound [$^{35}$S]-GTPγS is indicative of $H_3$ receptor inverse agonist activity in this assay. Antagonist activity of test compounds was determined in a similar experiment under the following conditions. Membranes were resuspended in 20 mM HEPES pH 7.4 containing 1 mM EDTA, 0.17 mg/ml dithiothreitol, 200 mM NaCl, 30 µg/ml saponin and 20 mM $MgCl_2$. The membranes were incubated at 10 µg/well membrane protein in a microtiter plate with increasing concentrations of test compounds, 20 µM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of $H_3$ receptor antagonist activity in this assay.

Other assays that may be used in connection with the present invention are set forth below. Examples of the present invention can be tested in the following in vivo models:

Evaluation of Wake Promoting Activity in Rats

The methodology utilized for evaluating wake promoting activity of test compounds is based on that described by Edgar and Seidel, *Journal of Pharmacology and Experimental Therapeutics,* 283:757-769, 1997, and incorporated herein in its entirety by reference. Compounds of the invention either have demonstrated or are expected to demonstrate utility for wake promoting activity.

Dipsogenia Model: Inhibition of histamine agonist-induced water drinking in the rat. Histamine, and the $H_3$-selective agonist (R)-α-methylhistamine (RAMH) induce water drinking behavior in the rat when administered either peripherally or centrally (Kraly, F. S., June, K. R. 1982 *Physiol. Behav.* 28: 841; Leibowitz, S. F. 1973 *Brain Res.* 63:440; Ligneau X., Lin, J-S., Vanni-Mercier G., Jouvet M., Muir J. L., Ganellin C. R., Stark H., Elz S., Schunack W., Schwartz, J-C. 1998 *J Pharmcol. Exp. Ther.* 287:658-66; Clapham, J. and Kilpatrick G. J. 1993 *Eur.* 1 Pharmacol. 232:99-103) an effect which is blocked by $H_3$ receptor antagonists thioperamide and ciproxifan. Compounds of the invention either have demonstrated or are expected to block RAMH induce water drinking behavior.

Novel object discrimination: Novel object discrimination (NOD; also referred to as novel object recognition) is an assay for short-term visual recognition memory that was first described by Ennaceur and Delacour (Ennaceur, A. and Delacour, J. (1988) *Behav Brain Res* 31: 47-59).

Social recognition: Social recognition (SR) is an assay for short-term social (olfactory) memory that was first described by Thor and Holloway (1982). Thor, D. and Holloway, W. (1982) *J Comp Physiolog Psychcol* 96: 1000-1006.

Compounds of the invention either have demonstrated or are expected to demonstrate inhibition of $H_3$ and thereby utility for treatment of the indications described herein.

Table B lists the Human and Rat $H_3$ binding data for Examples 1-18 of the present invention. Binding constants ($K_i$) for Examples 1-41 in the Human $H_3$ and Rat $H_3$ methods described herein are expressed by letter descriptor to indicate the following ranges: "+++" is less than 200 nM; "++" is 200-1000 nM; "+" is >1000 nM.

TABLE B
| Example | Structure | Human H₃ Ki nM | Rat H₃ Ki nM |
|---|---|---|---|
| 1 | 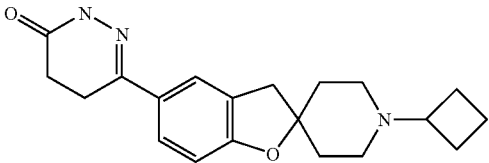 [SMILES: O=C1CCC(c2ccc3c(c2)CC2(CCN(C4CCC4)CC2)O3)=NN1] | +++ | +++ |
| 2 | 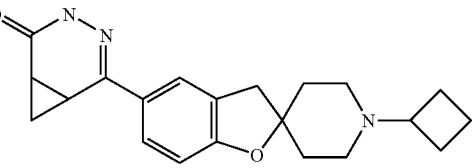 | +++ | +++ |
| 3 | 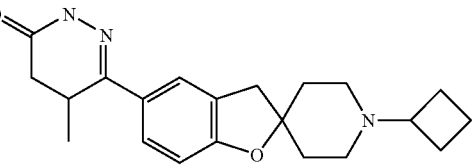 | +++ | ++ |
| 4 | 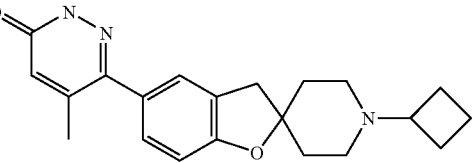 | +++ | +++ |
| 5 | 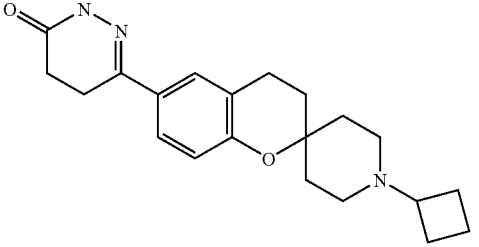 [SMILES: O=C1CCC(c2ccc3c(c2)CCC2(CCN(C4CCC4)CC2)O3)=NN1] | +++ | +++ |
| 6 | 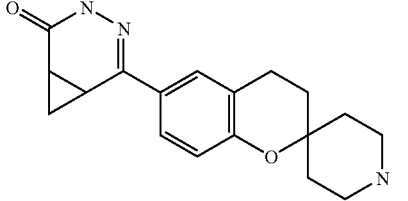 [SMILES: O=C1NN=C(c2ccc3c(c2)CCC2(CCNCC2)O3)C2CC12] | + | + |
| 7 | 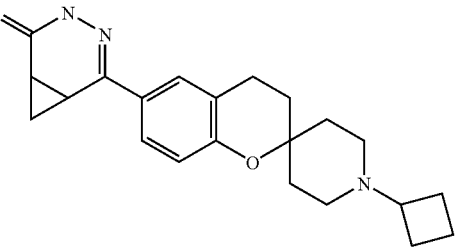 | +++ | +++ |

TABLE B-continued

| Example | Structure | Human H₃ Ki nM | Rat H₃ Ki nM |
|---|---|---|---|
| 8 | 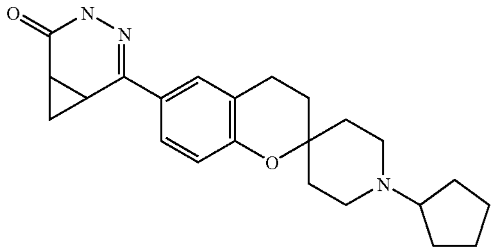 [SMILES: O=C1NN=C(c2ccc3c(c2)CCC2(CCN(C4CCCC4)CC2)O3)C2CC12] | +++ | +++ |
| 9 | 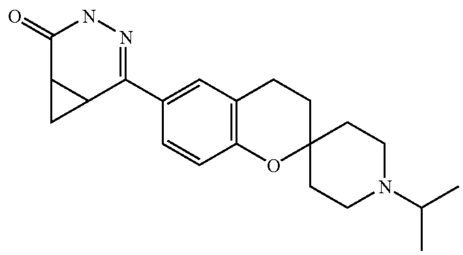 [SMILES: CC(C)N1CCC2(CCc3cc(C4=NNC(=O)C5CC45)ccc3O2)CC1] | +++ | +++ |
| 10 | 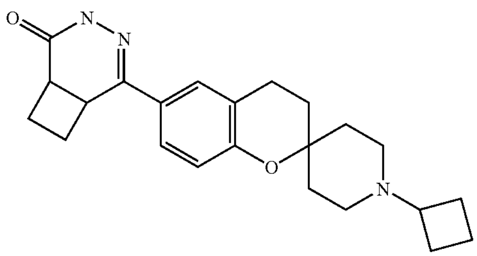 [SMILES: O=C1NN=C(c2ccc3c(c2)CCC2(CCN(C4CCC4)CC2)O3)C2CCC12] | +++ | +++ |
| 11 | 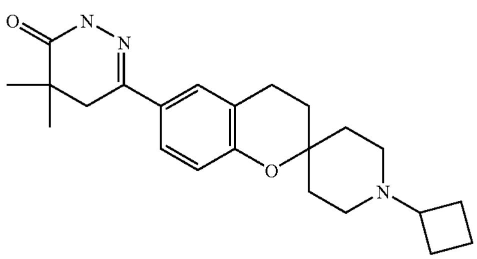 [SMILES: CC1(C)CC(c2ccc3c(c2)CCC2(CCN(C4CCC4)CC2)O3)=NNC1=O] | +++ | +++ |
| 12 | 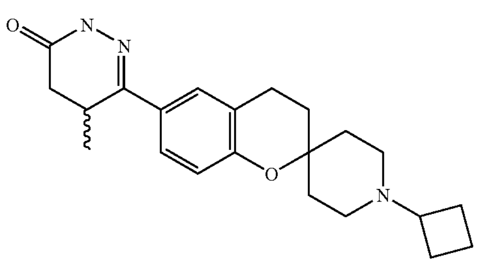 [SMILES: CC1CC(=O)NN=C1c1ccc2c(c1)CCC1(CCN(C3CCC3)CC1)O2] | +++ | +++ |
| 13 | 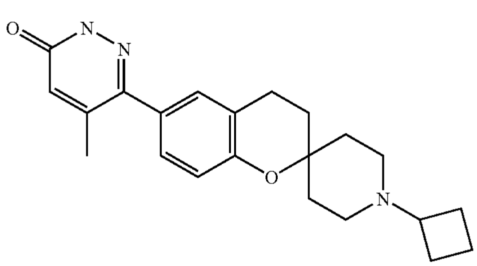 [SMILES: Cc1cc(=O)[nH]nc1-c1ccc2c(c1)CCC1(CCN(C3CCC3)CC1)O2] | +++ | +++ |

TABLE B-continued

| Example | Structure | Human H₃ Ki nM | Rat H₃ Ki nM |
|---|---|---|---|
| 14 | 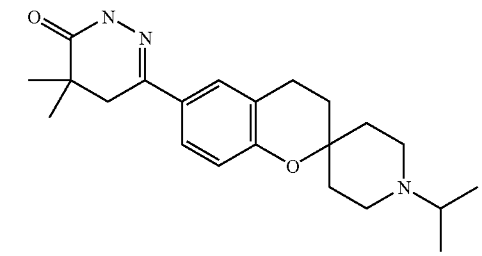 [SMILES: CC(C)N1CCC2(CCc3cc(C4=NNC(=O)C(C)(C)C4)ccc3O2)CC1] | +++ | +++ |
| 15 | 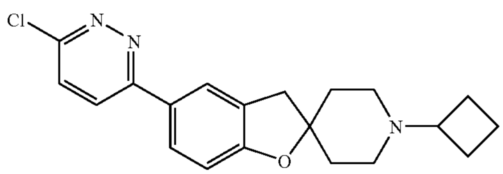 [SMILES: Clc1ccc(-c2ccc3c(c2)CC2(CCN(C4CCC4)CC2)O3)nn1] | +++ | +++ |
| 16 | 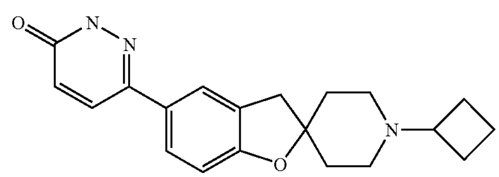 [SMILES: O=c1ccc(-c2ccc3c(c2)CC2(CCN(C4CCC4)CC2)O3)n[nH]1] | +++ | +++ |
| 18 | 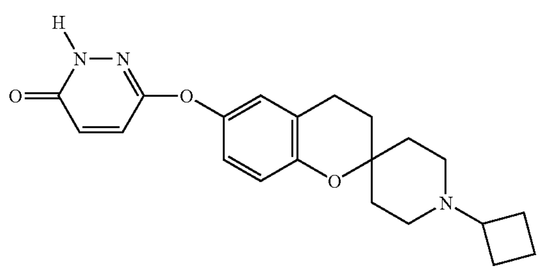 [SMILES: O=c1ccc(Oc2ccc3c(c2)CCC2(CCN(C4CCC4)CC2)O3)n[nH]1] | +++ | +++ |
| 19 | 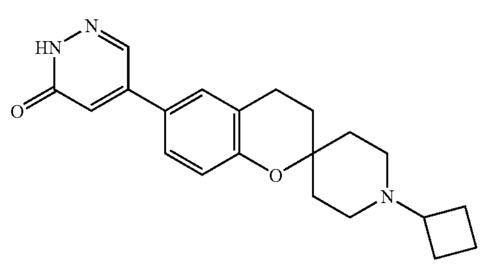 [SMILES: O=c1cc(-c2ccc3c(c2)CCC2(CCN(C4CCC4)CC2)O3)cn[nH]1] | +++ | +++ |
| 20 | 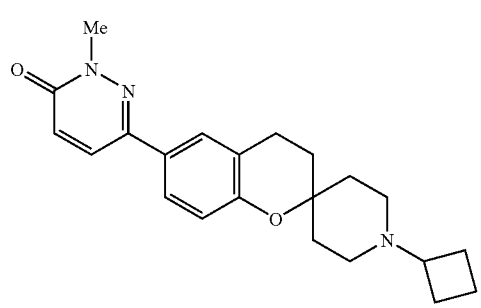 | +++ | +++ |

TABLE B-continued
| Example | Structure | Human H₃ Ki nM | Rat H₃ Ki nM |
|---|---|---|---|
| 21 | 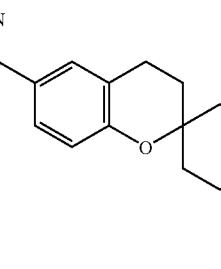 | +++ | +++ |
| 22 | 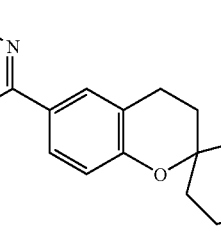 | +++ | +++ |
| 23 | 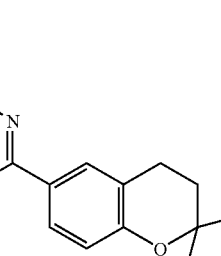 | +++ | +++ |
| 24 | 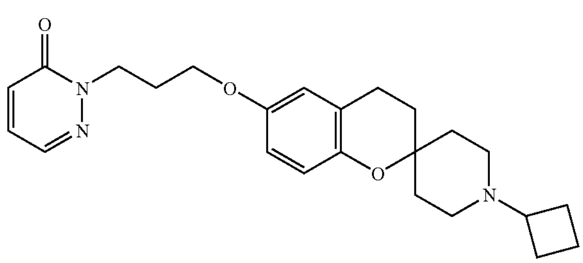 [SMILES: O=c1cccnn1CCCOc1ccc2c(c1)CCC1(CCN(C3CCC3)CC1)O2] | +++ | +++ |
| 25 | 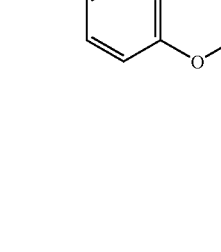 | +++ | +++ |

TABLE B-continued

| Example | Structure | Human H₃ Ki nM | Rat H₃ Ki nM |
|---------|-----------|----------------|--------------|
| 26 | 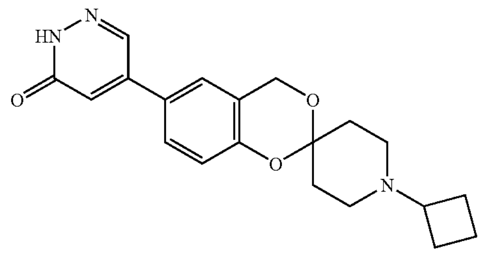 [SMILES: O=c1cc(-c2ccc3c(c2)COC2(CCN(C4CCC4)CC2)O3)cn[nH]1] | +++ | +++ |
| 27 | 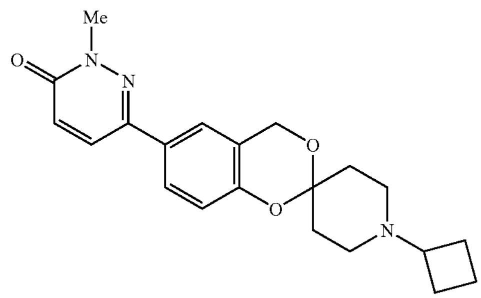 [SMILES: Cn1nc(-c2ccc3c(c2)COC2(CCN(C4CCC4)CC2)O3)ccc1=O] | +++ | +++ |
| 28 | 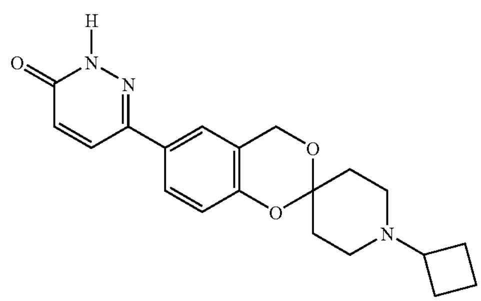 | +++ | +++ |
| 29 | 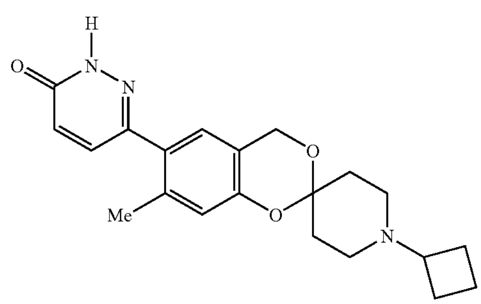 [SMILES: Cc1cc2c(cc1-c1ccc(=O)[nH]n1)COC1(CCN(C3CCC3)CC1)O2] | ++ | ++ |
| 30 | 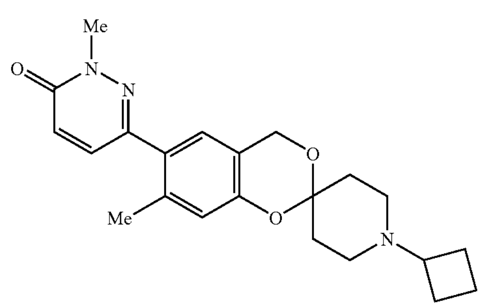 | +++ | +++ |

TABLE B-continued

| Example | Structure | Human H₃ Ki nM | Rat H₃ Ki nM |
|---|---|---|---|
| 31 | 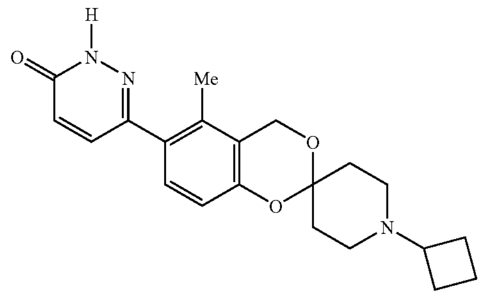 [SMILES: Cc1c(-c2ccc(=O)[nH]n2)ccc2c1COC1(CCN(C3CCC3)CC1)O2] | +++ | +++ |
| 32 | 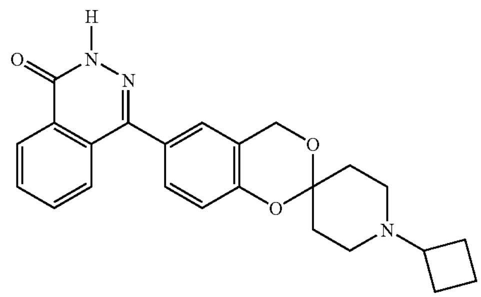 [SMILES: O=c1[nH]nc(-c2ccc3c(c2)COC2(CCN(C4CCC4)CC2)O3)c2ccccc12] | +++ | +++ |
| 33 | 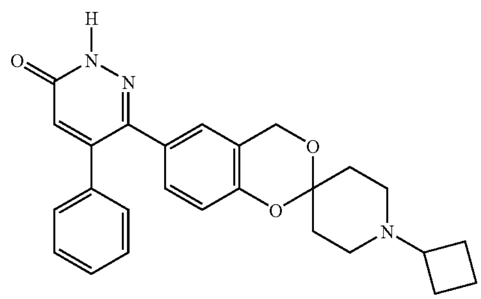 [SMILES: O=c1cc(-c2ccccc2)c(-c2ccc3c(c2)COC2(CCN(C4CCC4)CC2)O3)n[nH]1] | +++ | +++ |
| 34 | 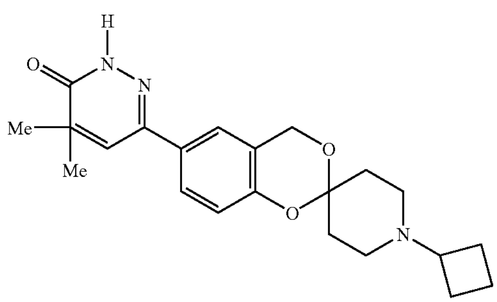 | +++ | +++ |
| 36 | 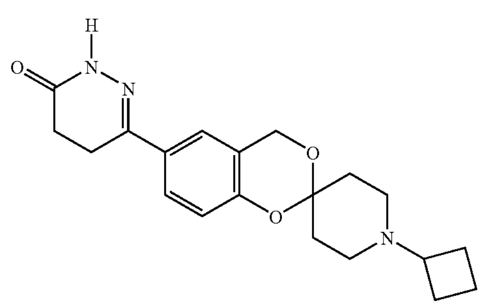 [SMILES: O=C1CCC(c2ccc3c(c2)COC2(CCN(C4CCC4)CC2)O3)=NN1] | +++ | +++ |

TABLE B-continued
| Example | Structure | Human H₃ Ki nM | Rat H₃ Ki nM |
|---|---|---|---|
| 37 | 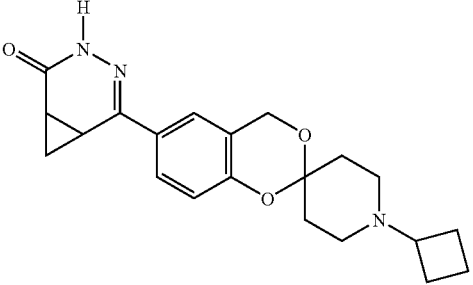 [SMILES: O=C1NN=C(c2ccc3c(c2)COC2(CCN(C4CCC4)CC2)O3)C2CC12] | +++ | +++ |
| 38 | 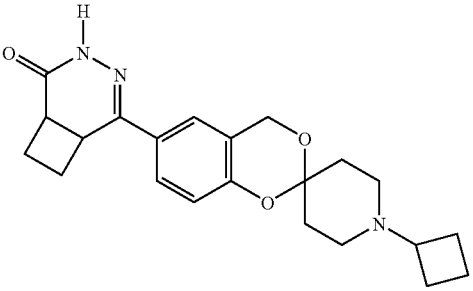 [SMILES: O=C1NN=C(c2ccc3c(c2)COC2(CCN(C4CCC4)CC2)O3)C2CCC12] | +++ | +++ |
| 39 | 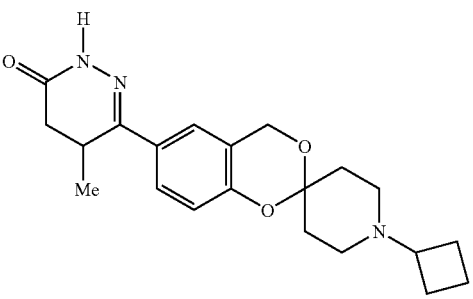 [SMILES: CC1CC(=O)NN=C1c1ccc2c(c1)COC1(CCN(C3CCC3)CC1)O2] | +++ | +++ |
| 40 | 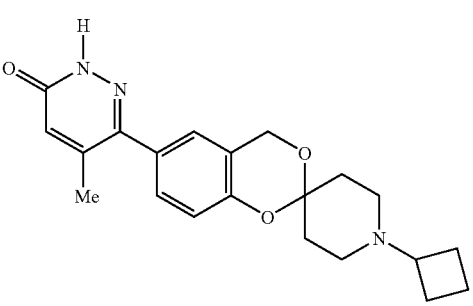 [SMILES: Cc1cc(=O)[nH]nc1-c1ccc2c(c1)COC1(CCN(C3CCC3)CC1)O2] | +++ | +++ |
| 41 | 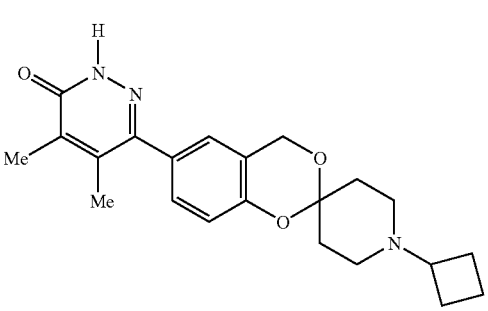 [SMILES: Cc1c(-c2ccc3c(c2)COC2(CCN(C4CCC4)CC2)O3)n[nH]c(=O)c1C] | +++ | +++ |

Dosage and Formulation

For therapeutic purposes, the compounds of the present invention can be administered by any means that results in the contact of the active agent with the agent's site of action in the body of the subject. The compounds may be administered by any conventional means available for use in conjunction with pharmaceuticals, either as individual therapeutic agents or in combination with other therapeutic agents, such as, for example, analgesics. The compounds of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The compounds may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, 20$^{th}$ ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the afore listed excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

References

Alguacil L. F.; Perez-Garcia C. Histamine $H_3$ Receptor: A potential drug target for the treatment of central nervous systems disorders. *Current Drug Targets-CNS & Neurological Disorders* 2003, 2, 303-131.

Arrang, J. M.; Garbarg, M.; Schwartz, J. C., Auto-inhibition of brain histamine release mediated by a novel class ($H_3$) of histamine receptor. *Nature* 1983, 302, (5911), 832-7.

Celanire, S.; Wijtmans, M.; Talaga, P.; Leurs, R.; de Esch, I. J., Keynote review: histamine $H_3$ receptor antagonists reach out for the clinic. *Drug Discov Today* 2005, 10, (23-24), 1613-27.

Chazot P. L.; Hann V. $H_3$ histamine receptor isoforms: New therapeutic targets in the CNS? *Current Opinions in Investigational Drugs* 2001, 2, 1428-1431.

Chen Z. Effect of histamine $H_3$-receptor antagonist clobenprobit on spatial memory of radial maze performance in rats. *Acta Pharmacol Sin* 2000, 21, 905-910.

Esbenshade, T. A.; ox, G. B.; Cowart, M. D. Histamine $H_3$ receptor antagonists: Preclinical promise for treating obesity and cognitive disorders. *Molecular interventions* 2006, 6, 77-88.

Fox G. B.; Pan J. B.; Esbenshade T. A.; Bennani Y. L.; Black L. A.; Faghih R.; Hancock A. A.; Decker M. W. Effects of histamine $H_3$ receptor ligands GT-2331 and ciproxifan in a repeated acquisition response in the spontaneously hypertensive rat pup. *Behav. Brain Res.* 2002, 131, 151-161.

Fox G. B.; Pan J. B.; Radek R. J.; Lewis A. M.; Bitner R. S.; Esbenshade T. A.; Faghih R.; Bennani Y. L.; Williams W.; Yao B. B. Decker M. W.; Hancock A. A. Two novel and selective nonimidazole $H_3$ receptor Antagonists A-304121 and A-317920: II. In vivo behavioral and neurophysiological characterization. *J. Pharmacol. Exper. Ther.* 2003, 305, 897-908.

Hancock, A. A.; Esbenshade, T. A.; Krueger, K. M.; Yao, B. B., Genetic and pharmacological aspects of histamine $H_3$ receptor heterogeneity. *Life Sci* 2003, 73, (24), 3043-72.

Hancock, A. A.; Fox, G. B. Persepectives on cognitive domains, $H_3$ receptor ligands and neurological disease. *Expert Opin. Investig. Drugs,* 2004, 13, 1237-1248.

Komater V. A.; Browman K. E.; Curzon P.; Hancock A. A.; Decker M. W.; Fox B. $H_3$ receptor blockade by thioperamide enhances cognition in rats without inducing locomotor sensitization. *Psychopharmacology* 2003, 167, 363-372.

Leurs R.; Blandina P.; Tedford C.; Timmerman H. Therapeutic potential of histamine $H_3$ receptor agonists and antagonists. *Trends in Pharmacology* 1998, 19, 177-183.

Leurs, R.; Bakker, R. A.; Timmerman, H.; de Esch, I. J., The histamine $H_3$ receptor: from gene cloning to $H_3$ receptor drugs. *Nat Rev Drug Discov* 2005, 4, (2), 107-20.

Lin, J. S.; Sakai, K.; Vanni-Mercier, G.; Arrang, J. M.; Garbarg, M.; Schwartz, J. C.; Jouvet, M., Involvement of histaminergic neurons in arousal mechanisms demonstrated with $H_3$-receptor ligands in the cat. *Brain Res* 1990, 523, (2), 325-30.

Lloyd G. K.; Williams M. Neuronal nicotinic acetylcholine receptors as novel drug targets. *Pharmacol Exp Ther.* 2000, 292, 461-467.

Monti, J. M.; Jantos, H.; Ponzoni, A.; Monti, D., Sleep and waking during acute histamine $H_3$ agonist BP 2.94 or $H_3$ antagonist carboperamide (MR 16155) administration in rats. *Neuropsychopharmacology* 1996, 15, 31-5.

Orsetti M.; Ferretti C.; Gamalero S. R.; Ghi P. Histamine $H_3$-receptor blockade in the rat nucleus basalis magnocellularis improves place recognition memory. *Psychopharmacology* 2002, 159, 133-137.

Parmentier R.; Ohtsu H.; Djebbara-Hannas Z.; Valatx J-L.; Watanabe T.; Lin J-S. Anatomical, physiological, and pharmacological characteristics of histidine decarboxylase knock-out mice: evidence for the role of brain histamine in behavioral and sleep-wake control. *J. Neurosci.* 2002, 22, 7695-7711.

Passani, M. B.; Lin, J. S.; Hancock, A.; Crochet, S.; Blandina, P., The histamine $H_3$ receptor as a novel therapeutic target for cognitive and sleep disorders. *Trends Pharmacol Sci* 2004, 25, 618-25.

Repka-Ramirez M. S, New concepts of histamine receptors and actions. Current Allergy and Asthma Reports 2003, 3, 227-231.

Ritz A.; Curley J.; Robertson J.; Raber J. Anxiety and cognition in histamine $H_3$ receptor –/– mice. *Eur J Neurosci* 2004, 19, 1992-1996.

Rouleau, A.; Heron, A.; Cochois, V.; Pillot, C.; Schwartz, J. C.; Arrang, J. M., Cloning and expression of the mouse histamine $H_3$ receptor: evidence for multiple isoforms. J *Neurochem* 2004, 90, 1331-8.

Vanni-Merci G.; Gigout S.; Debilly G.; Lin J. S. Waking selective neurons in the posterior hypothalamus and their response to histamine $H_3$-receptor ligands: an electrophysiological study in freely moving cats. *Behav Brain Res* 2003, 144, 227-241.

Witkin, J. M.; Nelson, D. L., Selective histamine $H_3$ receptor antagonists for treatment of cognitive deficiencies and other disorders of the central nervous system. *Pharmacol Ther* 2004, 103, 1-20.

Yao, B. B.; Sharma, R.; Cassar, S.; Esbenshade, T. A.; Hancock, A. A., Cloning and pharmacological characterization of the monkey histamine $H_3$ receptor. *Eur J Pharmacol* 2003, 482, (1-3), 49-60.

What is claimed:

1. A compound of Formula (I):

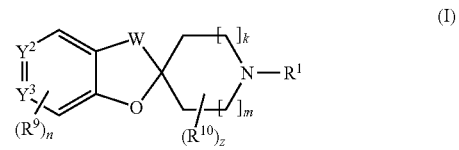

or a stereoisomeric form, mixture of stereoisomeric forms, or a pharmaceutically acceptable salt thereof, wherein:

$R^1$ is $C_3$-$C_8$ cycloalkyl;

W is $-CH_2-$, $-CH_2CH_2-$, or $-CH_2-O-$;

k is 0, 1, or 2; m is 0, 1, or 2; and the sum of m and k is 1, 2, or 3;

$Y^2=Y^3$ is $-C(X)=CH-$ or $-CH=C(X)-$;

X is $R^2$, $-OR^2$, $-(C_1$-$C_3$ alkyl)-$R^2$, $-O-(C_1$-$C_3$ alkyl)-$R^2$, $-NHR^2$, $-NHC(=O)R^2$, or $-NHC(=O)NHR^2$; wherein said $C_1$-$C_3$ alkyl is optionally substituted with $-OH$ or $C_1$-$C_4$ alkoxy;

$R^2$ is

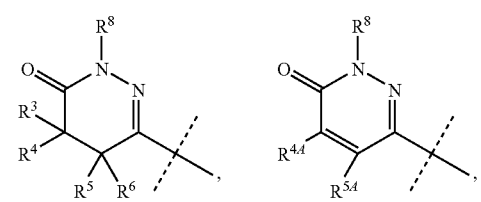

-continued

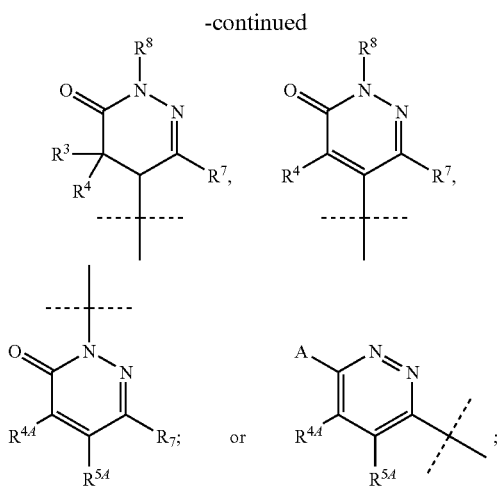

A is F, Cl, or Br;
$R^3$ is H, F, or $C_1$-$C_4$ alkyl;
$R^4$ is H, F, or $C_1$-$C_4$ alkyl;
$R^{4A}$ is H, F, Cl, Br, or $C_1$-$C_4$ alkyl;
$R^5$ is H, F, or $C_1$-$C_4$ alkyl;
$R^{5A}$ is H, F, Cl, Br, $C_1$-$C_4$ alkyl or phenyl;
or, $R^4$ and $R^5$, together with the carbon atoms to which they are attached, form a fused $C_3$-$C_6$ cycloalkyl ring optionally substituted with 1, 2, or 3 $R^{14}$;
or, $R^{4A}$ and $R^{5A}$, together with the carbon atoms to which they are attached, form a fused phenyl ring optionally substituted with 1, 2, or 3 $R^{14}$;
a $C_3$-$C_6$ cycloalkyl ring optionally substituted with 1, 2 or 3 $R^{14}$;
a 5 to 6 membered fused heteroaryl ring system containing one, two, or three heteroatoms selected from N, O, and S, wherein said heteroaryl ring system is optionally substituted with 1, 2, or 3 $R^{14}$; or
a 5 to 6 membered fused heterocycloalkyl ring system containing one, two, or three heteroatoms selected from N, O, S, SO, and $SO_2$, wherein said heterocycloalkyl ring system is optionally substituted with 1, 2, or 3 $R^{14}$;
$R^6$ is H, F, or $C_1$-$C_4$ alkyl;
$R^7$ is H, F, Cl, Br, or $C_1$-$C_4$ alkyl;
$R^8$ is H, —C(=O)$R^{27}$, —$CO_2R^{27}$, $C_1$-$C_6$ alkyl optionally substituted by 1-3 $R^{20}$;
$C_3$-$C_8$ cycloalkyl optionally substituted by 1-3 $R^{20A}$;
$C_6$-$C_{10}$ aryl optionally substituted by 1-3 $R^{20A}$;
$C_7$-$C_{15}$ arylalkyl optionally substituted by 1-3 $R^{20A}$; or
a 5 to 10 membered heteroaryl ring system containing one, two, or three heteroatoms selected from N, O, and S, wherein said heteroaryl ring system is optionally substituted with 1-3 $R^{20A}$;
$R^9$, at each occurrence, is independently F, Cl, Br, $C_1$-$C_4$ alkyl, or $C_1$-$C_4$ alkoxy;
$R^{10}$ is F, Cl, Br, $C_1$-$C_3$ alkyl, or $C_1$-$C_3$ alkoxy;
$R^{14}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=)$NR^{23}R^{24}$, —$NR^{27}C(=O)R^{21}$, —$NR^{27}C(=O)OR^{21}$, —OC(=O)$NR^{23}R^{24}$, —$NR^{27}C(=S)R^{21}$, —$SR^{21}$, —S(O)$R^{21}$, or —$S(O)_2R^{21}$; $C_1$-$C_6$ alkyl optionally substituted with $OR^{26}$; $C_2$-$C_6$ alkenyl, or $C_2$-$C_6$ alkynyl;
$R^{20}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —C(=O)$NR^{23}R^{24}$, —$NR^{27}C(=O)R^{21}$, —$NR^{27}C(=O)OR^{21}$, —OC(=O)$NR^{23}R^{24}$, —$NR^{27}C(=S)R^{21}$, —$SR^{21}$, —S(O)$R^{21}$, or —$S(O)_2R^{21}$; $C_1$-$C_6$ alkyl optionally substituted with $OR^{26}$; $C_2$-$C_6$ alkenyl, $C_2$-$C_6$ alkynyl, $C_3$-$C_7$ cycloalkyl, phenyl, 3- to 7-membered heterocycloalkyl group, or 5-or 6-membered heteroaryl group;
$R^{20A}$ at each occurrence is independently F, Cl, Br, I, —$OR^{21}$, —$OR^{22}$, —$NR^{23}R^{24}$, —NHOH, —$NO_2$, —CN, —$CF_3$, (=O), —C(=O)$R^{21}$, —$CO_2R^{21}$, —OC(=O)$R^{21}$, —C(=O)$NR^{23}R^{24}$, —$NR^{27}C(=O)R^{21}$, —$NR^{27}C(=O)OR^{21}$, —OC(=O)$NR^{23}R^{24}$, —$NR^{27}C(=S)R^{21}$, —$SR^{21}$, —S(O)$R^{21}$, or —$S(O)_2R^{21}$; $C_1$-$C_6$ alkyl optionally substituted with $OR^{26}$; $C_2$-$C_6$ alkenyl, or $C_2$-$C_6$ alkynyl;
$R^{21}$ at each occurrence is independently H, $C_1$-$C_6$ alkyl, $C_6$-$C_{10}$ aryl, or $C_7$-$C_{15}$ arylalkyl;
$R^{22}$ at each occurrence is independently the residue of an amino acid after the hydroxyl group of the carboxyl group is removed;
$R^{23}$ and $R^{24}$ at each occurrence are independently selected from H, $C_1$-$C_6$ alkyl, and $C_6$-$C_{10}$ aryl;
or, $R^{23}$ and $R^{24}$, together with the nitrogen atom to which they are attached, form a 3 to 7 membered heterocycloalkyl ring system containing one, two, or three heteroatoms selected from N, O, and S, wherein said heterocycloalkyl ring system is optionally substituted with =O;
$R^{26}$ is H or $C_1$-$C_6$ alkyl;
$R^{27}$ is H or $C_1$-$C_6$ alkyl;
n is 0, 1, 2, or 3; and
z is 0, 1, 2, 3, 4, 5, or 6.

2. A compound according to claim 1 wherein W is —$CH_2$— or —$CH_2$—$CH_2$—.

3. A compound according to claim 1 wherein $R^2$ is

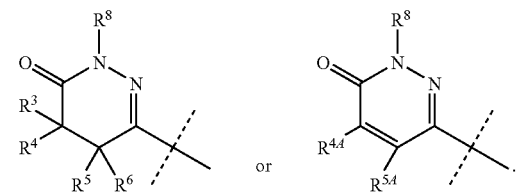

4. A compound according to claim 1 wherein $R^4$ and $R^5$, together with the carbon atoms to which they are attached, form a fused cyclopropyl or cyclobutyl ring.

5. A compound according to claim 1 wherein $R^{4A}$ and $R^{5A}$, together with the carbon atoms to which they are attached, form a fused phenyl, thienyl, pyrrolyl, oxazolyl, pyridinyl, cyclopropyl, cyclobutyl, cyclopentyl, or cyclohexyl ring.

6. A compound according to claim 1 wherein k is 1.

7. A compound according to claim 1 wherein m is 1.

8. A compound according to claim 1 wherein the sum of m and k is 2.

9. A compound according to claim 1 wherein $Y^2$=$Y^3$ is —C(X)=CH—.

10. A compound according to claim 1 wherein X is $R^2$.

11. A compound according to claim 1 wherein X is —$OR^2$.

12. A compound according to claim 1 wherein $R^8$ is H.

13. A compound according to claim 1 wherein $R^8$ is $C_1$-$C_6$ alkyl optionally substituted by 1-3 $R^{20}$.

14. A compound according to claim 1 wherein $R^9$ is $C_1$-$C_4$ alkyl.

15. A compound according to claim 1 wherein n is 0.

16. A compound according to claim 1 wherein n is 1.

17. A compound according to claim 1 wherein z is 0.

18. A compound according to claim 1 that is a compound of Formula (II):

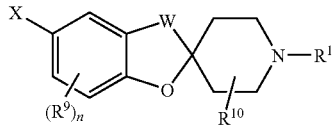
(II)

or a stereoisomeric form, mixture of stereoisomeric forms or a pharmaceutically acceptable salt thereof,
wherein:
$R^1$ is $C_3$-$C_8$ cycloalkyl;
W is —$CH_2$— or —$CH_2$—$CH_2$—;
X is $R^2$, —$OR^2$, or —$NHR^2$;
$R^2$ is

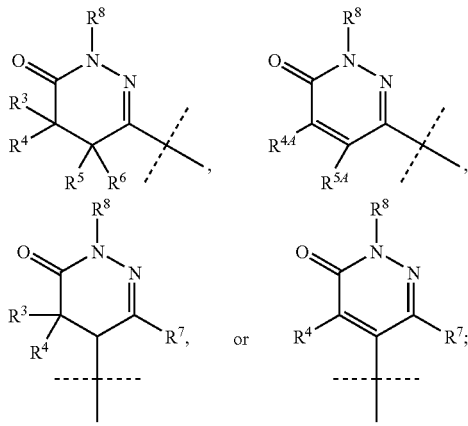

$R^3$ is H or $C_1$-$C_4$ alkyl;
$R^4$ is H or $C_1$-$C_4$ alkyl;
$R^{4A}$ is H or $C_1$-$C_4$ alkyl;
$R^5$ is H or $C_1$-$C_4$ alkyl;
$R^{5A}$ is H, $C_1$-$C_4$ alkyl, or phenyl;
or, $R^4$ and $R^5$, together with the carbon atoms to which they are attached, form a fused $C_3$-$C_6$ cycloalkyl ring optionally substituted with 1-3 $R^{14}$;
or, $R^{4A}$ and $R^{5A}$, together with the carbon atoms to which they are attached, form a fused phenyl ring optionally substituted with 1-3 $R^{14}$;
a $C_3$-$C_6$ cycloalkyl ring optionally substituted with 1-3 $R^{14}$;
a 5 to 6 membered fused heteroaryl ring system containing one, two, or three heteroatoms selected from N, O, and S, wherein said heteroaryl ring system is optionally substituted with 1-3 $R^{14}$; or
a 5 to 6 membered fused heterocycloalkyl ring system containing one, two, or three heteroatoms selected from N, O, S, SO, and $SO_2$, wherein said heterocycloalkyl ring system is optionally substituted with 1-3 $R^{14}$;
$R^6$ is H or $C_1$-$C_4$ alkyl; and
$R^7$ is H or $C_1$-$C_4$ alkyl.

19. A compound according to claim 18 wherein $R^1$ is cyclobutyl or cyclopentyl.

20. A compound according to claim 18 wherein $R^2$ is

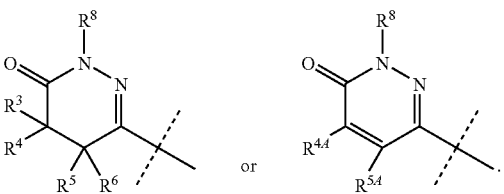

21. A compound according to claim 18 wherein $R^2$ is

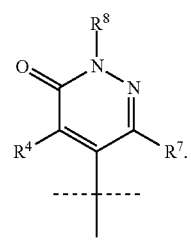

22. A compound according to claim 18 wherein $R^4$ and $R^5$, together with the carbon atoms to which they are attached, form a fused cyclopropyl or cyclobutyl ring.

23. A compound according to claim 18 wherein $R^{4A}$ and $R^{5A}$, together with the carbon atoms to which they are attached, form a fused phenyl, thienyl, pyrrolyl, oxazolyl, pyridinyl, cyclopropyl, cyclobutyl, cyclopentyl, or cyclohexyl ring.

24. A compound according to claim 18 wherein $R^8$ is H.

25. A compound according to claim 1 that is a compound of Formula (III):

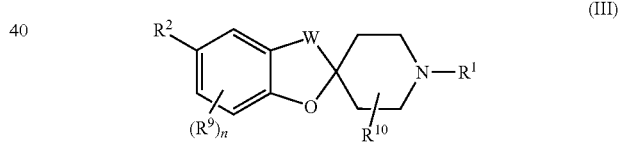
(III)

or a stereoisomeric form, mixture of stereoisomeric forms or a pharmaceutically acceptable salt thereof,
wherein:
$R^1$ is $C_3$-$C_6$ cycloalkyl;
W is —$CH_2$— or —$CH_2$—$CH_2$—;
$R^2$ is

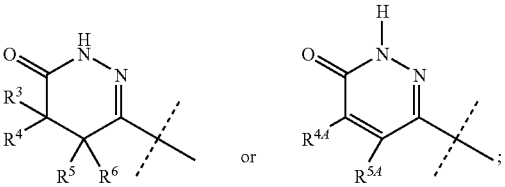

$R^3$ is H, methyl, or ethyl;
$R^4$ is H, methyl, or ethyl;
$R^{4A}$ is H, methyl, or ethyl;
$R^5$ is H, methyl, or ethyl;
$R^{5A}$ is H, methyl, or ethyl;

or, $R^4$ and $R^5$, together with the carbon atoms to which they are attached, form a fused $C_3$-$C_6$ cycloalkyl ring;

or, $R^{4A}$ and $R^{5A}$, together with the carbon atoms to which they are attached, form a fused phenyl ring;

$C_3$-$C_6$ cycloalkyl ring;

a 5 to 6 membered fused heteroaryl ring system containing one, two, or three heteroatoms selected from N, O, and S; or 5 to 6 membered fused heterocycloalkyl ring system containing one, two, or three heteroatoms selected from N, O, S, SO, and $SO_2$;

$R^6$ is H, methyl, or ethyl;

$R^7$ is H, methyl, or ethyl;

$R^9$, at each occurrence, is independently, F, Cl, methyl, ethyl, methoxy, or ethoxy;

$R^{10}$ is F, Cl, methyl, ethyl, methoxy, or ethoxy; and n is 0, 1, or 2.

26. A compound according to claim 1 that is a compound of Formula (III):

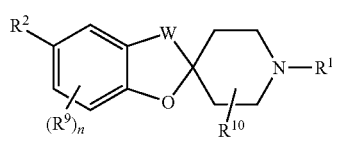

(III)

or a stereoisomeric form, mixture of stereoisomeric forms or a pharmaceutically acceptable salt thereof, wherein:

$R^1$ is cyclobutyl or cyclopentyl;

W is —$CH_2$— or —$CH_2$—$CH_2$—;

$R^2$ is

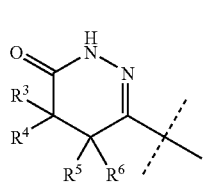 or 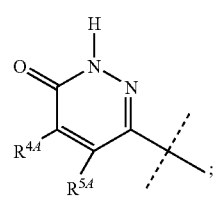;

$R^3$ is H, methyl, or ethyl;

$R^4$ is H, methyl, or ethyl;

$R^{4A}$ is H, methyl, or ethyl;

$R^5$ is H, methyl, or ethyl;

$R^{5A}$ is H, methyl, or ethyl;

or, $R^4$ and $R^5$, together with the carbon atoms to which they are attached, form a fused cyclopropyl, cyclobutyl, or cyclopentyl ring;

or, $R^{4A}$ and $R^{5A}$, together with the carbon atoms to which they are attached, form a fused phenyl, thienyl, pyrrolyl, oxazolyl, pyridinyl, cyclopropyl, cyclobutyl, cyclopentyl, or cyclohexyl ring;

$R^6$ is H, methyl, or ethyl;

$R^7$ is H, methyl, or ethyl;

$R^9$, at each occurrence, is independently, F, Cl, methyl, ethyl, methoxy, or ethoxy;

$R^{10}$ is F, Cl, methyl, ethyl, methoxy, or ethoxy; and n is 0, 1, or 2.

27. A compound according to claim 1 selected from the group consisting of:

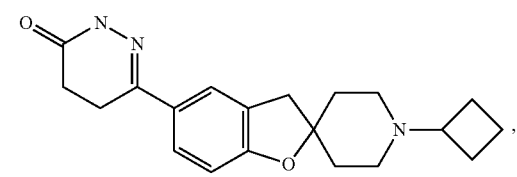,

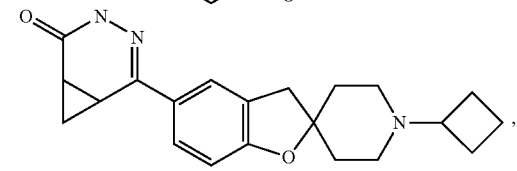,

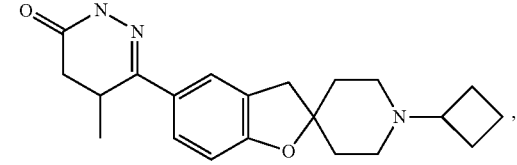,

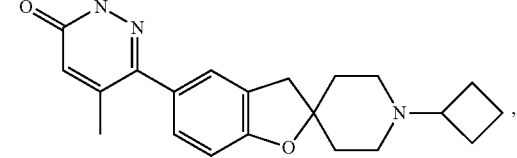,

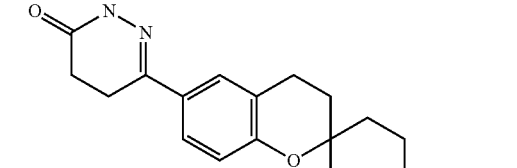,

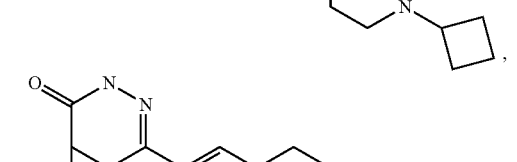,

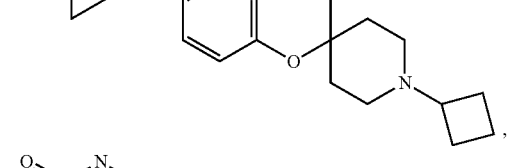,

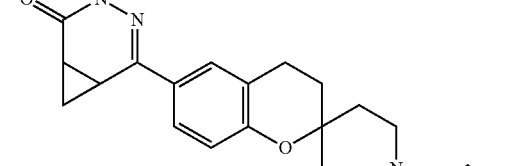,

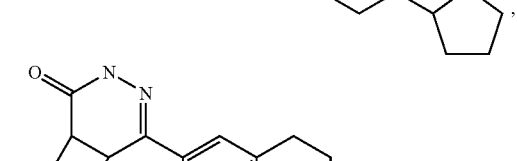,

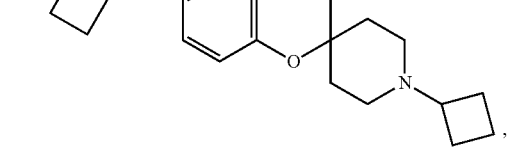,

-continued
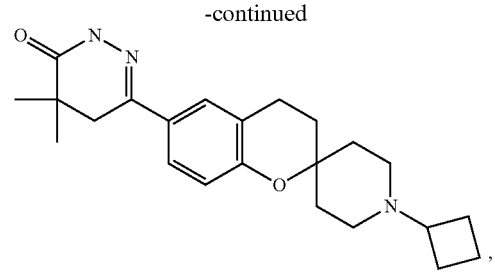
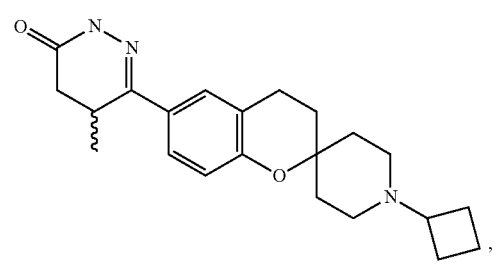
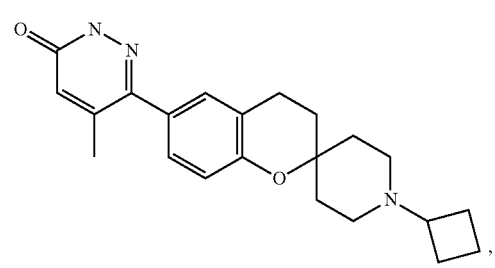
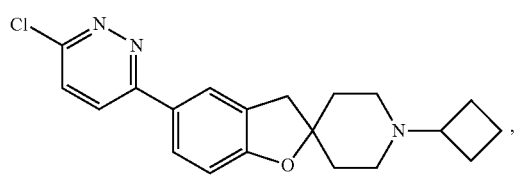
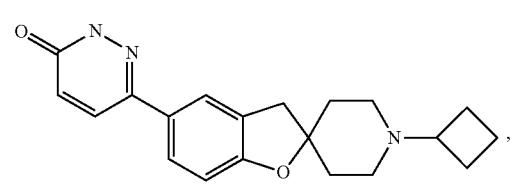
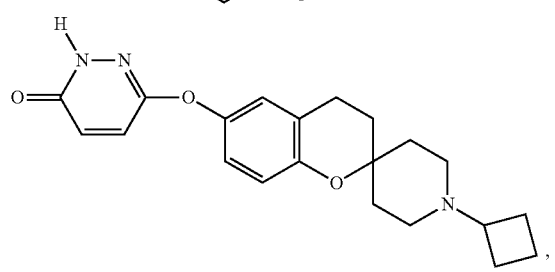
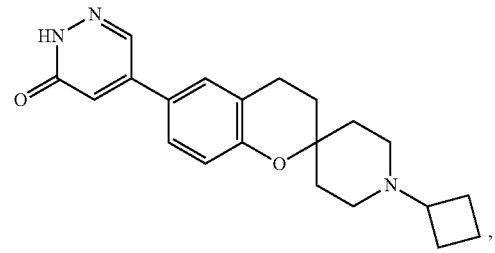
-continued
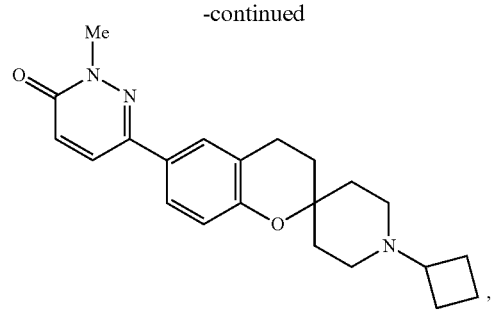
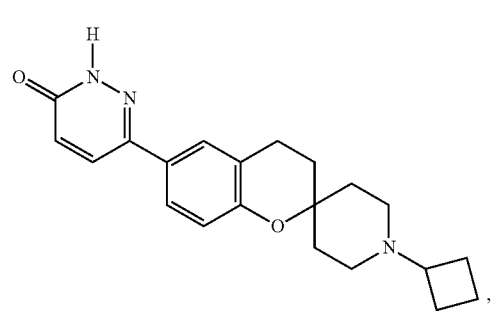
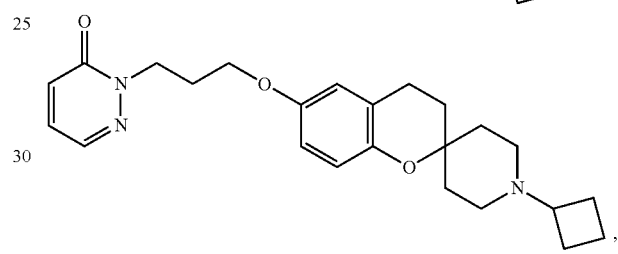
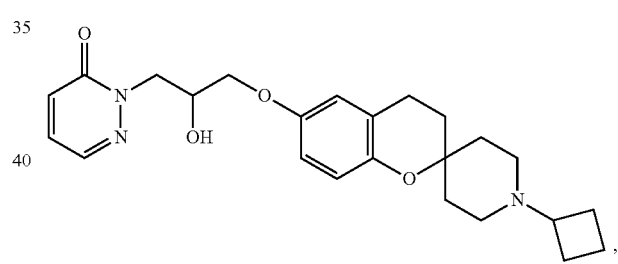
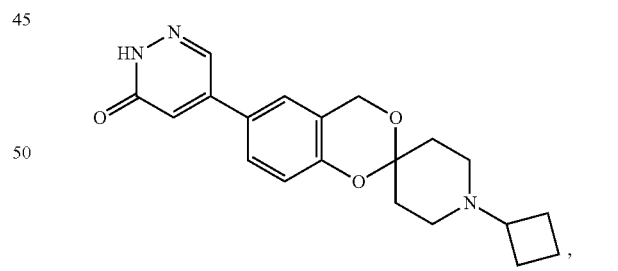
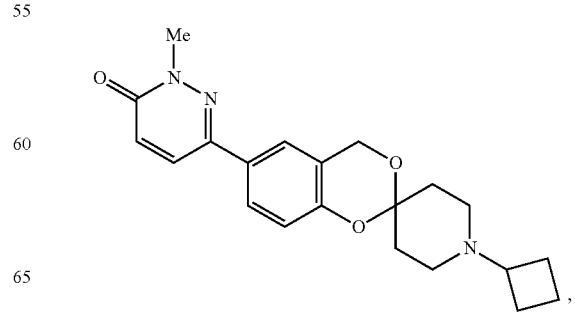

81
-continued
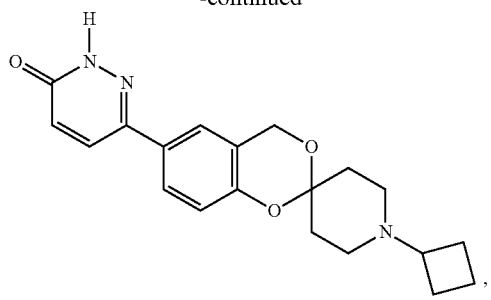
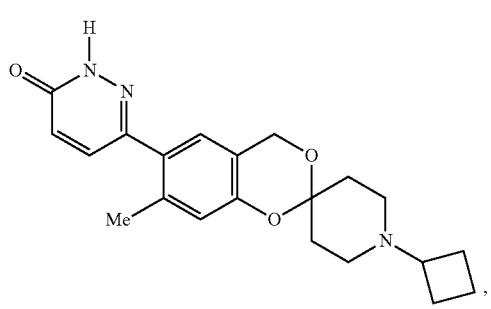
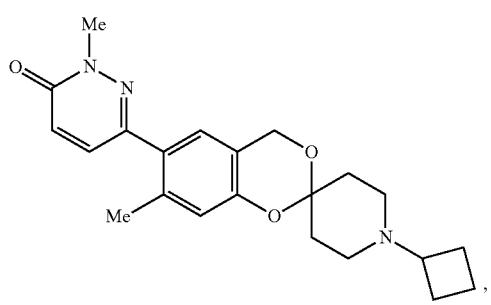
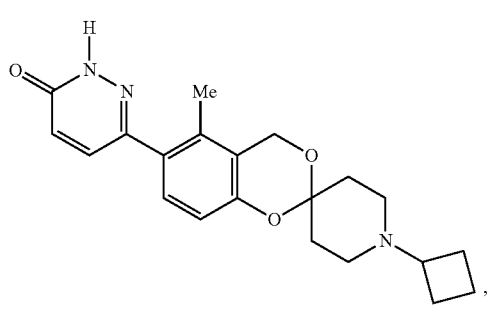
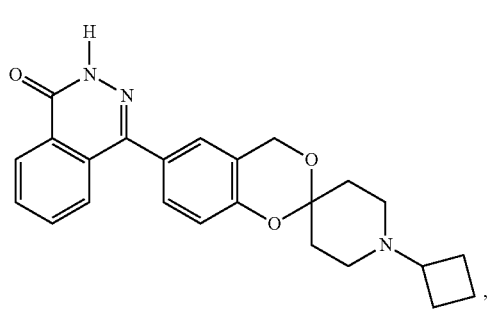
82
-continued
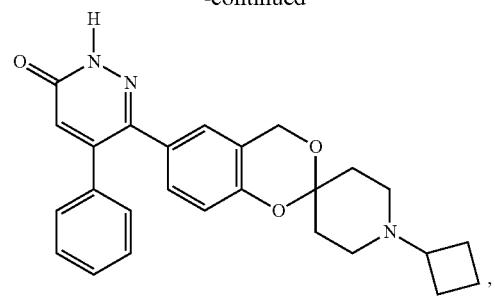
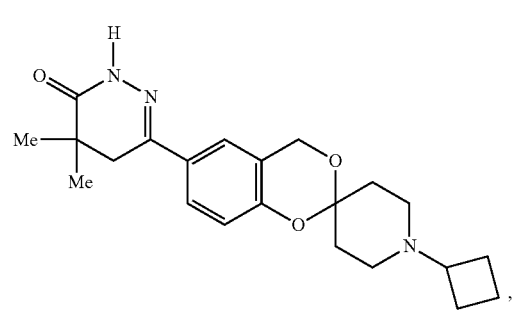
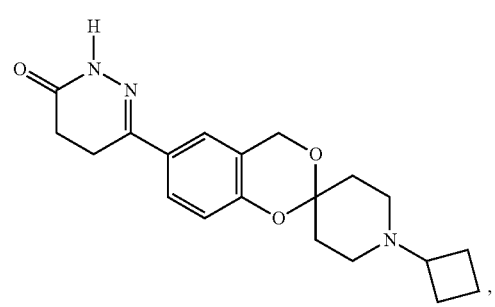
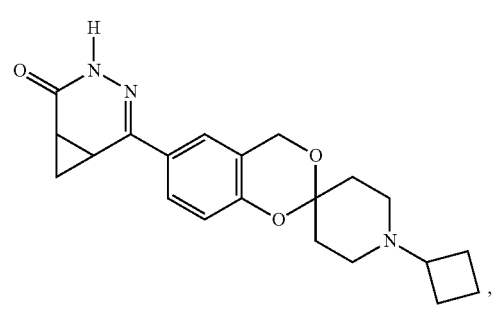
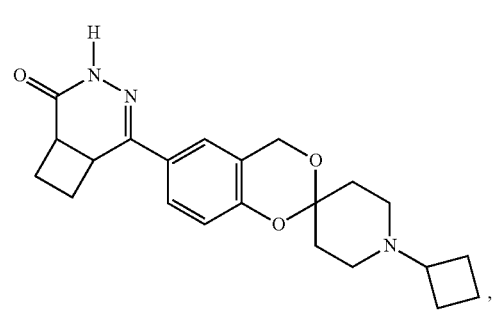

-continued

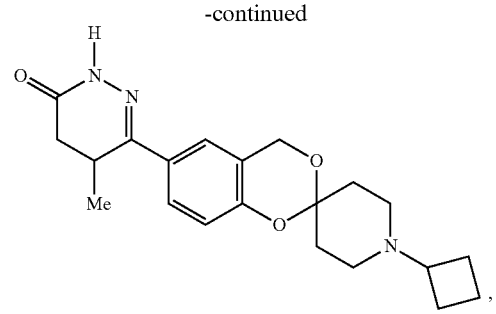
,

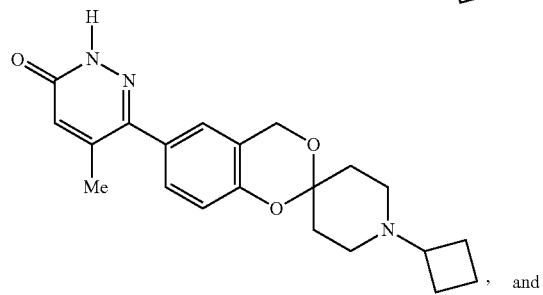
, and

-continued

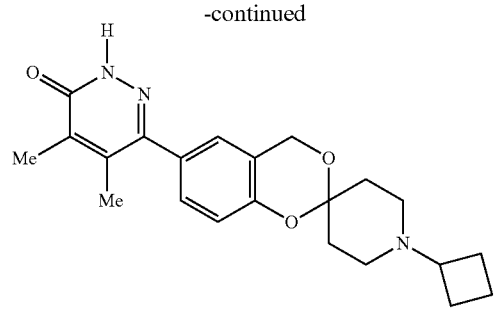

or a stereoisomeric form, mixture of stereoisomeric forms or a pharmaceutically acceptable salt thereof.

28. A pharmaceutical composition comprising a compound according to claim 1, or a stereoisomeric form, mixture of stereoisomeric forms or a pharmaceutically acceptable salt thereof, and one or more pharmaceutically acceptable excipients.

29. A compound according to claim 1 wherein W is —CH$_2$—O.

* * * * *